United States Patent
Manoharan et al.

(10) Patent No.: US 6,762,281 B2
(45) Date of Patent: *Jul. 13, 2004

(54) PROCESS FOR PREPARING PEPTIDE DERIVATIZED OLIGOMERIC COMPOUNDS

(75) Inventors: Muthiah Manoharan, Carlsbad, CA (US); Andrei P. Guzaev, Carlsbad, CA (US)

(73) Assignee: ISIS Pharmaceuticals, Inc., Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/949,474

(22) Filed: Sep. 7, 2001

(65) Prior Publication Data

US 2002/0156235 A1 Oct. 24, 2002

Related U.S. Application Data

(63) Continuation-in-part of application No. 09/658,517, filed on Sep. 8, 2000, now Pat. No. 6,559,279.

(51) Int. Cl.[7] .......................... C07H 21/04; C07K 1/02; C07K 1/113
(52) U.S. Cl. ...................... 530/322; 525/54.2; 530/333; 530/338; 530/345; 536/25.3; 536/25.31
(58) Field of Search ................................. 530/322, 323, 530/338, 345; 514/2, 8; 525/54.2; 536/25.3, 25.31, 25.33, 25.34

(56) References Cited

U.S. PATENT DOCUMENTS 6,255,476 B1   7/2001  Vinayak et al. .......... 536/25.32
6,559,279 B1 * 5/2003  Manoharan et al. ........ 530/322

FOREIGN PATENT DOCUMENTS

WO        91/14696      10/1991
WO     WO 99/05302       2/1999
WO     WO 00/20622       4/2000

OTHER PUBLICATIONS

Azhayeva et al. Looped oligonucleotides form stable hybrid complexes with a single–stranded DNA. Nucleic Acids Research. 1995, vol. 23, No. 7, pp. 1170–1176.*

Antopolsky, M., et al., "Peptide–oligonucleotide phosphorothioate conjugates with membrane translocation and nuclear localization properties," *Bioconjugate Chem.*, 1999, 10, 598–606.

Antopolsky, M., et al., "Stepwise solid–phase synthesis of peptide–oligonucleotide conjugates on new solid supports," *Helv. Chim. Acta*, 1999, 82, 2130–2140.

Astriab–Fisher, A., et al., "Antisense inhibition of P–glycoprotein expression using peptide–oligonucleotide conjugates," *Biochem. Pharmacol.*, 2000, 60, 83–90.

Bayer, E., et al., "Improved conditions for solid phase synthesis of oligonucleotides on PS–PEG copolymers," *Verlag der Zeitschrift für Naturforschung*, 1995, 1096–1100.

Beaucage, S.L., et al., "Advances in the synthesis of oligonucleotides by the phosphoramidite approach," *Current Protocols in Nucleic Acid Chemistry*, 1992, 48(12), 2223–2311.

Beaucage, S.L., et al., "Synthetic strategies and parameters involved in the synthesis of oligodeoxyribonucleotides according to the phosphoramidite method," *Curr. Protocols Nucleic Acid Chem.*, 2000, 3.3.1–3.3.20.

(List continued on next page.)

*Primary Examiner*—Jeffrey Edwin Russel
(74) *Attorney, Agent, or Firm*—Woodcock Washburn LLP

(57) ABSTRACT

Methods of preparing peptide linked oligomeric compounds are provided. The method is useful for preparing larger scale amounts of peptide linked oligomeric compounds. More particularly, the synthesis of peptide linked oligomeric compounds is performed without the problems of aggregation associated with electrostatic interactions. The present method describes using equimolar amounts of oligomeric compounds and peptide reagents providing for an increase in overall efficiency.

24 Claims, 3 Drawing Sheets

OTHER PUBLICATIONS

Bongardt, P., et al., "Synthesis and characterization of very short peptide–oligonucleotide conjugates used for the transport of antisense oligonucleotides," *Innovation Perspect. Solid Phase Synth. Comb. Libr., Collect 680AAA*, 1999, 267–270.

Bongartz J., et al., "Improved biological activity of antisense oligonucleotides conjugated to a fusogenic peptide", *Nucl. Acids Res.*, 1994, 22(22), 4681–4688.

Chaloin, L., et al., "Design of carrier peptide–oligonucleotide conjugates with rapid membrane translocation and nuclear localization properties," *Biochem. Biophys. Res. Commun.*, 1998, 243, 601–608.

de la Torre, B. G., et al., "Synthesis and binding properties of oligonucleotides carrying nuclear localization sequences," *Bioconjugate Chem.*, 1999, 10, 1005–1012.

De Napoli, L., et al., "A new solid–phase synthesis of oligonucleotides 3'–conjugated with peptides," *Bioorg. Med. Chem.*, 1999, 7 395–400.

Deshpande, D., et al., "Enhanced cellular uptake of oligonucleotides by EGF receeptor–mediated endocytosis in A549 cells," *Pharm. Res.*, 1996, 13(1), 57–61.

Frier, C., et al., "Thermodynamic melting studies on oligonucleotide–peptide conjugates," *Nucleosides Nucleotides*, 1999, 18(6&7), 1477–1478.

Fujii, M., et al., "A novel and convenient method for the synthesis of DNA conjugate," *Pept. Sci.*, 1998, Kondo, M. (ed.), 35, 293–296.

Gavin, J.A., et al., "Chiral molecular recognition in a tripeptide benzylviologen cyclopane host," *J. Org. Chem.*, 1998, 63, 7663–7669.

Grabenko, A.D., et al., "Reaction of 5–isothiocyanatohexanoic and p–isothiocyanatomethylbenzoic acids with potassium cyanide and acetone cyanohydrin," *UDC*, 1972, 532–534.

Harrison, J.G., et al., "Synthesis and hybridization analysis of a small library of peptide–oligonucleotide conjugates," *Nucleic Acids Res.*, 1998, 26(13), 3136–3145.

Lindgren, M., et al., "Cell–penetrating peptides," *TIPS*, 2000, 21, 99–103.

Manoharan, M., et al., "N–(2–cyanoethoxycarbonyloxy) succinimide: a new reagent for protection of amino groups in oligonucleotides," *J. Org. Chem.*, 1999, 64, 6468–6472.

Peyrottes, S., et al., "Studies towards The synthesis of peptide–oligonucleotide conjugates," *Nucleosides Nucleotides*, 1999, 18(6&7), 1443–1448.

Peyrottes, S., et al., "the synthesis of peptide–oligonucleotide conjugates by a fragment coupling approach," *Tetrahedron*, 1998, 54, 12513–12522.

Pooga, M., et al., "Cell penetrating PNA constructs regulate galanin receptor levels and modify pain transmission in vivo," *Nat. Biotechnol.*, 1998, 16, 857–861.

Schwarze, S.R., et al., "Protein transduction: unrestricted delivery into all cells?," *Trends Cell Biol.*, 2000, 10, 290–295.

Schwarze, S.R., et al., "In vivo protein transduction: delivery of a biologically active protein into the mouse," *Science*, 1999, 285, 1569–1572.

Soukchareun, S., et al., "Peparation and characterization of antisense oligonucleotide–peptide hybrids containing viral fusion peptides," *Bioconjugate Chem.*, 1995, 6, 43–53.

Stetsenko, D.A., et al., "Efficient conjugation of peptides to oligonucleotides by "native ligation"," *J. Org. Chem.*, 2000, 65, 4900–4908.

Sumbatyan, N.V., et al., "Synthesis of nucleopeptide–oligonucleotide conjugates," *Nucleosides Nucleotides*, 1999, 18(6&7), 1489–1490.

Truffert, J., et al., "Synthesis, purification and characterization of two peptide–oligonucleotide conjugates as potential artificial nucleases," *Tetrahedron*, 1996, 52(8), 3005–3016.

Tung, C., et al., "Dual–specificity interaction of HIV–1 TAR RNA with tat peptide–oligonucleotide conjugates," *Bioconjugate Chem.*, 1995, 6, 292–295.

Tung, C., et al., "Preparation of oligonucleotide–peptide conjugates," *Bioconjugate Chem.*, 1991, 2, 464–465.

Villa, R., et al., "Inhibition of telomerase activity by a cell–penetrating peptide nucleic acid construct in human melanoma cells," *FEBS Lett.*, 2000, 473, 241–248.

Wei, Z., et al., "Hybridization properties of oligodeoxynucleotide pairs bridged by polyarginine peptides," *Nucleic Acids Res.*, 1996, 24(4), 655–661.

Wilk, A., et al., "Assignment of absolute configuration at phosphoros in dithymidylyl(3',5') phosphormorpholidates and –posphormorpholidothioaths," *Nucleosides & Nucleotides*, 1991, 10(1–3), 319–322.

Zhu, T., et al., "Oligonucleotide–poly–L–ornithine conjugates: Binding to complementary DNA and RNA," *Antisense Res. Dev.*, 1993, 3, 265–275.

Zubin, E.M., et al., "Oligonucleotide–peptide conjugates as potential antisense agents," *FEBS Lett.*, 1999, 456, 59–62.

\* cited by examiner

Cationic peptides

Polylysine

Polyornithine

Polyarginine

Cell permeation peptide conjugates

LINKER—[ GGRQIKIWFQNRRMKWKK ]

Antennapedia Peptide

Tat Peptide

PROCESS FOR PREPARING PEPTIDE DERIVATIZED OLIGOMERIC COMPOUNDS

RELATED APPLICATION DATA

This patent application is a continuation-in-part of U.S. patent application Ser. No. 09/658,517 filed on Sep. 8, 2000, now U.S. Pat. No. 6,559,279, the contents of which are incorporated herein by reference.

FIELD OF THE INVENTION

The present invention is directed to methods for synthesizing oligomeric compounds covalently linked to peptides via a linking moiety. The method has particular advantages for larger scale synthesis of peptide linked oligomeric compounds. The present method significantly reduces the cost of preparing peptide linked oligomeric compounds. More specific objectives and advantages of the invention will hereinafter be made clear or become apparent to those skilled in the art during the course of explanation of preferred embodiments of the invention.

BACKGROUND OF THE INVENTION

Modified oligonucleotides are of great value in molecular biological research and in applications such as anti-viral therapy. Modified oligonucleotides which can block RNA translation, and are nuclease resistant, are useful as antisense reagents. In addition to oligonucleotides that have phosphodiester internucleotide linkages, sulfurized oligonucleotides which contain, for example, phosphorothioate linkages are also of interest in these areas. Because of their chirality (Rp and Sp) phosphorothioate containing oligonucleotides are useful in determining stereochemical pathways of certain enzymes which recognize nucleic acids.

It is well known that most of the bodily states in multicellular organisms, including most disease states, are effected by proteins. Such proteins, either acting directly or through their enzymatic or other function, contribute in major proportion to many diseases and regulatory functions in animals and humans. For disease states, classical therapeutics has generally focused upon interactions with such proteins in efforts to moderate their disease-causing or disease-potentiating functions. In newer therapeutic approaches, modulation of the actual production of such proteins is desired. By interfering with the production of proteins, the maximum therapeutic effect may be obtained with minimal side effects. It is therefore a general object of such therapeutic approaches to interfere with or otherwise modulate gene expression, which would lead to undesired protein formation.

One method for inhibiting specific gene expression is with the use of oligonucleotides, especially oligonucleotides which are complementary to a specific target messenger RNA (mRNA) sequence. Several oligonucleotides are currently undergoing clinical trials for such use. Phosphorothioate oligonucleotides are presently being used as such antisense agents in human clinical trials for various disease states, including use as antiviral agents.

Transcription factors interact with double-stranded DNA during regulation of transcription. Oligonucleotides can serve as competitive inhibitors of transcription factors to modulate their action. Several recent reports describe such interactions (see Bielinska, A., et. al., *Science*, 1990, 250, 997–1000; and Wu, H., et. al., *Gene*, 1990, 89, 203–209).

In addition to such use as both indirect and direct regulators of proteins, oligonucleotides and their analogs also have found use in diagnostic tests. Such diagnostic tests can be performed using biological fluids, tissues, intact cells or isolated cellular components. As with gene expression inhibition, diagnostic applications utilize the ability of oligonucleotides and their analogs to hybridize with a complementary strand of nucleic acid. Hybridization is the sequence specific hydrogen bonding of oligomeric compounds via Watson-Crick and/or Hoogsteen base pairs to RNA or DNA. The bases of such base pairs are said to be complementary to one another.

Oligonucleotides and their analogs are also widely used as research reagents. They are useful for understanding the function of many other biological molecules as well as in the preparation of other biological molecules. For example, the use of oligonucleotides and their analogs as primers in PCR reactions has given rise to an expanding commercial industry. PCR has become a mainstay of commercial and research laboratories, and applications of PCR have multiplied. For example, PCR technology now finds use in the fields of forensics, paleontology, evolutionary studies and genetic counseling. Commercialization has led to the development of kits which assist non-molecular biology-trained personnel in applying PCR. Oligonucleotides and their analogs, both natural and synthetic, are employed as primers in such PCR technology.

Oligonucleotides and their analogs are also used in other laboratory procedures. Several of these uses are described in common laboratory manuals such as *Molecular Cloning, A Laboratory Manual*, Second Ed., J. Sambrook, et al., Eds., Cold Spring Harbor Laboratory Press, 1989; and *Current Protocols In Molecular Biology*, F. M. Ausubel, et al., Eds., Current Publications, 1993. Such uses include as synthetic oligonucleotide probes, in screening expression libraries with antibodies and oligomeric compounds, DNA sequencing, in vitro amplification of DNA by the polymerase chain reaction, and in site-directed mutagenesis of cloned DNA. See Book 2 of *Molecular Cloning, A Laboratory Manual*, supra. See also "DNA-protein interactions and The Polymerase Chain Reaction" in Vol. 2 of *Current Protocols In Molecular Biology*, supra.

Oligonucleotides and their analogs can be synthesized to have customized properties that can be tailored for desired uses. Thus a number of chemical modifications have been introduced into oligomers to increase their usefulness in diagnostics, as research reagents and as therapeutic entities. Such modifications include those designed to increase binding to a target strand (i.e. increase their melting temperatures, Tm), to assist in identification of the oligonucleotide or an oligonucleotide-target complex, to increase cell penetration, to stabilize against nucleases and other enzymes that degrade or interfere with the structure or activity of the oligonucleotides and their analogs, to provide a mode of disruption (terminating event) once sequence-specifically bound to a target, and to improve the pharmacokinetic properties of the oligonucleotide.

The chemical literature discloses numerous protocols for coupling nucleosides through phosphorous-containing covalent linkages to produce oligonucleotides of defined sequence. One of the most routinely used protocols is the phosphoramidite protocol (see, e.g., Advances in the Synthesis of Oligonucleotides by the Phosphoramidite Approach, Beaucage, S. L.; Iyer, R. P., *Tetrahedron*, 1992, 48, 2223–2311 and references cited therein; and The synthesis of Modified Oligonucleotides by the Phosphoramidite Approach and their applications, Beaucage, S. L.; Iyer, R. P., *Tetrahedron*, 1993, 49, 6123–6194 and references cited therein), wherein a nucleoside or oligonucleotide having a free hydroxyl group is reacted with a protected phosphoramidite monomer in the presence of a weak acid to form a phosphite-linked structure. Oxidation of the phosphite linkage with a suitable reagent effects conversion of a $P^{III}$ internucleoside linkage to a $P^V$ internucleoside linkage. For the purpose of this application, such reagents include oxygen transfer reagents and sulfur transfer reagents. Subsequent hydrolysis of the cyanoethyl group yields the desired phosphodiester or phosphorothioate linkage.

Phosphoramidites are commercially available from a variety of commercial sources (included are: Glen Research, Sterling, Va.; Amersham Pharmacia Biotech Inc., Piscataway, N.J.; Cruachem Inc., Aston, Pa.; Chemgenes Corporation, Waltham, Mass.; Proligo LLC, Boulder, Colo.; PE Biosystems, Foster City Calif.; Beckman Coulter Inc., Fullerton, Calif.).

Peptide conjugates of antisense compounds have been prepared to enhance the overall effect of these compounds. In order to change pharmacokinetic distribution, cationic groups such as polylysine, polyornithine, polyhistidine and polyarginine and hydrophobic groups such as aromatic aminoacid containing peptides have been covalently linked to oligonucleotides. Peptide ligands targeting cellular receptors have been conjugated to oligonucleotides to enhance cellular permeation. Oligonucleotides have also been modified with peptides that are believed to function as synthetic nucleases.

In one particular study, the thermodynamic melting of a library containing peptide linked oligonucleotides was analyzed to explore the influence of various peptide side chains on the hybridization properties of the DNA (see: Frier, et al., *Nucleosides Nucleotides*, 1999, 18, 1477–1478; and Harrison, et al., *Nucleic Acids Res.*, 1998, 26, 3136–3145). An invariant 8-mer oligonucleotide was coupled to a five-residue variable peptide region composed of the cationic amino acids lysine, ornithine, histidine and arginine, the hydrophobic amino acid tryptophan, and alanine as a spacer. Melting temperature analysis indicated nearly 1° C. increase for each cationic residue present and Tm depended principally on the number of cationic residues. Thus the free energies of binding for polycationic peptide linked oligonucleotides were significantly enhanced compared with the unmodified 8-mer. The origin of this stabilizing effect was derived from a more exothermic enthalpic term. A study of pH dependence showed that the polyhistidine conjugate was particularly sensitive to pH changes near neutrality, as indicated by a significant rise in Tm from 19.5° C. at pH 8.0 to 28.5° C. at pH 6.0.

In another study, the hybridization properties of a series of oligomers, based on two different 9-mer oligodeoxynucleotide sequences with an appended oligoarginine chain (Rn) were investigated (see: Wei, et al., *Nucleic Acids Res.*, 1996, 24, 55–61). The oligomers were either peptide linked oligonucleotides or peptide-bridged oligonucleotide pairs (e.g., Rn-oligonucleotide or oligonucleotide-Rn-oligonucleotide). For the double-linked probes, it was found that the peptide bridge induces the two 9-mers to bind complementary single-stranded DNA or RNA targets with substantially enhanced thermal stability. Single or double-linked labeled oligomers complexed to complementary RNA were able to activate RNase H.

A synthetic 12-mer oligodeoxyribonucleotide has been coupled at its 5' terminus to a series of positively charged (δ-ornithine)$_n$-cysteine peptides (see: Zhu, et al., *Antisense Res. Dev.*, 1993, 3, 265–275). Site-directed cleavage with RNase H demonstrated that the peptide-modified oligomer hybridized with its RNA target sequence. Increased affinity for target mRNA was also observed.

Melting studies of the complex between an Ha-ras antisense oligonucleotide carrying nuclear localization peptide sequences (NLS) and target mRNA showed that the conjugated oligonucleotide formed a more stable duplex compared with unmodified oligonucleotides (see: Garcia de la Torre, et al., *Bioconjugate Chem.*, 1999, 10, 1005–1012). Despite the presence of the linked peptide, good mismatch discrimination was maintained when the conjugated oligonucleotide was bound to target RNA.

Fusogenic peptides belong to another family of peptides that has been studied in antisense applications. One such fusogenic peptide, derived from the influenza hemaglutinin envelope protein, has been conjugated to antisense oligonucleotides (see: Bongartz, et al., *Nucleic Acids Res.*, 1994, 22, 4681–8468). This peptide changes conformation at acidic pH and destabilizes the endosomal membrane resulting in an increased cytoplasmic delivery of the antisense oligonucleotide. The use of similar fusogenic peptides conjugated to an anti-TAT antisense oligodeoxynucleotide via a disulfide or thioether bond resulted in 5- to 10-fold improvement of the anti-HIV activity of the phosphodiester antisense oligonucleotide on de novo infected CEM-SS lymphocytes in serum-free media. No toxicities were observed at the effective doses (0.1–1 $\mu$M). However, no sequence specificity was observed and the fusogenic peptide possessed some antiviral activities on its own ($IC_{50}$=6 $\mu$M). A phosphorothioate (deoxycytidine)$_{28}$ (S-dC28) peptide conjugate and a streptavidin-peptide-biotinylated S-dC28 adduct showed activity similar to the unconjugated S-dC28 oligonucleotide ($IC_{50}$: 0.1–1 nM).

Enhanced cellular uptake of oligonucleotides by EGF-R-mediated endocytosis in epithelial cancer cells (A549 cells) has been demonstrated (see: Deshpande, et al., 1996, *Pharm. Res.*, 13, 57–61). To overcome the problem of endosomal entrapment associated with receptor-mediated delivery, the authors evaluated the effects of two fusogenic peptides, polymyxin B and influenza HA2 peptide, for their capability to promote cytoplasmic delivery of oligonucleotides. A conjugate consisting of EGF and poly-L-lysine (PL) was synthesized and complexed with 5' fluorescently-labeled oligonucleotide. Cellular uptake of this complex in the presence or absence of the fusogenic peptides was monitored fluorometrically and intracellular distribution of the oligonucleotide was determined. Cells treated with the complex exhibited significantly enhanced intracellular fluorescence over controls treated with oligonucleotide alone. Microscopic fluorescence studies revealed, however, that the complex accumulated in endocytic vesicles. Exposure of the cells to the complex in the presence of HA2 peptide and polymyxin B resulted in a more diffused intracellular fluorescence pattern and an increase in fluorescence intensity. These results are consistent with the known fusion and destabilizing activities of the peptides. The uptake of the complex was shown to occur via the EGF receptor-mediated pathway. Since EGF receptors are overexpressed in many cancer cell types, the EGF-PL conjugate may potentially be used as an effective and selective delivery system to enhance uptake of oligonucleotides into cancer cells.

Another approach to the intracellular delivery of oligonucleotides is based on the use of several types of "delivery peptides" that seem to have the ability to carry large, polar molecules including peptides, oligonucleotides, and even proteins across cell membranes (see: Schwarze, et al., *Trends Cell Biol.*, 2000, 10, 290–295; and Schwarze, et al., *Science* (Washington, D.C.), 1999, 285, 1569–1572). Two examples of delivery peptides are a 35-amino-acid sequence ("Tat") from the HIV Tat protein, and a 16-amino-acid sequence ("Ant") from the Drosophila Antennapedia protein. Antennapedia-type peptides have been used to deliver oligonucleotides, including PNAs, into neuronal cells, but their general applicability is yet to be completely studied. Other types of peptides, containing hydrophobic motifs and special recognition motifs, have also been used for antisense delivery.

Ant and Tat peptide-oligonucleotide conjugates have been prepared for the MDR-1 system (see: Astriab-Fisher, et al., Biochem. Pharmacol., 2000, 60, 83–90). The phosphorothioate oligonucleotide component of the conjugates was complementary to a site flanking the AUG of the message for P-glycoprotein, a membrane ATPase associated with multidrug resistance in tumor cells. Both types of peptide-antisense oligonucleotide conjugates, but not mismatched control conjugates, provided substantial inhibition (34%) of cell-surface expression of P-glycoprotein at submicromolar concentrations. The peptide-oligonucleotide conjugates were more potent in the presence of serum than when used under serum-free conditions which is in contrast to cationic lipid-based approaches for intracellular delivery of nucleic acids. Flow cytometry profiles indicated the conjugates accumulated in cells to a much greater degree than the free oligonucleotides. The conjugates reached the nucleus while the free oligonucleotides had virtually no intracellular fluorescence.

Nuclear delivery of antisense oligodeoxynucleotides and selective inhibition of cholesteryl ester transfer protein (CETP) expression by an antisense oligonucleotide complexed to N,N-dipalmitylglycyl-apo E peptide has been shown in a Chinese hamster ovary (CHO) cell line. The cells were stably tranfected with human CETP (Liu, et al., Arterioscler. Throm. Vasc. Biol., 1999, 19, 2207–2213). N,N-Dipalmitylglycyl-apolipoprotein E (129–169) peptide (dpGapoE) has been shown to be an efficient gene delivery system for both plasmids and antisense oligodeoxynucleotides. dpGapoE contains the minimum determinants for binding to both lipid surfaces and the LDL receptor. Thus, dpGapoE could be used to target oligonucleotides to liver. After transfection of oligodeoxynucleotides by dpGapoE, translocation of oligonucleotide to the nuclei and concentration in nuclear structures was observed in >95% of the cells at 6 and 12 hours by fluorescence microscopy with oligonucleotide observed for >48 hours. No membrane disruption was observed after transfection. Cellular CETP mRNA levels gradually declined, and the maximum reduction in the mRNA level (>50%) was observed at 36 hours, after which the mRNA level started to recover. CETP activity in the culture medium declined over 72 hours, with maximum reduction observed at 36 hours (54% of control). Neither CETP mRNA levels nor CETP activity changed after the transfection of sense phosphorothioate oligodeoxynucleotides delivered by dpGapoE complex or naked antisense oligodeoxynucleotides. This is the first demonstration of the use of an LDL receptor-binding peptide for the delivery of antisense oligonucleotides. This approach may enable gene regulation in vivo and development of antiatherosclerotic agents to alter high-density lipoprotein metabolism.

Eighteen conjugates of phosphorothioate oligonucleotides to membrane translocation and nuclear localization peptides were prepared in good yield and were thoroughly characterized with electrospray ionization mass spectra (see: Antopolsky, et al., Bioconjugate Chem., 1999, 10, 598–606). When applied to cells, conjugates exhibiting membrane translocation and nuclear localization properties displayed efficient intracellular penetration but failed to show improved antisense effects. Studies on the intracellular distribution of the fluorescein-labeled conjugates revealed that the conjugates were trapped in endosomes.

It has been demonstrated that conjugates of transporter peptides to PNA show improved delivery and are able to regulate galanin receptor levels and modify pain transmission in vivo (see: International Patent Application PCT/US99/05302, filed Jul. 16, 1999; Pooga, et al., Nat. Biotechnol., 1998, 16, 857–861; and Villa, et al., FEBS Lett., 2000, 473, 241–248). A PNA antisense 21-mer to the human type 1 galanin receptor was linked via a labile cysteine disulfide bond to biotin-labeled peptides known to impart cell membrane permeant properties. These peptides were transportan (galanin (1–12)-Lys-mastoparan (1–14)amide) and pAntennapedia (pAntp (43–58), the third helix of Atennapedia homeodomain). The resulting conjugates improved internalization and down-regulated the human galanin receptor in Bowes cell line and in rat spinal cord in vivo. The intrathecal administration of the peptide-PNA construct resulted in a decrease in galanin binding in the dorsal horn. Due to decreased binding, galanin could not inhibit the C fibers stimulation-induced facilitation of the rat flexor reflex, demonstrating that peptide-PNA constructs acted in vivo to suppress expression of functional galanin receptors. These peptides have been demonstrated to translocate across the plasma membrane of eukaryotic cells by an energy-independent pathway (see: Lindgren, et al., Trends Pharmacol. Sci., 2000, 21, 99–103.).

Nine different peptides containing a hydrophobic motif associated with a nuclear localization signal (Chaloin, L., Vidal, P. Lory, P. Mery, J. Lautredou, N. Divita, G., and Heitz, F. Design of carrier peptide-oligonucleotide conjugates with rapid membrane translocation and nuclear localization properties derived from SV40 antigen T separated by various linkers have been synthesized on solid phase (see: Chaloin, et al., Biochein. Biophys. Res. Commun., 1998, 243, 601–608.) The hydrophobic sequence corresponded either to a signal peptide sequence of Caiman crocodylus or to a fragment of the fusion peptide of gp41N, while the hydrophilic sequence was that of a nuclear localization signal. The C-termini of these peptides bear a cysteamide group linked to a fluorescent probe to allow the cellular localization to be determined. The peptide conjugate was successfully synthesized using a disulfide bridge and then used to target fluorescently tagged phosphorothioate oligodeoxynucleotides into fibroblasts. The presence of a linker appears to play a role in the cellular localization. In a 5 minute incubation time more than 90% cells were targeted. It appeared that the membrane-associated conformational state of the peptides was crucial for the internalization process and endocytosis can be ruled out since no temperature (4 or 37° C.) effect on the internalization was observed.

The signal peptide (SEQ ID No. 11) should be able to convey oligonucleotides to the endoplasmic reticulum and from there to the cytosol and the nucleus where their targets are located (see: Arar, et al., Bioconjugate Chem., 1995, 6, 573–577.) A 5',3'-modified pentacosanucleotide, complementary to the translation initiation region of the gag mRNA of HIV, was coupled to a (bromoacetyl)dodecapeptide containing a KDEL signal sequence. The anti-HIV activity of the pentacosanucleotide was compared with that of pentacosanucleotide-dodecapeptide conjugates linked through either a thioether bond or a disulfide bridge. The conjugate with a thioether bond was shown to have a higher antiviral activity than the peptide-free oligonucleotide or the conjugate linked via a disulfide bond.

In another approach, an oligonucleotide-Tat peptide conjugate, having dual binding capability for a designated RNA, was designed (see: Tung, et al., *Bioconjugate Chemistry* 1995, 6, 292–295.) The peptide portion of the conjugate interacts with a folded domain in the RNA, whereas the oligonucleotide portion hybridizes with a nearby single-stranded region in the RNA. The dual specificity was proven in a model HIV-1 TAR RNA system using an RNase H cleavage assay to assess antisense binding to this RNA. The peptide portion of the conjugate was shown to confer increased specificity on the oligonucleotide.

Antisense oligonucleotides, targeting human immunodeficiency virus type 1 (HIV), have been linked to fusion peptides derived from the HIV transmembrane glycoprotein gp41 (see: Soukchareun, et al., *Bioconjugate Chem.,* 1995, 6, 43–53.) Thermal denaturation studies showed that the interaction of the conjugate with its complementary strand was similar to that of unmodified oligonucleotides. Thus in this example, the peptide does not confer additional stability to the oligonucleotide-mRNA complex.

A number of methods have been used to synthesize and purify oligonucleotide-peptide conjugates. One method has been developed to fragment couple pre-synthesized peptides to the 2'-position of a selected nucleotide within an otherwise protected oligonucleotide chain attached to a solid support (see: Zubin, et al., *FEBS Lett.,* 1999, 456, 59–62.) Synthesis of nucleopeptide-oligonucleotide conjugates has been carried out on δ-ornithine peptides by modification of the a-amino ornithine functional group with pyrimidyl-1- and purinyl-9-acetic acids or with pyrimidyl-1-and purinyl-9-alanines (see: Sumbatyan, et al., *Nucleosides Nucleotides,* 1999, 18, 1489–1490.) Nucleopeptides have also been prepared on a solid polymer bearing a photo-activatable linker. Conjugates with the 16-mer oligonucleotide complementary to the env AUG codon region of the Friend murine leukemia virus were prepared in this manner.

Solid-phase synthesis of several peptide-oligonucleotide conjugates has been achieved using a peptide-fragment coupling strategy on a controlled pore glass support (see: Peyrottes, et al., *Tetrahedron,* 1998, 54, 12513–12522; Peyrottes, et al., *Nucleosides Nucleotides,* 1999, 18, 1443–1448.) The conjugates contained either a hydrophobic tetrapeptide (Leu-Gly-Ile-Gly) (SEQ ID NO: 18) or an 8-residue basic peptide of the HIV-1 Tat protein coupled to one of two oligodeoxyribonucleotides (an oligoribonucleotide or a mixed ribo/2'-O-Me oligonucleotide). Improved yields were obtained when internucleotide β-cyanoethyl groups were removed from the support-bound oligonucleotide prior to peptide-fragment coupling, and by use of a long alkyl spacer in the linkage between peptide and oligonucleotide.

Another study describes synthesis of DNA-peptide conjugate molecules on oxime resin (see: Fujii, et al., *Pept. Sci.,* 1999, 35, 293–296.) The oligonucleotide and peptide are covalently linked by cleaving the DNA fragment synthesized on modified oxime resin in the presence of independently prepared peptide fragment bearing free terminal α-amino group and protected side chain residues. This method affords DNA conjugate molecules in moderate to good yields. A different solid-phase synthesis of oligonucleotides conjugated at the 3'termini to a peptide has been developed (see: De Napoli, et al., *Bioorg. Med. Chem.,* 1999, 7, 395–400). A 17-mer antisense oligonucleotide against HIV-1, linked at the 3'-terminus to the tripeptide Gly-Gly-His, was prepared in good yields and characterized by MALDI-TOF mass spectrometry.

A highly basic peptide (net charge +8) derived from the HIV-1 Tat protein was conjugated with quantitative yield to a 19-mer rhodamine-labeled phosphodiester oligonucleotide activated by the pyridinesulfenyl group (see: Vives, et al., *Tetrahedron Lett.,* 1997, 38, 1183–1186.) To avoid precipitation due to antagonist charges of the oligonucleotide and the peptide, the conjugation was performed in high salt concentration (400 mM) and acetonitrile (40%).

Synthesis and characterization of very short peptide-oligonucleotide conjugates and stepwise solid-phase synthesis of peptide-oligonucleotide conjugates on new solid supports have been described (see: Bongardt, et al., *Innovation Perspect. Solid Phase Synth. Comb. Libr., Collect. Pap., Int. Symp., 5th,* 1999, 267–270; Antopolsky, et al., *Helv. Chim. Acta,* 1999, 82, 2130–2140). These supports are designed to link the 3'-terminus of an oligonucleotide to the C-terminal end of a peptide via a phosphodiester or phosphorothioate bond in the process of stepwise solid-phase assembly.

Oligonucleotide-peptide complexes offer another non-RNase H mechanism of sequence-specific, hydrolytic cleavage of mRNA. Oligonucleoitde-peptide conjugates designed for mRNA cleavage have been obtained using several methods. By appending a maleimide group to an oligonucleotide, selective coupling to the thiol side chain of a cysteine residue in a peptide has been performed in 53% overall yield (see: Tung, et al., *Bioconjugate Chem.,* 1991, 2, 464–5). Two oligonucleotide conjugates with peptide moieties that either mimic the active site of RNase A (HGH motif) or that contain a Cu(II) completing metallopeptide (GGH motif) have been synthesized by solid phase synthesis methods with pentafluorophenyl active esters of amino acids and Boc-His(Tos)-OH (see: Truffert, et al., *Tetrahedron,* 1996, 52, 3005–16.).

Highly efficient endonucleolytic cleavage of single-stranded RNA by a 30-amino acid zinc-finger peptide has been reported (see: Lima, et al., *Proc. Natl. Acad. Sci. U.S.A.,* 1999, 96, 10010–10015.) The peptide sequence corresponds to a single zinc finger of the human male-associated ZFY protein, a transcription factor belonging to the $Cys_2His_2$ family of zinc-finger proteins. Interestingly, RNA cleavage was observed only in the absence of zinc. Coordination with zinc resulted in complete loss of RNase activity. The active structure was found to be a homodimeric form of the peptide. Dimerization occurred through a single intermolecular disulfide between two of the four cystines. The catalytic activity was single-stranded RNA-specific; single-stranded DNA, double-stranded RNA and DNA, and 2'—O-methoxy-modified oligonucleotides were not degraded by the peptide. The peptide specifically cleaved after pyrimidines with a preference for the dinucleotide sequence 5'-pyr-A-3'. The RNA cleavage products consisted of a 3' phosphate and 5' hydroxyl. The initial rates of cleavage ($V_0$) observed for the finger peptide were comparable to rates observed for human RNases, and the catalytic rate ($K_{cat}$) was comparable to rates observed for the group II intron ribozymes. The pH profile exhibited by the peptide is characteristic of general acid-base catalytic mechanisms observed with other RNases. Different chemical methods have been proposed to conjugate this peptide to antisense oligonucleotides (see: International Patent Application PCT/US99/23273, filed Oct. 6, 1999.).

Design of a synthetic nuclease using a zinc-binding peptide tethered to a rhodium intercalator can hydrolyze DNA (see: Fitzsimons, M. P., and Barton, J. K. Design of a Synthetic Nuclease: DNA Hydrolysis by a Zinc-Binding Peptide Tethered to a Rhodium Intercalator, in *J. Am. Chem. Soc.,* 1997, 119, 3379–3380.) A 16 amino acid peptide, DPDGLGHAAKHEAAAK (SEQ ID NO: 19) which binds stoichiometric zinc ion, has been tethered to the DNAintercalating metal complex Rh(phi)$_2$ bpy' (phi=phenanthrenequinone diimine, bpy'=4-butyric acid-4-methyl-2,2'-bipyridine) to construct a synthetic DNase. In this combination of DNA-binding and reactive moieties, the rhodium intercalator delivers the appended peptide for reaction with DNA. In the presence of Zn$^{2-}$, the Rh(phi)$_2$ bpy'-peptide conjugate at $\mu$M concentration cleaves supercoiled pBR322 DNA and a 17-base pair oligonucleotide duplex under mild conditions. The rate constant for the cleavage of pBR322 DNA by Rh(phi)$_2$ bpy'-peptide at pH 6.0 is $2.5\pm0.2 \ 10^{-5} \ s^{-1}$. Product analysis of cleaved oligonucleotide fragments shows 3'-hydroxyl termini exclusively. These results demonstrate a stereospecific, hydrolytic DNA cleavage reaction by a synthetic complex. Similar experiments with RNA have not been reported.

Systematic studies of the sequence and the structural requirements for good cell penetration and compartmentalization in a range of cell lines as well as correlation with biological activity have not yet been reported for peptide-oligonucleotide conjugates. This is because such studies have been hampered by the often cumbersome and inefficient methods required for the chemical synthesis of such bioconjugates (see: Stetsenko, et al., *J. Org. Chem.*, 2000, 65, 4900–4908). Current synthetic procedures for making peptide linked oligomeric compounds, especially those derived from the cationic peptides, are problematic due aggregation complications associated with electrostatic interactions. Additionally, current methods require excess peptide reagents which render these syntheses difficult, labor-intensive, and economically unfeasible.

Thus, there is a need in the art for cost-effective and efficient methods for the large scale synthesis of peptide linked oligomeric compounds.

SUMMARY OF THE INVENTION

The present invention provides methods useful for the preparation of peptide linked oligomeric compounds. The process comprises the steps of:

(a) providing a support medium derivatized with a compound wherein each compound comprises a protected hydroxyl group;

(b) treating the protected hydroxyl group with a deprotecting reagent effective to deprotect the hydroxyl group;

(c) reacting the deprotected hydroxyl group with a nucleoside having a protected hydroxyl group and an activated phosphorus containing substituent group thereby forming an extended compound;

(d) optionally treating the extended compound with a capping agent to form a capped compound;

(e) optionally repeating steps (b), (c) and (d) to form a further extended compound;

(f) treating the capped compound or the further extended compound with an oxidizing reagent thereby forming an oxidized compound comprising one or more nucleosides;

(g) repeating steps (b), (c), (d), (e) and (f) for oxidized compounds comprising one nucleoside or optionally repeating steps (b), (c), (d), (e) and (f) for oxidized compounds comprising more than one nucleoside to give a further oxidized compound;

(h) cleaving the oxidized compound or the further oxidized compound from the support medium to give the oligomeric compound comprising a linking moiety.

(i) treating the linking moiety attached to the oligomeric compound with a reagent effective to form a reactive sulfur moiety on the linking moiety; and (j) reacting the reactive sulfur moiety with a peptide the peptide functionalized with a functional group reactive with the sulfur moiety thereby forming the peptide linked oligomeric compound.

In preferred embodiments the nucleoside is a 2'-, 3'-, or 5'-phosphoramidite or a 2'-, 3'-, or 5'-H-phosphonate.

In another preferred embodiment the activated phosphorus containing substituent group is a phosphoramidite, H-phosphonate, phosphate triester or a chiral auxiliary.

In one embodiment, one of either the reactive sulfur moiety or the functional group is —SH and the other of the reactive sulfur moiety or functional group is a disulfide group.

In a preferred embodiment the derivatized support medium is 3'-thiol-modifier C3 S—S CPG (DMT-O—(CH$_2$)$_3$—S—S—(CH$_{23}$—O-succinyl-LCAA-CPG).

In one embodiment, hydroxyl protecting groups are acid labile. Preferred hydroxyl protecting groups are trityl, monomethoxytrityl, dimethoxytrityl, trimethoxytrityl, 9-phenylxanthin-9-yl (Pixyl) and 9-(p-methoxyphenyl) xanthin-9-yl (MOX). These protecting groups are removed by treatment with weak acid preferably dichloroacetic acid or trichloroacetic acid.

In one embodiment, the capping agent comprises 20% acetic anhydride in acetonitrile mixed with about an equal volume of a solution having 20% N-methylimidazole, 30% pyridine and 50% acetonitrile.

In one embodiment, the cleaving step is performed using aqueous ammonium hydroxide. In another embodiment, the cleaving is performed using a bifunctional compound having an internal disulfide group. A preferred bifunctional compound has the formula H$_2$N—(CH$_2$)$_2$—S—S—(CH$_2$)$_2$—NH$_2$.

In one embodiment, the oligomeric compounds of the invention have from about 5 to about 50 nucleosides, with from about 8 to about 30 nucleosides preferred and from about 15 to about 25 nucleosides more preferred.

In another embodiment, methods are provided for preparing a peptide linked oligomeric compound having one of the formulas:

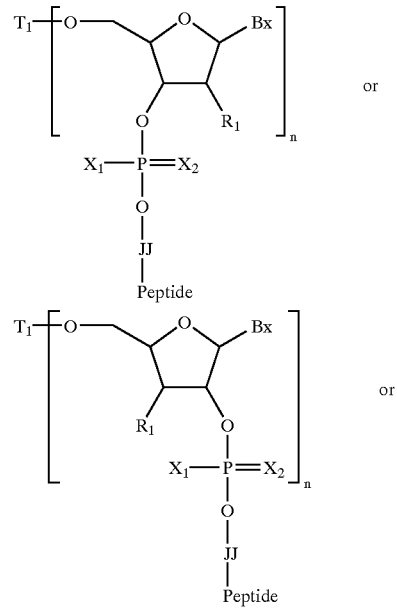

-continued

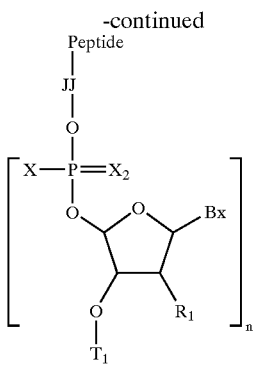

wherein $T_1$ is hydrogen or a hydroxyl protecting group;

each $X_2$ is, independently, O or S;

each $X_1$ is, independently, O, Pg-O—, S, Pg-S—, $C_1$-$C_{10}$ straight or branched chain alkyl, $CH_3(CH_2)_g$—O—, $R_2R_3N$— or a group remaining from coupling a chiral auxiliary;

g is from 0 to 10;

Pg is $CH_3$, —$CH_2CH_2CN$, —C ($CH_3$) ($CH_3$)—$CCl_3$,—$CH_2$—$CCl_3$, —$CH_2CH$=$CH_2$, $CH_2CH_2SiCH_3$, 2-yl-ethyl phenylsulfonate, δ-cyanobutenyl, cyano p-xylyl, diphenylsilylethyl, 4-nitro-2-yl-ethylbenzene, 2-yl-ethyl-methyl sulfonate, methyl-N-trifluoroacetyl ethyl, acetoxy phenoxy ethyl, or a blocking group;

each $R_2$ and $R_3$ is, independently, hydrogen, $C_1$-$C_{10}$ alkyl, cycloalkyl or aryl;

or optionally, $R_2$ and $R_3$, together with the nitrogen atom to which they are attached form a cyclic moiety;

each Bx is, independently, a heterocyclic base moiety;

each $R_1$ is, independently, H, a blocked hydroxyl group, or a sugar substituent group;

n is from 2 to about 50; and

JJ has one of the formulas;

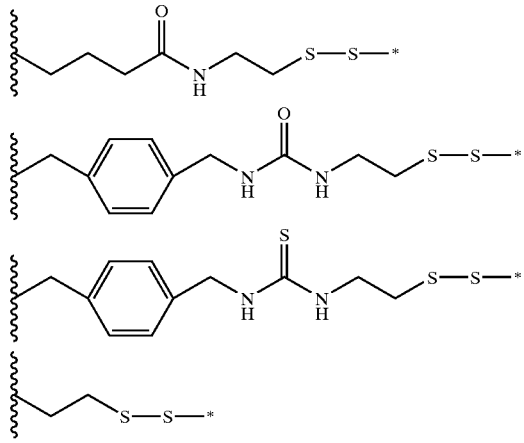

or wherein * denotes the point of attachment to the peptide;

comprising the steps of:

providing an oligomeric compound of the formula:

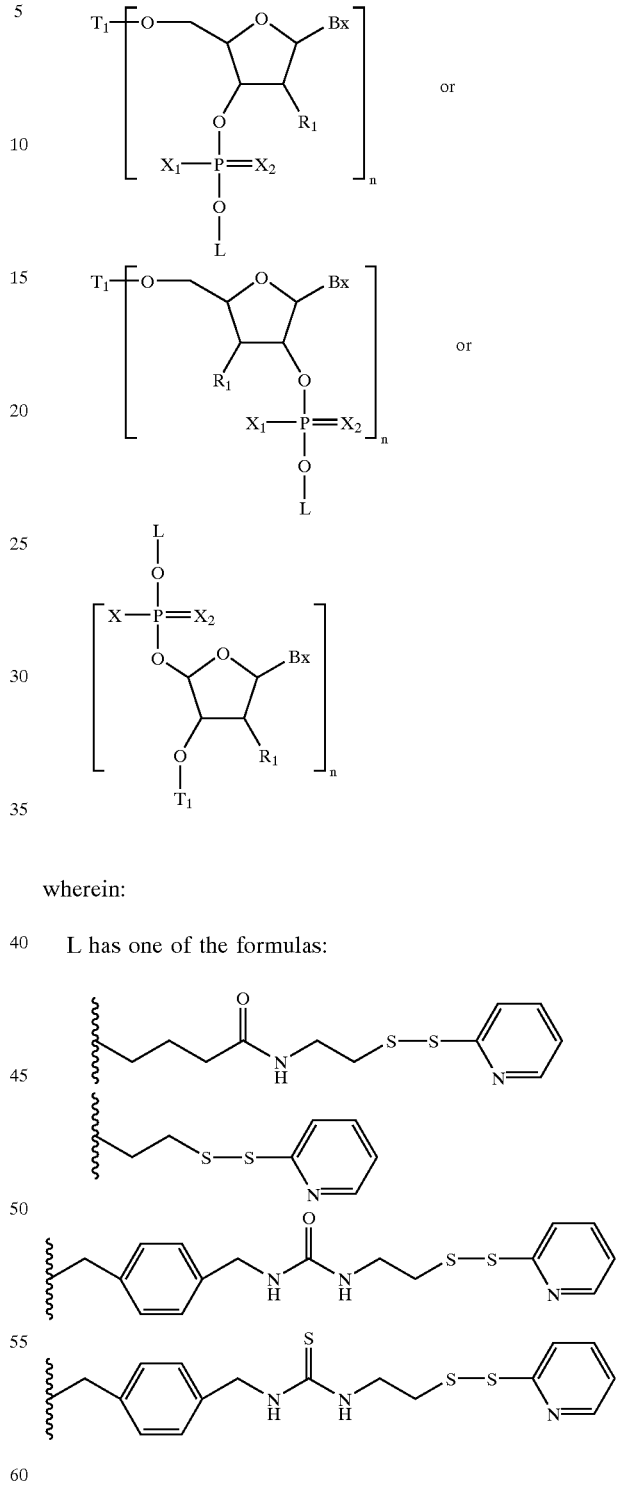

wherein:

L has one of the formulas:

reacting said oligomeric compound with a peptide having a —SH functional group thereby forming said peptide linked oligomeric compound.

In some embodiments, peptide linked oligomeric compounds have one of the formulas:

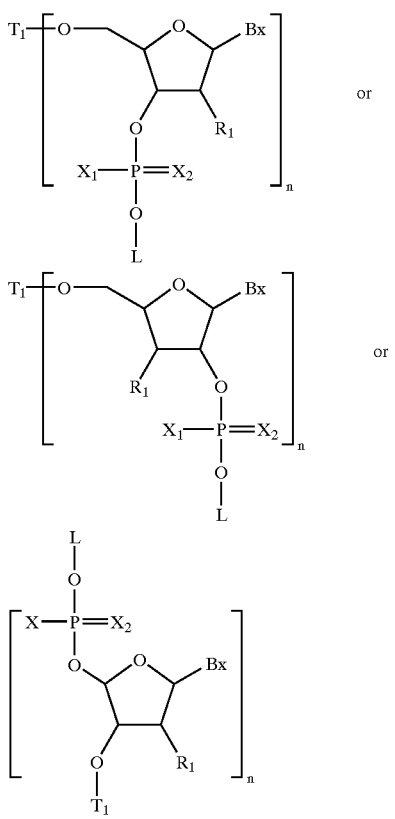

wherein
T₁ is hydrogen or a hydroxyl protecting group;
J is $C_1$–$C_{12}$ alkyl or —$(CH_2)_m$—G—$(CH_2)_m$—;
G is O, S, —NH—C(O)—, —NH—C(O)—NH—, —NH—O—, or —NH—C(O)—O—;
m is from 2 to about 12;
each $X_2$ is, independently, O or S;
each $X_1$ is, independently, Pg—O—, Pg—S—, $C_1$–$C_{10}$ straight or branched chain alkyl, $CH_3$ $(CH_2)_g$—O—, $R_2R_3N$— or a group remaining from coupling a chiral auxiliary;
g is from 0 to 10;
Pg is $CH_3$, —$CH_2CH_2CN$, —$C(CH_3)$ $(CH_3)$-$CCl_3$, —$CH_2$—$CCl_3$, —$CH_2CH$=$CH_2$, $CH_2CH_2SiCH_3$, 2-yl-ethyl phenylsulfonate, 5-cyanobutenyl, cyano p-xylyl, diphenylsilylethyl, 4-nitro-2-yl-ethylbenzene, 2-yl-ethyl-methyl sulfonate, methyl-N-trifluoroacetyl ethyl, acetoxy phenoxy ethyl, or a blocking group;
each $R_2$ and $R_3$ is, independently, hydrogen, $C_1$–$C_{10}$ alkyl, cycloalkyl or aryl;
or optionally, $R_2$ and $R_3$, together with the nitrogen atom to which they are attached form a cyclic moiety;
each Bx is, independently, a heterocyclic base moiety; and
each $R_1$ is, independently, H, a blocked hydroxyl group, or a sugar substituent group;
n is from 2 to about 50; and
nn is from 2 to about 10.

DESCRIPTION OF PREFERRED EMBODIMENTS

Figure 1:
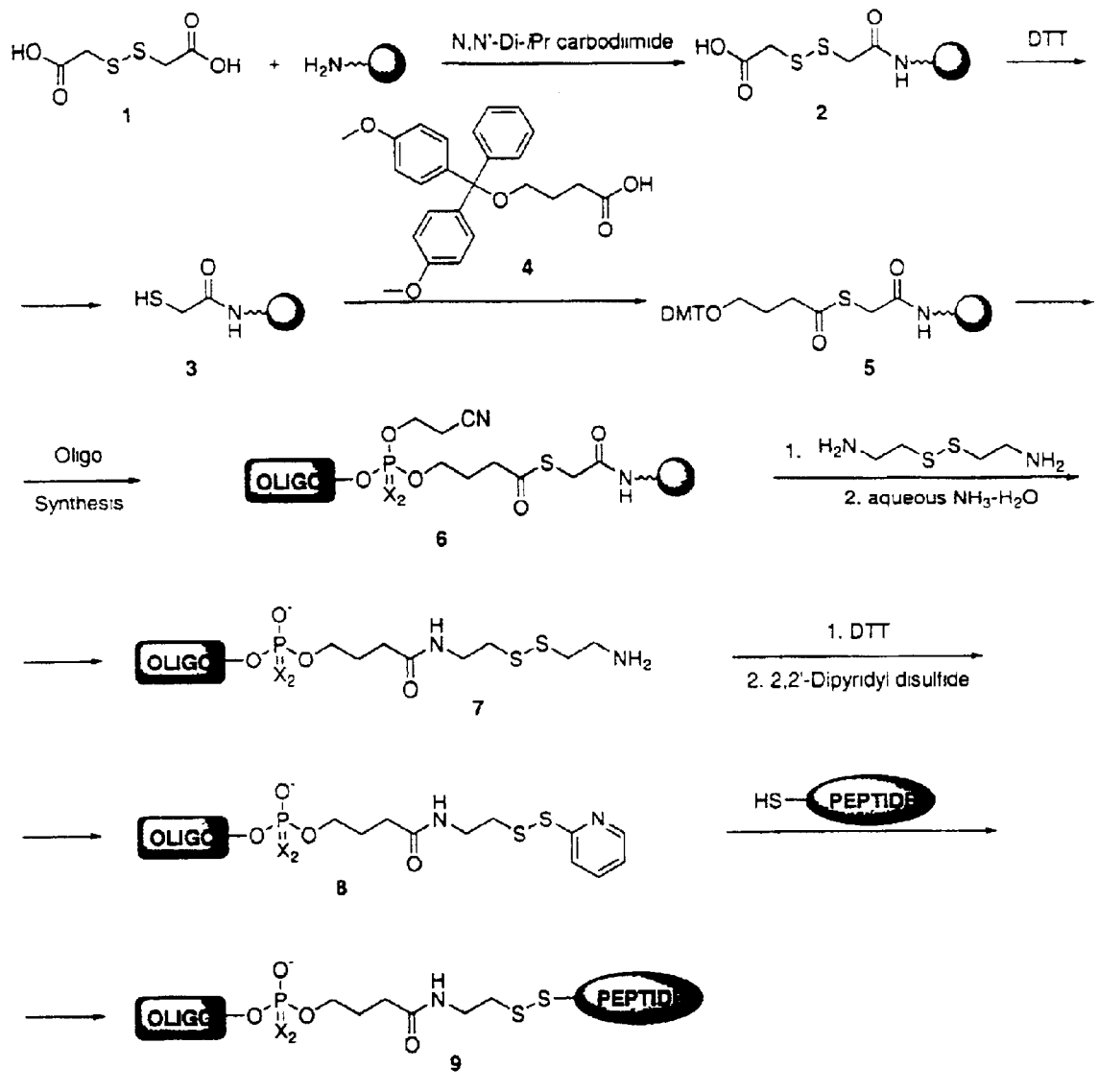
FIG. 1 is a flow scheme showing synthesis of a peptide linked olignucleotide having disulfide and amide functional groups in the linkage.
Figure 2:
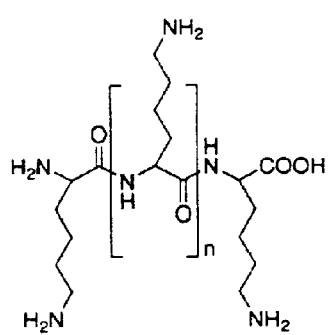
FIG. 2 is a formula of a representative cationic peptide.
Figure 2:
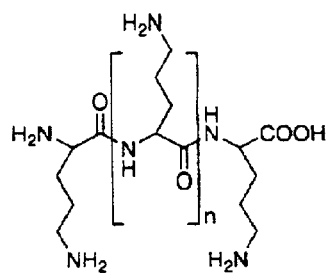
Figure 2:
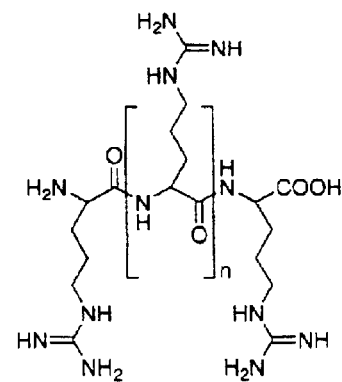
Figure 3:
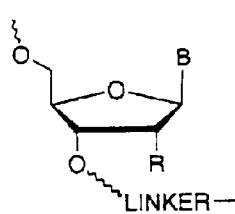
FIG. 3 is a formula of a specific peptide linked oligomeric compound where the peptide is defined (Antennapedia (SEQ ID NO: 7) and TAT (SEQ ID NO: 20) peptides).
Figure 3:
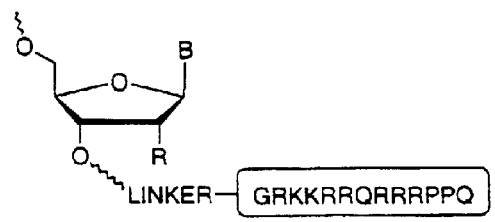

The present invention is directed to methods for preparing peptide linked oligomeric compounds. The methods of the present invention provide improved synthetic schemes which avoid the problems of the prior art, such as those encountered during synthesis of cationic peptides, e.g., complications due to the aggregation problems associated with electrostatic interactions and the problems generated by use of excess peptide reagents used in the procedures known heretofore.

The synthetic methods of the present invention employ equimolar amounts of functionalized oligomeric compounds and peptide reagents, which has successfully resulted in the large scale synthesis, i.e., 2500 OD (100 mg) scale- of an antennapedia peptide linked to a MOE gapmer oligomeric compound having SEQ ID No 1.- This scaled-up synthesis is significantly larger than any synthesis previously reported in the literature.

In one aspect of the present invention an oligomeric compound is prepared having a functional group attached through a phosphorous substituent group to a 2'-, 3'- or 5'-O-position of a terminal nucleoside. This functional group is further treated with one or more reagents to form an activated functional group which is capable of forming a disulfide linkage with a thiolated peptide. One example of this activation is shown below:

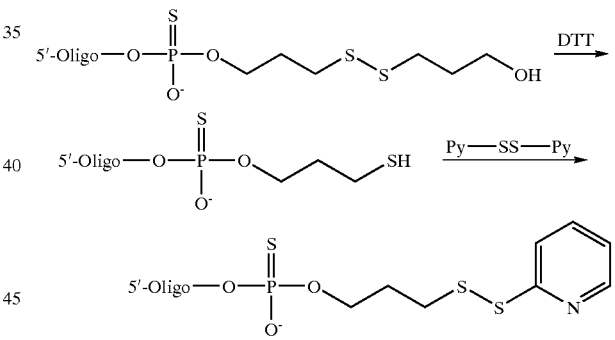

Here a 3'-terminal phosphorothioate oligomeric compound is prepared using support methodologies and cleaved. The disulfide bridge present is converted into a more reactive disulfide bridge by treatment with DTT followed by treatment with 2,2'-dithiodipyridine. This method converts the oligomeric compound to a reactive species able to form a disulfide bridge with a thiolated peptide. The final compound from this sequence will have the formula:

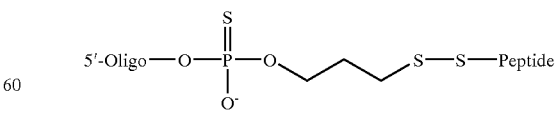

The method is particularly useful for the formation of peptide linked oligomeric compounds giving high purity product in high yields. The use of equimolar amounts of reactants as opposed to using an excess of peptide reagent lowers the cost of synthesis and greatly simplifies the purification process. This activation process can be used to form variable linkages between the oligomeric compound and the peptide. The process is also amenable to all types of oligomeric compounds. The terminal phosphorus species is also variable.

A representative list of functional groups that are activated and used to link thiolated peptides to oligomeric compounds are shown below:

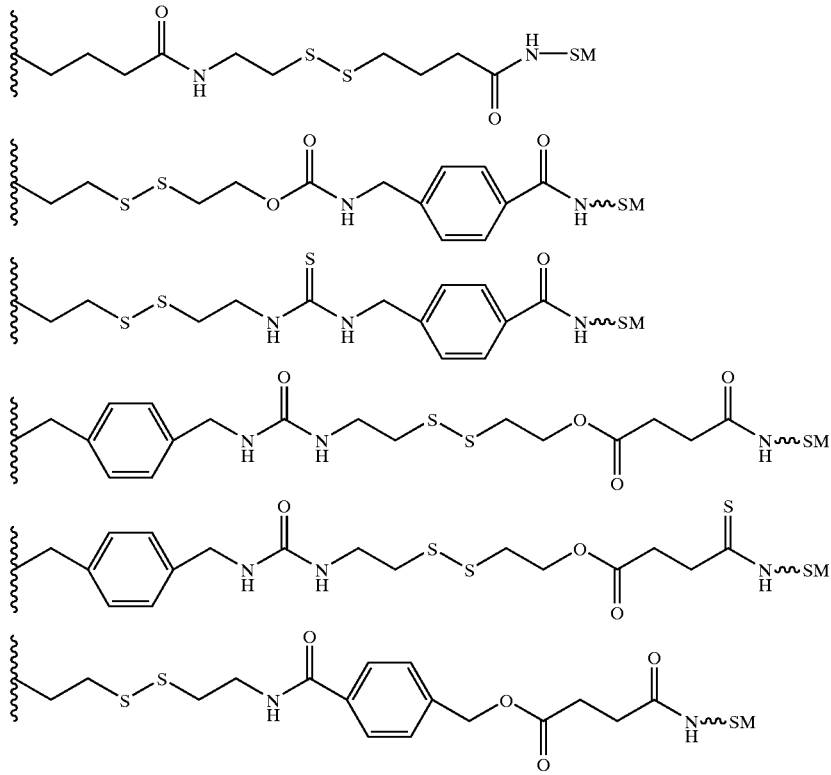

Where the left side of the functional group is linked to an oligomeric compound through a phosphorus substituent group and SM is a support medium.

The support bound oligomeric compounds can be cleaved from the support medium using standard methodologies or can be treated with a compound that cleaves the functional group at some point. In one aspect of the invention the functional group is treated with DTT followed by 2,2'-dithiodipyridine to activate the disulfide group. The oligomeric compound having an activated disulfide group is reacted in about equimolar amounts with a thiolated peptide to give the final peptide linked oligomeric compound.

The above representative functional groups will yield final products as shown below:

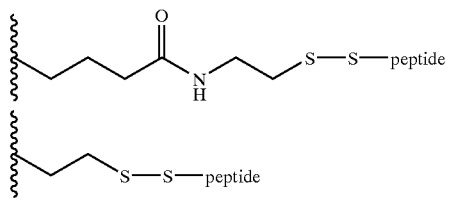

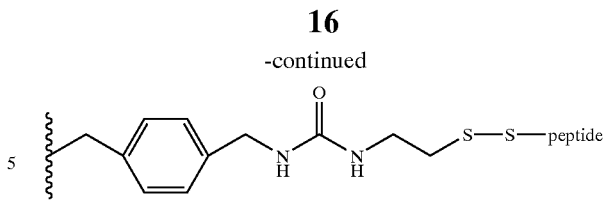

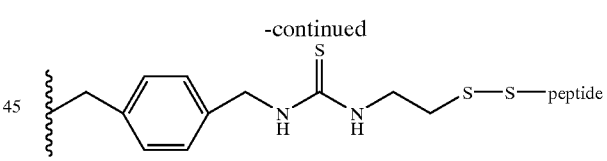

In an alternate approach the thiol group attached to the peptide can be activated with DTT/2,2'-dithiodipyridine and reacted with the oligomeric compound having a terminal thiol group as shown above after reacion with DTT.

Peptides are thiolated by incorporating a cysteine group or can be thiolated synthetically (see Example 20).

In one aspect of the present invention, a support medium is derivatized with a compound having a protected hydroxyl group. This hydroxyl group is deprotected and reacted with a nucleoside having an activated phosphorus-containing substituent group located at a 2'-, 3'- or 5'-position to form an extended compound. The extended compound could be further reacted with another nucleoside having an activated phosphorus containing substituent group thereby forming a further extended compound. Alternatively, the deprotected hydroxyl group could be reacted with an oligomeric compound having an activated phosphorus-containing substituent group located at a terminal 2'-, 3'- or 5'-position to form a further extended compound.

After completion of the synthesis, the extended compound or further extended compound from the support medium by cleaving at the site of attachment of the compound to the medium. Thus, the compound initially attached to the support media remains with the oligomeric compound and preferably contains a disulfide bridge. The disulfide bridge can be present initially or can be created during the cleaving reaction. The disulfide bridge is activated with a reagent such as DTT and further reacted with a thiol group attached to a peptide thus forming the peptide linked oligomeric compound.

In one aspect of the present invention, the disulfide bridge is formed by treatment of the support bound oligomeric compound with a cleaving agent that leaves the disulfide bridge behind. Such a reaction scheme is shown in FIG. 1. Here an oligomeric compound attached to a support medium through an amide containing compound is treated with a disulfide compound to give the desired disulfide bridge. The disulfide bridge is further treated with DTT to activate it towards reaction with a thiol group. This activated disulfide is reacted with a thiol group attached to a peptide thus forming the peptide linked oligomeric compound.

Oxidizing reagents that are effective to transfer an oxygen atom (thereby converting a $p^{III}$ linkage to a $p^V$ linkage) include without limitation m-chloroperbenzoic acid; iodobenzene diacetate, tetra-n-butylammonium periodate; tert-butyl hydroperoxide; di-tert-butyl hydroperoxide; cumene hydroperoxide; hydrogen peroxide; bis-trimethylsilyl peroxide; and catalytic amounts of trimethylsilyl triflate; dinitrogen tetroxide and molecular oxygen in the presence of 2,2'-azobis(2-methylpropionitrile) under thermal or photochemical conditions; and (1S)-(+)-(10-camphorsulfonyl)-oxaziridine; iodine/tetrahydrofuran/water/pyridine; hydrogen peroxide/water; tert-butyl hydroperoxide; and a peracid like m-chloroperbenzoic acid (see review article Beaucage et al., *Current Protocols in Nucleic Acid Chemistry*, 2000, 3.3.1-3.3.20). In the case of oxidation to a sulfur species (sulfurization), the reaction is generally performed under anhydrous conditions with the exclusion of air or oxygen. In the case of oxidation the reaction can be performed under aqueous conditions.

Oxidizing reagents that transfer a sulfur atom (sulfurizing reagents) are used to form phosphorothioate or other sulfurized internucleoside linkages such as, for example, phosphorodithioate internucleoside linkages. Sulfurizing reagents amenable to the present invention include those that are partially or completely soluble in a selected capping reagent or reagents. In addition, the sulfurizing reagent should be compatible, i.e., stable and non-reactive with the capping reagents. Preferred sulfurizing reagents are commercially available in bulk for considerably less cost than most traditional sulfurizing agents that are currently in use. Alternatively, a sulfurizing reagent is selected because of its ease of synthesis from inexpensive bulk reagents.

One important criteria for a preferred sulfurizing reagent is its ability incorporate sulfur and exclude incorporation of oxygen. Analysis of an oxidized oligomer, using $^{31}$P NMR, will give the percentages of sulfurized and oxygenized internucleoside linkages.

Sulfurized internucleoside linkages amenable to the present invention include those that are prepared by methods known in the art to give chirally enhanced or chirally pure sulfurized linkages for those linkages that are not achiral. Preferred sulfurized linkages that are prepared by the present methods include:

phosphorothioate (—O—P(S)(O)—O—);
phosphorodithioate (—O—P(S)(S)—O—);
phosphorthioamidate (—O—P(S) (NJ$_n$)—O—);
phosphonothioate (—O—P (J$_n$) (S)—O—);
boranothiophosphate (—O—P(S) (BJ3)-J$_n$-);

wherein "J$_n$," denotes a substituent group which is commonly hydrogen or an alkyl group, but which can be a more complicated group that varies from one type of linkage to another but is well known to the art skilled.

Representative United States Patents that teach the preparation of the above phosphorus atom containing linkages include, but are not limited to, U.S. Pat. Nos. 3,687,808; 4,469,863; 4,476,301; 5,023,243; 5,166,387; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,625,050; and 5,697,248, certain of which are commonly owned by the assignee of this application, and each of which is herein incorporated by reference.

Positional modifications, also known in the art, involve the linking of nucleosides in a non-naturally occurring motif. As used herein the term "positional modification" is meant to include without limitation 2',5'-internucleoside linkages. Combining modifications e.g. using modified chemistries and positional modifications of selected internucleoside linkages is also amenable to the present invention where for example a 2',5'-phosphoramidate internucleoside linkage is employed. The 2'–5'-linkage has been used at the termini of oligomeric compounds to enhance the nuclease resistance (as described in U.S. application Ser. No. 09/435, 806, filed Nov. 8, 1999).

A representative list of sugar substituent groups amenable to the present invention include $C_1$–$C_{20}$ alkyl, $C_2$–$C_{20}$ alkenyl, $C_2$–$C_{20}$ alkynyl, $C_5$–$C_{20}$ aryl, O-alkyl, O-alkenyl, O-alkynyl, O-alkylamino, (O-alkyl-N(H)alkyl), O-alkylaminodialkyl (O-alkyl-N-(alkyl)$_2$), O-alkylalkoxy (O-alkyl-O-alkyl), O-alkyl-(N-imidazole), S-alkenyl, S-alkynyl, NH-alkyl, NH-alkenyl, NH-alkynyl, N-dialkyl, O-aryl, S-aryl, NH-aryl, O-aralkyl, S-aralkyl, NH-aralkyl, N-phthalimido, halogen (particularly fluoro), keto, carboxyl, nitro, nitroso, nitrile, trifluoromethyl, trifluoromethoxy, imidazole, azido, hydrazino, hydroxylamino, isocyanato, sulfoxide, sulfone, sulfide, disulfide, silyl, heterocycle, carbocycle, polyamine, polyamide, polyalkylene glycol, and polyethers of the formula (O-alkyl)$_m$, where m is 1 to about 10. Preferred among these polyethers are linear and cyclic polyethylene glycols (PEGs), and (PEG)-containing groups, such as crown ethers and those which are disclosed by Ouchi et al. (*Drug Design and Discovery* 1992, 9, 93), Ravasio et al. (*J. Org. Chem.* 1991, 56, 4329) and Delgardo et. al. (*Critical Reviews in Therapeutic Drug Carrier Systems* 1992, 9, 249), each of which is herein incorporated by reference in its entirety. Further sugar modifications are disclosed in Cook, P. D., *Anti-Cancer Drug Design*, 1991, 6, 585–607. Fluoro, O-alkyl, O-alkylamino, O-alkyl imidazole, O-alkylaminoalkyl, and alkyl amino substitution is described in U.S. patent application Ser. No. 08/398,901, filed Mar. 6, 1995, entitled Oligomeric Compounds having Pyrimidine Nucleotide(s) with 2' and 5' Substitutions, hereby incorporated by reference in its entirety.

Additional sugar substituent groups amenable to the present invention include —SR and —NR$_2$ groups, wherein each R is, independently, hydrogen, a protecting group or substituted or unsubstituted alkyl, alkenyl, or alkynyl. 2'-SR nucleosides are disclosed in U.S. Pat. No. 5,670,633, issued Sep. 23, 1997, hereby incorporated by reference in its entirety. The incorporation of 2'-SR monomer synthons are disclosed by Hamm et al., *J. Org. Chem.*, 1997, 62, 3415–3420. 2'-NR$_2$ nucleosides are disclosed by Goettingen, M., *J. Org. Chem.*, 1996, 61, 6273–6281; and Polushin et al., *Tetrahedron Lett.*, 1996, 37, 3227–3230.

Further sugar substituent groups have one of formula I or II:

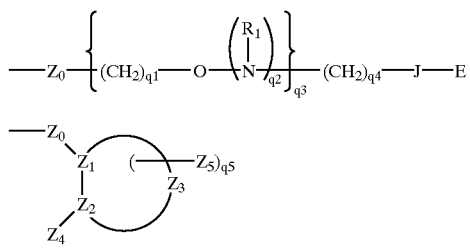

wherein:

$Z_0$ is O, S or NH;

J is a single bond, O or C(=O);

E is $C_1$–$C_{10}$ alkyl, N($R_1$) ($R_2$), N($R_1$) ($R_5$), N=C($R_1$) ($R_2$), N=C($R_1$) ($R_5$) or has one of formula III or IV;

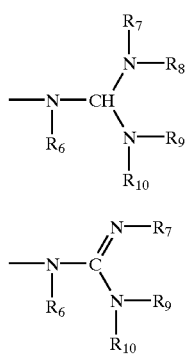

each $R_6$, $R_7$, $R_8$, $R_9$ and $R_{10}$ is, independently, hydrogen, C(O)$R_{11}$, substituted or unsubstituted $C_1$–$C_{10}$ alkyl, substituted or unsubstituted $C_2$–$C_{10}$ alkenyl, substituted or unsubstituted $C_2$–$C_{10}$ alkynyl, alkylsulfonyl, arylsulfonyl, a chemical functional group or a conjugate group, wherein the substituent groups are selected from hydroxyl, amino, alkoxy, carboxy, benzyl, phenyl, nitro, thiol, thioalkoxy, halogen, alkyl, aryl, alkenyl and alkynyl;

or optionally, $R_7$ and $R_8$, together form a phthalimido moiety with the nitrogen atom to which they are attached;

or optionally, $R_9$ and $R_{10}$, together form a phthalimido moiety with the nitrogen atom to which they are attached;

each $R_{11}$ is, independently, substituted or unsubstituted $C_1$–$C_{10}$ alkyl, trifluoromethyl, cyanoethyloxy, methoxy, ethoxy, t-butoxy, allyloxy, 9-fluorenylmethoxy, 2-(trimethylsilyl)-ethoxy, 2,2,2-trichloroethoxy, benzyloxy, butyryl, isobutyryl, phenyl or aryl;

$R_5$ is T-L,

T is a bond or a linking moiety;

L is a chemical functional group, a conjugate group or a solid support material;

each $R_1$ and $R_2$ is, independently, H, a nitrogen protecting group, substituted or unsubstituted $C_1$–$C_{10}$ alkyl, substituted or unsubstituted $C_2$–$C_{10}$ alkenyl, substituted or unsubstituted $C_2$–$C_{10}$ alkynyl, wherein the substitution is $OR_3$, $SR_3$, $NH_3^+$, N($R_3$) ($R_4$), guanidino or acyl where the acyl is an acid amide or an ester;

or $R_1$ and $R_2$, together, are a nitrogen protecting group or are joined in a ring structure that optionally includes an additional heteroatom selected from N and O;

or $R_1$, T and L, together, are a chemical functional group;

each $R_3$ and $R_4$ is, independently, H, $C_1$–$C_{10}$ alkyl, a nitrogen protecting group, or $R_3$ and $R_4$, together, are a nitrogen protecting group;

or $R_3$ and $R_4$ are joined in a ring structure that optionally includes an additional heteroatom selected from N and O;

$Z_4$ is OX, SX, or N(X)$_2$;

each X is, independently, H, $C_1$–$C_8$ alkyl, $C_1$–$C_8$ haloalkyl, C(=NH)N(H) Rs, C(=O)N(H) $R_5$ or OC(=O)N(H) $R_5$;

$R_5$ is H or $C_1$–$C_8$ alkyl;

$Z_1$, $Z_2$ and $Z_3$ comprise a ring system having from about 4 to about 7 carbon atoms or having from about 3 to about 6 carbon atoms and 1 or 2 hetero atoms wherein the hetero atoms are selected from oxygen, nitrogen and sulfur and wherein the ring system is aliphatic, unsaturated aliphatic, aromatic, or saturated or unsaturated heterocyclic;

$Z_5$ is alkyl or haloalkyl having 1 to about 10 carbon atoms, alkenyl having 2 to about 10 carbon atoms, alkynyl having 2 to about 10 carbon atoms, aryl having 6 to about 14 carbon atoms, N($R_1$) ($R_2$) $OR_1$, halo, $SR_1$ or CN;

each $q_1$ is, independently, an integer from 1 to 10;

each $q_2$ is, independently, 0 or 1;

q3 is 0 or an integer from 1 to 10;

$q_4$ is an integer from 1 to 10;

$q_5$ is from 0, 1 or 2; and provided that when $q_3$ is 0, $q_4$ is greater than 1.

Representative sugar substituent groups of Formula I are disclosed in U.S. patent application Ser. No. 09/130,973, filed Aug. 7, 1998, now U.S. Pat. No. 6,172,209, issued Jan. 9. 2001, entitled "Capped 2'-Oxyethoxy Oligonucleotides," hereby incorporated by reference in its entirety.

Representative cyclic sugar substituent groups of Formula II are disclosed in U.S. patent application Ser. No. 09/123,108, filed Jul. 27, 1998, now U.S. Pat. No. 6,271,358, issued Aug. 7, 2001, entitled "RNA Targeted 2'-Modified Oligonucleotides that are Conformationally Preorganized," hereby incorporated by reference in its entirety.

Particularly preferred sugar substituent groups include O[(CH$_2$)$_n$O]$_m$CH$_3$, O(CH$_2$)$_n$OCH$_3$, O(CH$_2$)$_n$NH$_2$, O(CH$_2$)$_n$CH$_3$, O(CH$_2$)$_n$ONH$_2$, O(CH$_2$)$_n$ON[(CH$_2$)$_n$CH$_3$)]$_2$ (where n and m are from 1 to about 10), $C_1$ to $C_{10}$ lower alkyl, substituted lower alkyl, alkaryl, aralkyl, O-alkaryl or O-aralkyl, SH, SCH$_3$, OCN, Cl, Br, GN, CF$_3$ OCF$_3$ SOCH$_3$ SO$_2$CH$_3$ONO$_2$ NO$_2$ N$_3$ NH$_2$ heterocycloalkyl, heterocycloalkaryl, aminoalkylamino, polyalkylamino and substituted silyl. Another particularly preferred modification includes 2'-methoxyethoxy (2'-O—CH$_2$CH$_2$OCH$_3$ or 2'-MOE, Martin et al., *Helv. Chim. Acta*, 1995, 78,486). A further preferred sugar substituent group is 2'-dimethylaminooxyethoxy, i.e., a O(CH$_2$)$_2$ON(CH$_3$)$_2$ group, also known as 2'-DMAOE. Representative aminooxy sugar substituent groups are described in co-owned U.S. patent application Ser. No. 09/344,260, filed Jun. 25, 1999, entitled "Aminooxy-Functionalized Oligomers", now U.S.

Pat. No. 6,576,752, issued June 10, 2003; and U.S. patent application Ser. No. 09/370,541, filed Aug. 9, 1999, also identified by, entitled Aminooxy-Functionalized Oligomers and Methods for Making Same now U.S. Pat. No. 6,639,062, issued Oct. 28, 2003; hereby incorporated by reference in their entirety.

Other preferred modifications useful as sugar substituent groups include 2'-methoxy (2'-O—CH$_3$),$_2$,-aminopropoxy (2'-OCH$_2$CH$_2$CH$_2$NH$_2$) and 2'-fluoro (2'-F). Similar modifications may also be made at other positions on nucleosides and oligomers, particularly the 3' position of the sugar on the 3' terminal nucleoside or at a 3'-position of a nucleoside that has a linkage from the 2'-position such as a 2'–5' linked oligomer and at the 5'-position at a 5'-terminus. Oligomers may also have sugar mimetics such as cyclobutyl moieties in place of the pentofuranosyl sugar. Representative United States patents that teach the preparation of such modified sugars structures include, but are not limited to, U.S. Pat. Nos. 4,981,957; 5,118,800; 5,319,080; 5,359,044; 5,393, 878; 5,446,137; 5,466,786; 5,514,785; 5,519,134; 5,567, 811; 5,576,427; 5,591,722; 5,597,909; 5,610,300; 5,627, 0531 5,639,873; 5,646,265; 5,658,873; 5,670,633; and 5,700,920, certain of which are commonly owned, and each of which is herein incorporated by reference, and commonly owned U.S. patent application Ser. No. 08/468,037, filed on Jun. 5, 1995, now U.S. Pat. No. 5,859,221, issued Jan. 12. 1999, also herein incorporated by reference.

Representative guanidino sugar substituent groups that are shown in formula III and IV are disclosed in co-owned U.S. patent application Ser. No. 09/349,040, entitled "Functionalized Oligomers", filed Jul. 7, 1999, now U.S. Pat. No. 6,593,466, issued July 15. 2003, hereby incorporated by reference in its entirety.

Representative acetamido sugar substituent groups are disclosed in U.S. patent application Ser. No. 09/378,568, entitled "2'-O-Acetamido Modified Monomers and Oligomers", filed Aug. 19, 1999, now U.S. Pat. No. 6,147, 200, issued Nov. 14, 2000, also identified by attorney docket number ISIS-407 1, hereby incorporated by reference in its entirety.

Representative dimethylaminoethyloxyethyl sugar substituent groups are disclosed in International Patent Application PCT/US99/17895, entitled "2'—O-Dimethylaminoethyloxyethyl-Modified Oligonucleotides", filed Aug. 6, 1999, also identified by attorney docket number ISIS-4045, hereby incorporated by reference in its entirety.

The use of mixed modifications in the terminal regions of an oligonucleotide to impart nuclease resistance is also within the scope of the present invention. For example an oligomeric compound of the invention can have enhanced nuclease resistance resulting from one or more modified internucleoside linkages at the 5' end and one or more sugar substituent groups at the 3' end. Another type of a mixed modification includes having a modified internucleoside linkage and a sugar substituent group at the same end of a selected oligomeric compound. Other examples include sugar substituent groups or modified linkages used in conjunction with a non-standard linkage such as a 2', 5'-internucleoside linkage.

Oligomeric compounds according to the present invention preferably comprise from about 5 to about 50 nucleosides. It is more preferred that such compounds comprise from about 8 to about 30 nucleosides, with 15 to 25 nucleosides being particularly preferred.

In general, the term "hetero" denotes an atom other than carbon, preferably but not exclusively N, O, or S. Accordingly, the term "heterocyclic ring" denotes an alkyl ring system having one or more heteroatoms (i.e., non-carbon atoms). Heterocyclic ring structures of the present invention can be fully saturated, partially saturated, unsaturated or with a polycyclic heterocyclic ring each of the rings may be in any of the available states of saturation. Heterocyclic ring structures of the present invention also include heteroaryl, which includes fused systems including systems where one or more of the fused rings contain no heteroatoms. Heterocycles, including nitrogen heterocycles, according to the present invention include, but are not limited to, imidazole, pyrrole, pyrazole, indole, 1H-indazole, α-carboline, carbazole, phenothiazine, phenoxazine, tetrazole, triazole, pyrrolidine, piperidine, piperazine and morpholine groups. A more preferred group of nitrogen heterocycles includes imidazole, pyrrole, indole, and carbazole groups.

A heterocyclic base moiety (often referred to in the art simply as a "base" or a "nucleobase") amenable to the present invention includes both naturally and non-naturally occurring nucleobases. The heterocyclic base moiety further may be protected wherein one or more functionalities of the base bears a protecting group. As used herein, "unmodified" or "natural" nucleobases include the purine bases adenine and guanine, and the pyrimidine bases thymine, cytosine and uracil. Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further nucleobases include those disclosed in U.S. Pat. No. 3,687,808, those disclosed in the *Concise Encyclopedia Of Polymer Science And Engineering*, pages 858–859, Kroschwitz, J. I., ed. John Wiley & Sons, 1990, those disclosed by Englisch et al., *Angewandte Chemie, International Edition*, 1991, 30, 613, and those disclosed by Sanghvi, Y. S., Chapter 15, *Antisense Research and Applications*, pages 289–302, Crooke, S. T. and Lebleu, B., ed., CRC Press, 1993.

Certain nucleobases are particularly useful for increasing the binding affinity of oligomeric compounds. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6–1.2° C. (Id., pages 276–278) and are presently preferred base substitutions, even more particularly when combined with 2'-methoxyethyl sugar modifications.

Representative United States patents that teach the preparation of modified nucleobases include, but are not limited to, U.S. Pat. Nos. 3,687,808; 4,845,205; 5,130,302; 5,134, 066; 5,175,273; 5,367,066; 5,432,272; 5,457,187; 5,459, 255; 5,484,908; 5,502,177; 5,525,711; 5,552,540; 5,587, 469; 5,594,121, 5,596,091; 5,614,617; and 5,681,941, certain of which are commonly owned, and each of which is herein incorporated by reference, and commonly owned U.S. patent application Ser. No. 08/762,588, filed on Dec. 10, 1996, now U.S. Pat. No. 5,750,692, issued May 12, 1998, also herein incorporated by reference.

The attachment of conjugate groups to oligomers is well documented in the prior art. The present methods include preparation of oligomeric compounds that include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugates groups include cholesterols, phospholipids, biotin, phenazine, phenanthridine, anthraquinone, acridine, fluoresceins, rhodamines, coumarins, and dyes. Groups that enhance the pharmacodynamic properties, in the context of this invention, include groups that improve oligomer uptake, enhance oligomer resistance to degradation, and/or strengthen sequence-specific hybridization with RNA. Groups that enhance the pharmacokinetic properties, in the context of this invention, include groups that improve oligomer uptake, distribution, metabolism or excretion. Representative conjugate groups are disclosed in International Patent Application PCT/US92/09196, filed Oct. 23, 1992, U.S. Pat. No. 5,578,718, issued Jul. 1, 1997, and U.S. Pat. No. 5,218,105. Each of the foregoing is commonly assigned with this application. The entire disclosure of each is incorporated herein by reference.

Preferred conjugate groups amenable to the present invention include lipid moieties such as a cholesterol moiety (Letsinger et al., *Proc. Natl. Acad. Sci. USA*, 1989, 86, 6553), cholic acid (Manoharan et al., *Bioorg. Med. Chem. Lett.*, 1994, 4, 1053), a thioether, e.g., hexyl-S-tritylthiol (Manoharan et al., *Ann. N.Y. Acad. Sci.*, 1992, 660, 306; Manoharan et al., *Bioorg. Med. Chem. Let.*, 1993, 3, 2765), a thiocholesterol (Oberhauser et al., *Nucl. Acids Res.*, 1992, 20, 533), an aliphatic chain, e.g., dodecandiol or undecyl residues (Saison-Behmoaras et al., *EMBO J.*, 1991, 10, 111; Kabanov et al., *FEBS Lett.*, 1990, 259, 327; Svinarchuk et al., *Biochimie*, 1993, 75, 49), a phospholipid, e.g., di-hexadecyl-rac-glycerol or triethylammonium-1,2-di-O-hexadecyl-rac-glycero-3-H-phosphonate (Manoharan et al., *Tetrahedron Lett.*, 1995, 36, 3651; Shea et al., *Nucl. Acids Res.*, 1990, 18, 3777), a polyamine or a polyethylene glycol chain (Manoharan et al., *Nucleosides & Nucleotides*, 1995, 14, 969), adamantane acetic acid (Manoharan et al., *Tetrahedron Lett.*, 1995, 36, 3651), a palmityl moiety (Mishra et al., *Biochim. Biophys. Acta*, 1995, 1264, 229), or an octadecylamine or hexylamino-carbonyl-oxycholesterol moiety (Crooke et al., *J. Pharmacol. Exp. Ther.*, 1996, 277, 923).

Other groups that can be attached to oligomeric compounds to modify antisense properties include RNA cleaving complexes, pyrenes, metal chelators, porphyrins, alkylators, hybrid intercalator/ligands and photo-cross-linking agents. RNA cleavers include o-phenanthroline/Cu complexes and Ru(bipyridine)$_3^{2+}$ complexes. The Ru(bpy)$_3^{2+}$ complexes are believed to interact with nucleic acids and cleave nucleic acids photochemically. Metal chelators include EDTA, DTPA, and o-phenanthroline. Alkylators include compounds such as iodoacetamide. Porphyrins include porphine, its substituted forms, and metal complexes. Pyrenes include pyrene and other pyrene-based carboxylic acids that could be conjugated using the similar protocols.

As used herein, "polyamine" refers to a moiety containing a plurality of amine or substituted amine functionalities. Polyamines according to the present invention have at least two amine functionalities. "Polypeptide" refers to a polymer comprising a plurality of amino acids linked by peptide linkages, and includes dipeptides and tripeptides. The amino acids may be naturally-occurring or non-naturally-occurring amino acids. Polypeptides according to the present invention comprise at least two amino acids.

The methods of the present invention illustrate the use of activated phosphorus compositions (e.g. compounds having activated phosphorus-containing substituent groups) in coupling reactions. As used herein, the term activated phosphorus composition includes monomers and oligomers that have an activated phosphorus-containing substituent group that is reactive with a hydroxyl group of another monomeric or oligomeric compound to form a phosphorus-containing internucleotide linkage. Such activated phosphorus groups contain activated phosphorus atoms in $p^{III}$ valence state. Such activated phosphorus atoms are known in the art and include, but are not limited to, phosphoramidite, H-phosphonate, phosphate triesters and chiral auxiliaries. A preferred synthetic solid phase synthesis utilizes phosphoramidites as activated phosphates. The phosphoramidites utilize $P^{III}$ chemistry. The intermediate phosphite compounds are subsequently oxidized to the pv state using known methods to yield, in a preferred embodiment, phosphodiester or phosphorothioate internucleotide linkages. Additional activated phosphates and phosphites are disclosed in Tetrahedron Report Number 309 (Beaucage and Iyer, *Tetrahedron*, 1992, 48, 2223–2311).

A representative list of activated phosphorus containing monomers or oligomers include those having the formula:

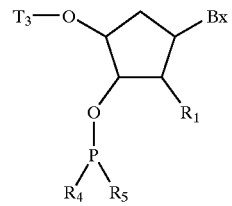

wherein
each Bx is, independently, a heterocyclic base moiety or a blocked heterocyclic base moiety; and
each $R_1$ is, independently, H, a blocked hydroxyl group, a sugar substituent group, or a blocked substituent group;
$T_3$ is an hydroxyl protecting group, a nucleoside, a nucleotide, an oligonucleoside or an oligonucleotide;
$R_4$ is $N(L_1)L_2$;
each $L_1$ and $L_2$ is, independently, $C_{1-6}$ alkyl;
or $L_1$ and $L_2$ are joined together to form a 4- to 7-membered heterocyclic ring system including the nitrogen atom to which $L_1$ and $L_2$ are attached, wherein the ring system optionally includes at least one additional heteroatom selected from O, N and S; and
$R_5$ is $X_1$;
$X_1$ is Pg-O—, Pg-S—, $C_1$–$C_{10}$ straight or branched chain alkyl, $CH_3(CH_2)_{nn}$—O— or $R_2R_3N$—;
nn is from 0 to 10;
Pg is a blocking group;
each $R_2$ and $R_3$ is, independently, hydrogen, $C_1$–$C_{10}$ alkyl, cycloalkyl or aryl;
or optionally, $R_2$ and $R_3$, together with the nitrogen atom to which they are attached form a cyclic moiety that may include an additional heteroatom selected from O, S and N; or
$R_4$ and $R_5$together with the phosphorus atom to which $R_4$ and $R_5$ are attached form a chiral auxiliary.

Groups that are attached to the phosphorus atom of internucleotide linkages before and after oxidation ($R_4$ and $R_5$) can include nitrogen containing cyclic moieties such as morpholine. Such oxidized internucleoside linkages include a phosphoromorpholidothioate linkage (Wilk et al., *Nucleosides and nucleotides,* 1991, 10, 319–322). Further cyclic moieties amenable to the present invention include mono-, bi- or tricyclic ring moieties which may be substituted with groups such as oxo, acyl, alkoxy, alkoxycarbonyl, alkyl, alkenyl, alkynyl, amino, amido, azido, aryl, heteroaryl, carboxylic acid, cyano, guanidino, halo, haloalkyl, haloalkoxy, hydrazino, ODMT, alkylsulfonyl, nitro, sulfide, sulfone, sulfonamide, thiol and thioalkoxy. A preferred bicyclic ring structure that includes nitrogen is phthalimido.

Some representative examples of $R_4$ and $R_5$ groups which are known to the art skilled and are amenable to the present invention are shown below:

further examples include:

-continued

| $R_4$ | $R_5$ | $R_4$ | $R_5$ |
|---|---|---|---|
| —N(morpholino, O) | —O—CH₂CH₂—C₆H₄—NO₂ | —N(thiomorpholino, S) | —O—CH₃ |
| —N(morpholino, O) | —O—CH₂CH₂—S(=O)₂—CH₃ | —N(azepane) | —O—CH₃ |
| —N(azepane) | —O—CH₂CH₂—C₆H₄—NO₂ | —N(azocane) | —O—CH₃ |

A number of chemical functional groups can be introduced into compounds of the invention in a blocked form and subsequently deblocked to form a final, desired compound. Such as groups directly or indirectly attached at the heterocyclic bases, the internucleoside linkages and the sugar substituent groups at the 2', 3' and 5'-positions. Protecting groups can be selected to block functional groups located in a growing oligomeric compound during iterative oligonucleotide synthesis while other positions can be selectively deblocked as needed. In general, a blocking group renders a chemical functionality of a larger molecule inert to specific reaction conditions and can later be removed from such functionality without substantially damaging the remainder of the molecule (Greene and Wuts, *Protective Groups in Organic Synthesis,* 3rd ed, John Wiley & Sons, New York, 1999). For example, the nitrogen atom of amino groups can be blocked as phthalimido groups, as 9-fluorenylmethoxycarbonyl (FMOC) groups, and with triphenylmethylsulfenyl, t-BOC or benzyl groups. Carboxyl groups can be blocked as acetyl groups. Representative hydroxyl protecting groups are described by Beaucage et al., *Tetrahedron* 1992, 48, 2223. Preferred hydroxyl protecting groups are acid-labile, such as the trityl, monomethoxytrityl, dimethoxytrityl, trimethoxytrityl, 9-phenylxanthine-9-yl (Pixyl) and 9-(p-methoxyphenyl)xanthine-9-yl (MOX).

Chemical functional groups can also be "blocked" by including them in a precursor form. Thus, an azido group can be used considered as a "blocked" form of an amine since the azido group is easily converted to the amine. Further representative protecting groups utilized in oligonucleotide synthesis are discussed in Agrawal, et al., Protocols for Oligonucleotide Conjugates, Eds, Humana Press; New Jersey, 1994; Vol. 26 pp. 1–72.

Examples of hydroxyl protecting groups include, but are not limited to, t-butyl, t-butoxymethyl, methoxymethyl, tetrahydropyranyl, 1-ethoxyethyl, 1-(2-chloroethoxy)ethyl, 2-trimethylsilylethyl, p-chlorophenyl, 2,4-dinitrophenyl, benzyl, 2,6-dichlorobenzyl, diphenylmethyl, p,p'-dinitrobenzhydryl, p-nitrobenzyl, triphenylmethyl, trimethylsilyl, triethylsilyl, t-butyldimethylsilyl, t-butyldiphenylsilyl, triphenylsilyl, benzoylformate, acetate, chloroacetate, trichloroacetate, trifluoroacetate, pivaloate, benzoate, p-phenylbenzoate, 9-fluorenylmethyl carbonate, mesylate and tosylate.

Amino-protecting groups stable to acid treatment are selectively removed with base treatment, and are used to make reactive amino groups selectively available for substitution. Examples of such groups are the Fmoc (E. Atherton and R. C. Sheppard in *The Peptides,* S. Udenfriend, J. Meienhofer, Eds., Academic Press, Orlando, 1987, volume 9, p.1), and various substituted sulfonylethyl carbamates exemplified by the Nsc group (Samukov et al., *Tetrahedron Lett,* 1994, 35:7821; Verhart and Tesser, *Rec. Trav. Chim. Pays-Bas,* 1987, 107:621).

Additional amino-protecting groups include but are not limited to, carbamate-protecting groups, such as 2-trimethylsilylethoxycarbonyl (Teoc), 1-methyl-1-(4-biphenylyl)ethoxycarbonyl (Bpoc), t-butoxycarbonyl (BOC), allyloxycarbonyl (Alloc), 9-fluorenylmethyloxycarbonyl (Fmoc), and benzyloxycarbonyl (Cbz); amide-protecting groups, such as formyl, acetyl, trihaloacetyl, benzoyl, and nitrophenylacetyl; sulfonamide-protecting groups, such as 2-nitrobenzenesulfonyl; and imine- and cyclic imide-protecting groups, such as phthalimido and dithiasuccinoyl. Equivalents of these amino-protecting groups are also encompassed by the compounds and methods of the present invention.

In some especially preferred embodiments, the nucleoside components of the oligomeric compounds are connected to each other by optionally protected phosphorothioate internucleoside linkages. Representative protecting groups for phosphorus containing internucleoside linkages such as phosphite, phosphodiester and phosphorothioate linages include β-cyanoethyl, diphenylsilylethyl, 5-cyanobutenyl, cyano p-xylyl (CPX), N-methyl-N-trifluoroacetyl ethyl (META), acetoxy phenoxy ethyl (APE) and butene-4-yl groups. See for example U.S. Pat. Nos. 4,725,677 and Re. 34,069 (β-cyanoethyl); Beaucage, S. L. and Iyer, R. P., *Tetrahedron,* 49 No. 10, pp. 1925–1963 (1993); Beaucage, S. L. and Iyer, R. P., *Tetrahedron,* 49 No. 46, pp. 10441–10488 (1993); Beaucage, S. L. and Iyer, R. P., *Tetrahedron,* 48 No. 12, pp. 2223–2311 (1992).

Standard oligonucleotide synthesis using phosphite ($P^{III}$) chemistry involves treatment of the growing oligomer with a deprotecting reagent to create a free hydroxyl position that is available for a further coupling reaction. Hydroxyl protecting groups are preferably removed using a weak acid. Dependant on the choice of protecting group the deprotecting reagent can be acidic, basic, neutral or fluoride mediated. A representative list of deprotecting reagents amenable to the present methods includes without limitation protic acids used for removing acid labile protecting groups such as dichloro- and trichloroacetic acids, Lewis acids such as BF$_3$-etherate, zinc bromide, AlCl$_3$, TiCl$_4$, (Et)AlCl, (I-Bu)$_2$AlCl and other reagents such as ceric ammonium nitrate, 1,1,1,3,3,3-hexafluoro-2-propanol, and diethyloxomalonate. A preferred deprotecting reagent that is used routinely for example for the removal of various trityl protecting groups is 2–5% dichloroacetic acid in either dichloromethane or dichloroethane.

After synthesis the resulting oligomeric compound generally is cleaved from the solid support to obtain the free oligomer. The step of deprotecting the blocked 5'-O-hydroxyl is usually performed separately as this is generally accomplished using an acidic deblocking reagent. This step is routinely performed after deprotection, cleavage and purification has been performed to enhance the purification process by keeping the terminal hydroxyl blocked. The deprotection and cleavage steps can be separated into separate steps or combined into a single step depending on the particular protecting groups, solid support linking groups and the choice of reagent or reagents used. In a preferred embodiment the simultaneous deprotection and cleavage of the final oligomeric compound following synthesis is accomplished in one step using a solution of ammonium hydroxide (NH$_4$OH (30%) for 15 hours at 60° C., filtered, rinsed with ethanol/water (1/1, v/v), the combined solutions are evaporated to dryness under vacuum).

The purification of oligomeric compounds is generally by reversed phase high performance liquid chromatography (RP-HPLC) performed on a Waters Nova-Pak C18 column (3.9×300 mm) using a Waters HPLC system (600E System Controller, 996Photodiode Array Detector, 717 Autosampler). For analysis an acetonitrile (A)/0.1 M triethylammonium acetate gradient is used: 5% to 35% A from 0 to 10 min, then 35% to 40% A from 10 to 20 min, then 40% to 95% A from 20 to 25 min, flow rate=10 mL/min/50% A from 8 to 9 min, 9 to 26 min at 50%, flow rate=1.0 mL/min, tR(DMT-off) 10–11 min, tR(DMT-on) 14–16 min. The DMT-on fractions are collected and are evaporated in vacuum, redissolved in water and the DMT group removed as described below.

Removal of the final hydroxyl protecting group from the 5'-hydroxyl group is generally performed by treatment with an acidic solution such as acetic acid. The oligomeric compound is treated with the acidic solution for about 30 minutes at room temperature. The mixture is further treated with sodium acetate and cold ethanol followed by vortexing and cooling with dry ice. The precipitate is centrifuged, separated, washed and dried to give the final deprotected product.

The term "nucleoside" as used in connection with this invention refers to a monomeric unit made up of a heterocyclic base moiety joined to a sugar moiety or sugar mimetic through a glycosyl linkage. The term "nucleotide" refers to a nucleoside having a phosphate group on its 3' or 5' sugar hydroxyl group.

In the context of this invention, the terms "oligomer" and "oligomeric compound" refer to a plurality of naturally-occurring or non-naturally-occurring nucleosides joined together in a specific sequence. The terms "oligomer" and "oligomeric compound" include oligonucleotides, oligonucleotide analogs, oligonucleosides and chimeric oligomeric compounds where there are more than one type of internucleoside linkages dividing the oligomeric compound into regions. Whereas the term "oligonucleotide" has a well defined meaning in the art, the term "oligomeric compound" or "oligomer" is intended to be broader, inclusive of oligomers having all manner of modifications known in the art. Gapped or chimeric compounds are disclosed in for example, U.S. Pat. No. 5,623,065, issued Apr. 22, 1997, the contents of which are incorporated herein by reference.

As used herein, the term "oligonucleoside" includes oligomers or polymers containing two or more nucleoside subunits having a non-phosphodiester linking moiety. Oligonucleosides according to the invention have a ribofuranose moiety attached to a nucleobase through a glycosyl bond.

Gapmer technology has been developed to incorporate modifications at the ends ("wings") of oligomeric compounds, leaving a phosphorothioate gap in the middle for RNase H activation (Cook, P. D., Anti-Cancer Drug Des., 1991, 6, 585–607; Monia et al., J. Biol. Chem., 1993, 268, 14514–14522). In a recent report, the activities of a series of uniformly 2'-O modified 20 mer RNase H-independent oligonucleotides that were antisense to the 5'-cap region of human ICAM-1 transcript in HUVEC cells, were compared to the parent 2'-deoxy phosphorothioate oligonucleotide (Baker et al., J. Bio. Chem., 1997, 272, 11994–12000). The 2'-MOE/P=O oligomer demonstrated the greatest activity with an IC$_{50}$ of 2.1 nM (T$_m$=87.1° C.), while the parent P=S oligonucleotide analog had an IC$_{50}$ of 6.5 nM (T$_m$=79.2° C.). Correlation of activity with binding affinity is not always observed as the 2'-F/P=S (T$_m$=87.9° C.) was less active than the 2'-MOE/P=S (T$_m$=79.2° C.) by four fold. The RNase H competent 2'-deoxy P=S parent oligonucleotide exhibited an IC$_{50}$=41 nM.

As used herein the term "chiral auxiliary" is meant to include groups that function to provide chirality to internucleoside phosphorus linkages during synthesis. Chiral auxiliaries amenable to the present invention include those that form a P$^{III}$ intermediate capable of being oxidized. Chiral auxiliaries will give either Sp or Rp chirality for the respective internucleoside linkage in the final oligomeric compound. Accordingly, chiral auxiliaries are allowed to remain on the growing chain, and are removed at the end of the iterative synthetic regime. Removal of chiral auxiliaries can be conveniently accomplished in a single treatment after the completion of the iterative synthesis. Chiral auxiliaries and methods of their incorporation using standard protocols are disclosed in commonly owned U.S. patent application Ser. No. 09/438,989, filed on Nov. 12, 1999, incorporated herein by reference. Further chiral auxiliaries have been previously reported for use in the preparation of oligomeric phosphorothioates (see Iyer et al., Tetrahedron letters, 1998, 39, 2491–2494 and Wilk et al., J. Am. Chem. Soc., 2000, 122, 2149–2156). Representative chiral auxiliaries include, without limitation those having the following formulas:

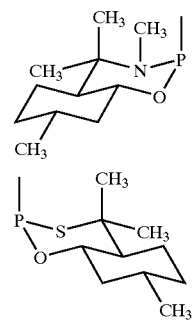

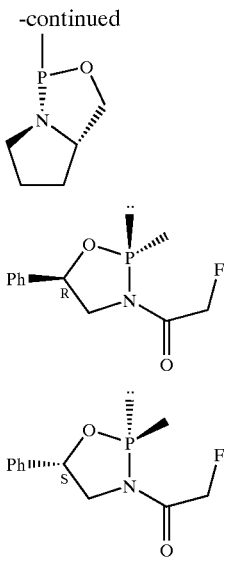

As used herein, the term "alkyl" includes, but is not limited to, straight chain, branched chain and alicyclic hydrocarbon groups. Alkyl groups of the present invention may be substituted. Representative alkyl substituents are disclosed in U.S. Pat. No. 5,212,295, at column 12, lines 41–50, hereby incorporated by reference in its entirety. Substituent groups include, but are not limited to, alkyl, alkenyl, alkynyl, aryl, hydroxyl, alkoxy, alcohol, benzyl, phenyl, nitro, thiol, thioalkoxy, thioalkyl, trifluoromethyl, halo, nitrile, trifluoromethoxy and azido. As used herein, the term "lower alkyl" is intended to mean an alkyl group having 10 or fewer carbons.

Alkenyl groups according to the invention are to straight chain, branch chain, and cyclic hydrocarbon groups containing at least one carbon—carbon double bond, and alkynyl groups are to straight chain, branch chain, and cyclic hydrocarbon groups containing at least one carbon—carbon triply bond. Alkenyl and alkynyl groups of the present invention can be substituted.

Aryl groups are substituted and unsubstituted aromatic cyclic moieties including but not limited to phenyl, naphthyl, anthracyl, phenanthryl, pyrenyl, and xylyl groups. Alkaryl groups are those in which an aryl moiety links an alkyl moiety to a core structure, and aralkyl groups are those in which an alkyl moiety links an aryl moiety to a core structure.

As used herein, the term "aralkyl" denotes alkyl groups which bear aryl groups, for example, benzyl groups. The term "alkaryl" denotes aryl groups which bear alkyl groups, for example, methylphenyl groups. As used herein, the term "aryl" denotes aromatic cyclic groups including, but not limited to, phenyl, naphthyl, anthracyl, phenanthryl and pyrenyl. Preferred aryl and aralkyl groups include, but are not limited to, phenyl, benzyl, xylyl, naphthyl, toluyl, pyrenyl, anthracyl, azulyl, phenethyl, cinnamyl, benzhydryl, and mesityl. Typical substituents for substitution include, but are not limited to, hydroxyl, alkoxy, alcohol, benzyl, phenyl, nitro, thiol, thioalkoxy, halogen, or alkyl, aryl, alkenyl, or alkynyl groups.

As used herein, the term "alkanoyl" has its accustomed meaning as a group of formula —C(=O)-alkyl. A preferred alkanoyl group is the acetyl group.

As used herein, the term "sulfurizing reagent" includes without limitation, dimethylthiuram disulfide (Cummings et al., *Ind. Eng. Chem.*, 1928, 20, 1173); 1,2,4-dithiazolidine-3,5-dione (DTSNH, see Xu et al., *Nucleic Acids Research*, 1996, 24, 1602–1607); 3-methyl-1,2,4-dithiazolin-5-one (MEDITH, see Zang et al., *Tetrahedron Lett.*, 1999, 40, 2095–20980); phenylacetyl disulfide (PADS, see Kamer et al., *Tetrahedron Lett.*, 1989, 30, 6757–6760; Cheruvallath et al., *Organic Process Research & Development*, 2000, 4, 199–204); tetraethylthiuram disulfide (TETD, see Vu et al., *Tetrahedron Lett.*, 1991, 32, 3005–3008); 3H-1,2-benzodithiol-3-one-1,1-dioxide (Beaucage reagent, see e.g. Iyer, R. P., et. al., *J. Chem. Soc.*, 1990, 112, 1253–1254, and Iyer, R. P., et. al., *J. Org. Chem.*, 1990, 55, 4693–4699); tetraethylthiuram disulfide (see e.g., Vu, H., Hirschbein, B. L., *Tetrahedron Lett.*, 1991, 32, 3005–3008); dibenzoyl tetrasulfide (see e.g., Rao, M. V., et.al., *Tetrahedron Lett.*, 1992, 33, 4839–4842); benzyltriethylammonium tetrathiomolybdate (BTTM, see e.g., Rao, M. V., et.al., *Tetrahedron Lett.*, 1994, 35, 6741–6744); di(phenylacetyl)-disulfide (see e.g., Kamer, P. C. J., *Tetrahedron Lett.*, 1989, 30, 6757–6760); Bis(O,O-diisopropoxy phosphinothioyl) disulfides (see Stec et al., *Tetrahedron Lett.*, 1993, 34, 5317–5320); 3-ethoxy-1,2,4-dithiazoline-5-one (EDITH, see Xu et al., *Nucleic Acids Research*, 1996 24, 1602–1607, and *Nucleic Acids Research*, 1996 24, 3643–3644); Bis(p-chlorobenzenesulfonyl)disulfide (see *Nucleic Acids Research*, 1995 23, 4029–4033); bis(ethoxythiocarbonyl) tetrasulfide (see Zang et ai., *Tetrahedron Lett.*, 1998, 39, 2467–2470); bis(p-toluenesulfonyl)disulfide (Efimov et al., *Nucleic Acids Res.*, 1995, 23, 4029–4033); 3-amino-1,2,4-dithiazole-5-thione (see *Org. Process Res. Dev.*, 2000, 4, 194–198); ethylthiuram disulfide CAS # 3082-38-0; 5,6-dihydro-3H-imidazo[2,1-C]-1,2,4-dithiazole-3-thione CAS # 33813-20-6; 4-methyl-5-(methylimino)-1,2,4-dithiazolidine-3-thione CAS #20042-85-7; sulfur, sulfur in combination with ligands like triaryl, trialkyl, triaralkyl, or trialkaryl phosphines. The foregoing references are hereby incorporated by reference in their entirety.

A preferred list of sulfurizing reagents includes: 3-amino-1,2,4-dithiazole-5-thione; 3-ethoxy-1,2,4-dithiazoline-5-one; 1,2,4-dithiazolidine-3,5-dione; 3-methyl-1,2,4-dithiazolin-5-one; and dimethylthiuram disulfide.

A representative list of capping reagents useful in the methods of the present invention include without limitation, acetic anhydride, t-butylphenoxyacetic anhydride, phosphite monoesters, and selected acid chlorides preferably delivered concurrently with a nucleophilic catalyst (e.g. a strong base) such as for example N-methylimidazole or triethylamine. Generally capping reagents comprise a mixture of Cap A and Cap B. Representative mixtures include without limitation:

Cap A: acetic anhydride in acetonitrile or tetrahydrofuran;
chloroacetic anhydride in acetonitrile or tetrahydrofuran;
Cap B: N-methylimidazole and pyridine in acetonitrile or tetrahydrofuran;
4-dimethylaminopyridine (DMAP) and pyridine in acetonitrile or tetrahydrofuran;
2,6-lutidine and N-methylimidazole in acetonitrile or tetrahydrofuran.

A more detailed description capping reagents is discussed in U.S. Pat. No. 4,816,571, issued Mar. 28, 1989 which is incorporated herein by reference. A preferred capping reagent is acetic anhydride routinely used as a mixture of cap A and cap B.

During the coupling step one compound having an active phosphate is coupled to a second compound having a free hydroxyl group. An activating agent is not believed to be essential for this step but one is generally used to increase the reaction efficiency. A list of activators and references for each can be found in Eleueri et al., *Organic Process*

*Research & Development*, 2000, 4, 182–189. Preferred activators include without limitation: 1H-tetrazole, 5-(2-nitrophenyl)-1H-tetrazole, 5-(p-nitrophenyl)-1H-tetrazole, 5-trifluoromethyl-1H-tetrazole, 5-ethylthio-1H-tetrazole, 5-benzyltio-1H-tetrazole, 2,4,5-tribromoimidazole, 2-nitroimidazole, 4,5-dichloroimidazole, 2-bromo-4,5-dicyanoimidazole, 4,5-dicyanoimidazole, N-methylimidazole hydrochloride, 1-hydroxybenzotriazole, 5-chlorobenzotriazole, chlorotrimethylsilane, benzimidazolium triflate, imidazolium triflate, pyridinium hydrochloride/-imidazole, pyridinium tetrafluoroborate, pyridinium chloride, pyridinium bromide, pyridinium 4-methylbenzene-sulfonate, N-methylimidazolium trifluroborate, N-methyl-anilinium trichloroacetate, N-methylanilinium trifluoro-acetate, 1H-tetrazole/DMAP, 1H-tetrazole/N-methylimidazole, and N-methylimidazolium trifluoromethanesulfonate (see review article Beaucage et al., *Current Protocols in Nucleic Acid Chemistry*, 2000, 3.3.1-3.3.20).

The current method of choice for the preparation of oligomeric compounds uses support methodologies using a selected support media. A support media can be purchased from a commercial source with a linking moiety for attaching the first nucleoside or alternatively a support media can be modified with a desired linker. A preferred linking moiety is bifunctional and upon cleavage remains attached to the oligomeric compound such as for example 3'-thiol-modifier C3 S—S CPG. The linking moiety reversibly attaches the first added nucleoside or larger nucleosidic synthon to the support media which is then iteratively elongated to give a final oligomeric compound. Support media can be selected to be insoluble or have variable solubility in different solvents to allow the growing oligomer to be kept out of or in solution as desired. Traditional solid supports are insoluble and are routinely placed in a reaction vessel while reagents and solvents react and or wash the growing chain until cleavage frees the final oligomer. More recent approaches have introduced soluble supports including soluble polymer supports to allow precipitating and dissolving the bound oligomer at desired points in the synthesis (Gravert et al., *Chem. Rev.*, 1997, 97, 489–510). Representative support media that are amenable to the methods of the present invention include without limitation: controlled pore glass (CPG); oxalyl-controlled pore glass (see, e.g., Alul, et al., *Nucleic Acids Research* 1991, 19, 1527); TENTAGEL Support, (see, e.g., Wright, et al., *Tetrahedron Letters* 1993, 34, 3373); or POROS, a copolymer of polystyrene/divinylbenzene available from Perceptive Biosystems. The use of a soluble support media, poly(ethylene glycol), with molecular weights between 5 and 20 kDa, for large-scale synthesis of phosphorothioate oligonucleotides is described in, Bonora et al., *Organic Process Research & Development*, 2000, 4, 225–231.

It was previously reported (Cummings A. D. et al. Ind. Eng. Chem., 1928, 20, 1173) that dimethylthiuram disulfide was not a stable compound and decomposes slowly on standing. The dimethylthiuram disulfide, after standing for 1 month, failed to show a melting point of 102° C. The decomposition products were identified as hydrogen sulfide, elemental sulfur and methyl isothiocyanate. The lack of long shelf life for dimethylthiuram disulfide has been attributed to the dithiocarbamate derivative of methylamine, which is a primary amine. The present invention provides a new and improved procedure for the synthesis of dimethylthiuram disulfide (see Example 7) which utilizes an acid wash at the end of the synthesis. The primary amine is protonated which stabilizes the dithiocarbamate structure from degradation. A further improvement was realized by oxidizing the intermediate with hydrogen peroxide as opposed to iodine. This led to the preparation of white crystalline product instead of the yellow unstable product previously reported. Dimethylthiuram disulfide made by this protocol is very stable even after six months of storage at room temperature.

Oligomeric compounds prepared by the methods of the present invention can be used in diagnostics, therapeutics and as research reagents and kits. They can also be used in pharmaceutical compositions by including a suitable pharmaceutically acceptable diluent or carrier. They can further be used for treating organisms having a disease characterized by the undesired production of a protein. For this purpose, the organism is contacted with an oligomer having a sequence that is capable of specifically hybridizing with a strand of nucleic acid encoding the undesirable protein. Treatments of this type can be practiced on a variety of organisms ranging from unicellular prokaryotic and eukaryotic organisms to multicellular eukaryotic organisms. Any organism that utilizes DNA-RNA transcription or RNA-protein translation as a fundamental part of its hereditary, metabolic or cellular control is susceptible to therapeutic and/or prophylactic treatment in accordance with the invention. Seemingly diverse organisms such as bacteria, yeast, protozoa, algae, all plants and all higher animal forms, including warm-blooded animals, can be treated. Further, each cell of multicellular eukaryotes can be treated, as they include both DNA-RNA transcription and RNA-protein translation as integral parts of their cellular activity. Furthermore, many of the organelles (e.g., mitochondria and chloroplasts) of eukaryotic cells also include transcription and translation mechanisms. Thus, single cells, cellular populations or organelles can also be included within the definition of organisms that can be treated with therapeutic or diagnostic oligomeric compounds of the invention.

Those skilled in the art will appreciate that numerous changes and modifications may be made to the preferred embodiments of the invention and that such changes and modifications may be made without departing from the spirit of the invention. It is, therefore, intended that the appended claims cover all such equivalent variations as fall within the true spirit and scope of the invention.

EXAMPLES

General

Dithiothreitol (DTT), 2,2'-dithiodipyridine (aldrithiol-2) and 1-hexanethiol were purchased from Aldrich. Peptides were synthesized by Commonwealth Biotechnologies, Inc., Richmond, Va. Antennapedia peptide: C(N-Ac)-GABA-GGRQIKIWFQNRLRMKWKK-amide (GABA=γ-aminobutyric acid (SEQ ID NO: 7). Bicyclic RGD peptide: 3-mercaptopropionyl-GABA-GGACDCRGDCFCG-amide (SEQ ID NO: 16).

Example 1
Oligonucleotide Synthesis

The 20-mer oligonucleotide phosphorothioate 2'-methoxyethoxy (MOE, 2'-O—$CH_2CH_2$—O—$CH_3$) gapmers were synthesized on ABI 380B DNA synthesizer on a 25 mmol scale. The use of 3'-thiol-modifier C3 S—S CPG (Glen Research) gives a 3'-O—P(=S) (—O)—$(CH_2)_3$—S—S—$(CH_2)_3$—OH group at the 3'-terminus of selected oligonucleotides upon cleavage from the solid support.

Example 2
A General Procedure for Activation of 3'-Disulfide Modified Oligonucleotides to give 3'-O—P (=S) (—O)—$(CH_2)_3$—S—S— (2-pyridine)

HPLC purified, 3'-disulfide modified oligonucleotide (1000 OD) was treated with DTT (5 mL, 0.25M in 0.1M NaHCO$_3$/Na$_2$CO$_3$ buffer, pH 9.0) for 2 hours at ambient temperature. The reaction mixture was directly loaded onto an HPLC column (Delta-Pak C18, 25×100=m, 300 Å, 15 µ). The column was eluted using 0.1M NH$_4$OAc as buffer A, 80% aqueous MeCN as buffer B, and linear gradient from 0 to 45% of B in 60 minutes at a flow rate 15 mL/min. The fractions containing 3'-O—P(=S) (—O)—(CH$_2$)$_3$—SH modified oligonucleotide were collected directly to a solution of 2,2'-dithiodipyridine (20 mg) in MeCN (2 mL). The reaction mixture was kept for 2 hours and concentrated in vacuum. The excess 2,2'-dithiodipyridine was extracted with ethyl acetate (2×10 mL). The activated oligonucleotide having a 3'-O—P(=S) (—O)—(CH$_2$)$_3$—S—S—(2-pyridine) was purified by HPLC using the conditions specified above. Activated oligonucleotides were stored for short periods of time in a refrigerator.

Example 3
General Procedure for Conjugation of Activated/Functionalized Oligonucleotide with Antennapedia Peptide A solution of an activated oligonucleotide (8 OD/mL in 20–30% aqueous MeCN, 0.1M KCl, 1M urea, 0.1M NH$_4$OAc, and 1 mM diisopropylethylamine) was degassed, and the flask was filled with argon. Antennapedia peptide (1 equivalent, 3 nmol/mL in freshly boiled and cooled water) was added slowly in 2 portions under gentle mixing. When a local precipitation was observed, the addition was stopped, and the mixture was stirred until the precipitate was dissolved. The reaction mixture was kept for 1–2 hours at ambient temperature. As judged by ion-exchange HPLC, addition of peptide (1 equivalent) results in 70–80% conversion of the starting oligonucleotide. After evaporation of MeCN, a peptide-oligonucleotide conjugate was purified by RP-HPLC on Delta Pak C4 column (19×300 mm, 300 Å, 15 µ) using 0.1M NH$_4$OAc as buffer A, 80% aqueous MeCN as buffer B, and a linear gradient from 0 to 60% of in 40 minutes at a flow rate of 10 mL/min. When an additional 0.2 equivalent of peptide were added, the conversion of the starting oligonucleotide was more than 90%. In this case, purification was better using ion-exchange HPLC. Desalting of the oligonucleotide-peptide conjugate was performed by RP-HPLC on Zorbax C3 column to furnish the product as either NH$_4^+$ or Na$^+$ salt.

Example 4
Synthesis of SEQ ID No. 1 3'-Antp on 420 OD Scale

Activated SEQ ID No. 1 (13920-3'-S—SPy) oligonucleotide (420 OD, 2.32 mmol) in HPLC buffer (25 mL) was diluted with 1M KCl (10 mL), 2M urea and 0.1M NH$_4$OAc in 30% aqueous MeCN (50 mL), diisopropylethylamine (125 mL), and MeCN (20 mL). The resulting solution was degassed, and the flask was filled with argon. Aqueous Antp-SH peptide (10 mg/mL, 0.5 equivalent, 1.26 mmol, 385 mL) was added slowly with stirring.

The reaction mixture was analyzed by ion exchange HPLC on a Poros DNA Q column (4.6×50 mm) using: 0.1M NH$_4$OAc and 2M urea in 30% aqueous MeCN as buffer A, A+1.5M NaBr as buffer B, and a linear gradient from 0 to 40% of buffer B in 40 minutes at a flow rate of 3 mL/min. The retention times of the oligonucleotide-peptide conjugate and the starting oligonucleotide were 14.5 and 23.5 min, respectively. Stirring with the first portion of the peptide for 45 minutes gave the desired conjugate in ca. 30% yield. Addition of the second portion of the peptide (0.5 equivalent) followed by stirring for 1 hour yielded 80% of the conjugate. The yield of the conjugation did not increase after incubation of the reaction mixture overnight. The reaction mixture was diluted with water (300 mL), and the conjugate was purified by ion-exchange chromatography on a MonoQ column (Pharmacia, 10×100 mm) using 0.1M NH$_4$OAc and 2M urea in 30% aqueous MeCN as buffer A, A+1.5M NaBr as buffer B, and a linear gradient from 0 to 40% of buffer B for 40 minutes at a flow rate of 4 mL/min. For each purification, 0.7 mmol of the conjugate was loaded onto the column. The SEQ ID No. 1 (13920-3'-Antp) conjugate was eluted at 30 minutes. The collected fractions were diluted with water (6 volumes) and desalted on Zorbax 300SB-C3 column (9.4×250 mm) as described above. The SEQ ID No. 1 (13920-3'-Antp) conjugate obtained (250 OD, 1.39 mmol, 60%) was 95% pure according to the analysis by reversed phase HPLC. ESMS: 9988.8 (expected), 9988.2 (found).

Example 5
Synthesis of SEQ ID No. 2 3'-Antp on 2500 OD Scale

Activated SEQ ID No. 2 (16518-3'-S—SPy) oligonucleotide (2590 OD, 13.2 mmol) in HPLC buffer (70 mL) was diluted with 1M KCl (33 mL), 2M urea and 0.1M NH$_4$OAc in 30% aqueous MeCN, (165 mL), diisopropylethylamine (400 mL), MeCN (50 mL), and water (4 mL). The solution was degassed, and the flask was filled with argon. Aqueous Antp-SH peptide (0.5 equivalent, 2.2 mL, 6.6 mmol, 10 mg/mL) was slowly added, and the mixture was stirred for 45 minutes at ambient temperature. This was followed by addition of the peptide (0.5 equivalent) and stirring the reaction mixture for 1 hour. The reaction mixture was analyzed by ion-exchange HPLC under the conditions specified above to reveal the formation of the desired conjugate in 82% yield. The retention times of the oligonucleotide-peptide conjugate and the starting oligonucleotide were 13 and 20 min, respectively. The reaction mixture was concentrated in vacuum. The conjugate was purified in 2 injections by RP-HPLC on a Delta-Pak column (C4 300 Å, 15 mm 19×300 mm) using 0.1M NH$_4$OAc as buffer A, 80% aqueous MeCN as buffer B, and a linear gradient from 0 to 60% of buffer B in 60 minutes at a flow rate of 10 mL/min. The fractions were concentrated in vacuum and desalted on the same column.

The SEQ ID No. 2 (16518-3'-Antp) conjugate obtained (1675 OD, 64%) was more than 98% pure according to the analysis by ion exchange and reversed phase HPLC. ESMS: 10070.8 (expected), 10070.4 (found).

Example 6
Preparation of SEQ ID No. 16 (102578-3'-RGD)

An oligonucleotide (SEQ ID No. 6 102578-SSPy) (530 OD, 2.95 mmol) in HPLC buffer (50 mL) was mixed with 1M KCl (6 mL), MeCN (4 mL), urea (3.6 g), and diisopropylethylamine (300 mL) to form a homogeneous solution. The solution was degassed, and the flask was filled with argon. An aqueous RGD-SH peptide (6.37 nmol/µL, 10 mg/mL) was slowly added in portions, first 1 equivalent (2.95 umol, 463 µL,), then two portions of 0.5 eq (231 µL) each, and finally 0.4 eq (185 µL) was added. After each portion was added, the reaction was stirred for 1 hour and analyzed by ion exchange HPLC using the column and the buffers specified above and a linear gradient from 0 to 30% of buffer B in 50 minutes at a flow rate of 3 mL/min. The conjugate was eluted initially as a shoulder on the peak of the starting oligonucleotide (retention time 31.5 min). With the excess peptide added, the conjugate became a major peak although more than 40% of the starting material remained unreacted. In addition, a side product which eluted at 45 minutes was formed in ca. 20% yield. Heating the reaction mixture overnight at 40° C. did not improve the product distribution.

The excess of unreacted oligonucleotide was quenched by adding MeCN (60 mL) and hexanethiol (10 mM in MeCN, 600 mL, 6 mmol, 2 equivalents) followed by stirring for 2 hours. The reaction mixture was concentrated in vacuum and purified in 1 mmol portions per run on a MonoQ column (Pharmacia, 10×100 mm) using 0.1M $NH_4OAc$, 2M urea, 30% MeCN as buffer A, A+1.5M NaBr as buffer B, and a linear gradient from 0 to 45% of buffer B in 50 minutes at a flow rate of 4 mL/minute. The peptide- and hexyl-conjugates of the oligonucleotide were co-eluted at 26 minutes. The fractions were concentrated in vacuum and re-purified on a Delta Pak C18 column (7.8×300 mm, 300 Å, 15 mm) using 0.1M $NH_4OAc$ as buffer A, 80% aqueous MeCN as buffer B, and a linear gradient from 0 to 40% of buffer B in 50 minutes at a flow rate of 5 mL/min. The RGD- and hexyl-oligonucleotide conjugates were eluted at 30 and 40 min, respectively. The conjugate was desalted by RP-HPLC. The SEQ ID No. 6 (102578-3'-RGD) conjugate obtained (330 OD, 62%) was 75% pure according to the analysis by LC-MS. ESMS: 8779 (expected), 8778 (found). FW of 20×$Na^+$, 1×$OAc^-$ salt 9292 Da.

Example 7
Synthesis of Oligonucleotide-Tat Peptide Conjugates

The Tat peptide was provided by the Center for Molecular Imaging Research, Massachusetts general hospital. The 20-mer oligonucleotide phosphorothioate 2'-MOE gapmers were synthesized on ABI 380B DNA synthesizer on a 25 mmol scale. 3'-Thiol-modifier C3 S—S CPG (Glen Research) was used to introduce a thiol group at the 3'-terminus of oligonucleotides.

Oligonucleotide Activation

HPLC purified, 3'-hydroxypropyl disulfide modified oligonucleotide (1000 OD) was treated with DTT (5 mL, 0.25M in 0.1M $NaHCO_3/Na_2CO_3$ buffer, pH 9.0) for 2 hours at ambient temperature. The reaction mixture was directly loaded onto an HPLC column (Waters Bondapak HC18HA, 25 mm×100 mm, 300 Å, 40 μ). The column was eluted using 0.1M $NH_4OAc$ as buffer A, 80% aqueous MeCN as buffer B, and a linear gradient from 0 to 60% of B in 60 minutes at a flow rate 15 mL/minute. The fractions containing the 3'-mercaptopropyl oligonucleotide were collected directly into a solution of 2,2'-dithiodipyridine (20 mg) in MeCN (2 mL) and 100 mL 0.8 mM diisopropylethylamine. The reaction mixture was kept for 2 hours and concentrated in vacuo. The excess 2,2'-di-pyridyldisulfide was extracted with ethylacetate. The activated oligonucleotide was purified by RP-HPLC using the conditions specified above. Activated oligonucleotides were be stored at 4° C. for short periods of time.

Example 8
Tat-Peptide Linked Oligonucleotide (SEQ ID No. 2, 16518–3'-tat)

Activated SEQ ID No. 2 (16518-3'-SSPy) oligonucleotide (600 OD, 3.1 mmol) in HPLC buffer (3.5 mL) was diluted with 1M KCl (7.5 mL), 4.5 g urea (74.9 mmol), 5M $NH_4OAc$ (1.5 mL), a solution of 0.1M $NH_4OAc$, 2M urea, 30% MeCN (37.5 mL), MeCN (22.5 mL), water (2.5 mL) and 0.8 mM diisopropylethylamine (93.8 mL). The resulting solution was degassed and the flask was filled with Argon. Aqueous Tat-SH peptide (1 equivalent, 562 mL, 3.1 mmol 10 mg/mL) was added slowly with stirring. The reaction mixture was left overnight and then analyzed by ion exchange HPLC on a Poros DNA Q column (4.6 mm×50 mm) using 0.1M $NH_4OAc$, 2M urea, 30% MeCN as buffer A, buffer A+1.5M NaBr as buffer B and a linear gradient from 0 to 50% of buffer B in 40 min, flow rate 2.5 mL/min. The ion exchange HPLC revealed incomplete conversion into product, therefore 0.25 equivalent of Tat-SH peptide was further added and the reaction mixture left for 2 hours. The retention times of the oligonucleotide-peptide conjugate and the starting oligonucleotide were 14.2 and 23.5 min. The conjugate was purified by ion exchange HPLC on a Mono Q column (Pharmacia, 10×100 mm), buffer A: 0.1M $NH_4OAc$, 2M urea, 30% MeCN; buffer B: buffer A+1.5M NaBr, flow rate 3 mL/min, in a linear gradient from 0 to 50% B in 60 min.) For each purification 0.26 mmol of the conjugate was loaded on the column. The conjugate was diluted twice with water before loading on the column. The 16518-3'-Tat conjugate was eluted at 36–44 min. The collected fractions were combined, evaporated in vacuo and desalted twice on Zorbax 300SB-C3 column (9.4×250 mm) in Na+ form and once on a Sephadex G25 column. The Tat-conjugated oligomer (SEQ ID No. 2, 16518–3'-Tat) obtained (275 OD, 1.4 mmol, 45%) was more than 99% pure according to the analysis by reversed phase HPLC and ion exchange HPLC. ESMS: 9201.5 (expected), 9199.5 (found). FW of 20×x Na, 8×$OAc^-$ salt 10105.2 Da.

Example 9
Tat-Peptide Linked Oligonucleotide (SEQ ID No. 1, 13920–3'-Tat)

Activated oligonucleotide (SEQ ID No. 1, 13920–3'-SSPy 368 OD, 2.04 mmol) in HPLC buffer (10.73 mL) was diluted with 1M KCl (4.6 mL), 2.76 g urea (45.9 mmol), 5M $NH_4OAc$ (0.92 mL), a solution of 0.1M $NH_4OAc$, 2M urea, 30% MeCN (23 mL), MeCN (6.9 mL) and 0.8 mM diisopropylethylamine (57.5 mL). The obtained solution was degassed and the flask filled with Argon. Aqueous Tat-SH peptide (1 equivalent, 22.7 mg/mL, 162.8 mL, 2.04 mmol) was added slowly with stirring. The reaction mixture was left for 2 hours and then analyzed by ion exchange HPLC on a Poros DNA Q (4.6 mm×50 mm) using 0.1M $NH_4OAc$, 2M urea, 30% MeCN as buffer A, buffer A+1.5M NaBr as buffer B and a linear gradient from 0 to 50% B in 40 min, flow rate 2.5 mL/minute. The ion exchange HPLC revealed incomplete conversion into product, therefore 0.25 equivalent of Tat-SH peptide was further added and the reaction mixture left for 1 hour. Ion exchange HPLC still revealed incomplete conversion into product and an additional 0.25 equivalent of Tat-SH peptide was added. The reaction mixture was left overnight. The conjugate was purified by ion exchange HPLC on a Mono Q column (Pharmacia, 10×100 mm), using 0.1M $NH_4OAc$, 2M urea, 30% MeCN as buffer A, buffer A+1.5M NaBr as buffer B, flow rate 3 mL/min and a linear gradient from 0 to 50% B in 70 min. For each purification 0.22 mmol of the conjugate was diluted twice with water before loading on the column. The peptide linked oligomer (SEQ ID No. 1, 13920–3'-Tat) eluted at 46–52 min. The collected fractions were combined, evaporated in vacuo and desalted on Zorbax 300SB-C3 column (9.4×250 mm) in $Na^+$ form.

The peptide linked oligomer (SEQ ID No. 1, 13920–3'-Tat) obtained (113 OD, 0.6 mmol, 31%) was 98% pure according to the analysis by reversed phase HPLC and ion exchange HPLC. ESMS: 9123.4 (expected), 9121.5 (found). FW of 20×Na, 8×$OAc^-$ salt 10027.3 Da.

Example 10
4-[(4,4'-Dimethoxytrityl)oxy]butyric acid, triethylammonium salt

4-[(4,4'-dimethoxtrityl)oxy]butyric acid, triethylammonium salt (4)

A solution of 4,4'-dimethoxytrityl chloride (695 mg, 2.05 mmol) and 4-hydroxybutyric acid (208 mg, 2.0 mmol) in anhydrous Py (20 mL) was stirred overnight and concentrated to an oil in vacuo. The residue was dissolved in a mixture of MeOH and $CH_2Cl_2$ (95:5, v/v; 200 mL) and washed with 2 M aqueous triethylammonium acetate (5×20 mL). The organic solution was evaporated, re-dissolved in $CH_2Cl_2$, dried over $Na_2SO_4$, and evaporated to give crude 4 in a quantitative yield (1016 mg).

Example 11
Preparation of Solid Support (Solid Support 2, FIG. 1)

Dithiodiglycolic acid 1 (360 mg, 2.0 mmol) and N,N'-diisopropylcarbodiimide (504 mg, 4.0 mmol) were added to a suspension of long chain amino alkyl CPG (2.0 g, 0.22 mmol) in anhydrous Py (20 mL). The suspension was shaken overnight and filtered. The solid support was washed with Py (4×20 mL) and THF (3×20 mL) and treated with a mixture of acetic anhydride (1.0 mL) and N-methylimidazole (2.0 mL) in anhydrous THF (18 mL) for 30 min. Finally, the solid support was extensively washed with THF (5×20 mL) and dried in vacuo.

Example 12
Preparation of Solid Support (Solid Support 3, FIG. 1)

The solid support prepared in Example 11 (2 g) was treated with 0.5 M dithiodthreithol in 50% aqueous MeCN (10 mL) for 2 hours. The suspension was filtered and briefly washed with 50% aqueous MeCN (5×20 mL) and THF (3×20 mL). The resulting solid support obtained was dried in vacuo and used immediately.

Example 13
Loading the Solid Support (Solid Support 5, FIG. 1)

A suspension of the solid support prepared in Example 12 (2.0 g) in Pyridine (10 mL) was treated with 4-[(4,4'-dimethoxytrityl)oxy]butyric acid, triethylammonium salt (1016 mg, 2.0 mmol) and N,N'-diisopropylcarbodiimide (504 mg, 4.0 mmol). The suspension was shaken overnight and filtered. The solid support was washed with Pyridine (4×mL) and THF (3×20 mL) and treated with a mixture of acetic anhydride (1.0 mL) and N-methylimidazole (2.0 mL) in anhydrous THF (18 mL) for 30 minutes. The solid support was extensively washed with THF (5×20 mL) and dried in vacuo. As determined by the dimethoxytrityl assay, the loading of the resulting solid support was 35–36 $\mu$mol g$^{-1}$.

Example 14
Oligonucleotide Synthesis

Oligonucleotide phosphorothioate 2'-O-MOE gapmers were synthesized on an ABI 380B DNA synthesizer on a 25 umol scale using standard phosphoramidite protocols and commercially available reagents.

A representative list of oligonucleotides that were prepared include:

Conversion of ISIS oligomer numbers:
SEQ ID No. 1=13920;
SEQ ID No. 2=16518;
SEQ ID No. 3=16009;
SEQ ID No. 4=11159;
SEQ ID No. 5=15493;
SEQ ID No. 6=102578.

Example 15
General Procedure for Cleaving and Deprotecting 3'-Cystamine Derivatized Oligonucleotides (Formula 7, FIG. 1)

A solid support-bound oligonucleotide (Formula 6, FIG. 1) was shaken with 0.5 to 1.0 M aqueous cystamine (free base, 0.5 mL per 1 $\mu$mol of the solid support) for 1–3 hours at room temperature. The resulting solution was filtered, concentrated in vacuo to ca. 25% of the initial volume, and diluted with concentrated aqueous ammonium hydroxide (2 mL per 1 $\mu$mol of the solid support). The solution was kept for 6 to 8 hours at 55° C. and evaporated to give crude cleaved oligonucleotide having a linking moiety (Formula 7, FIG. 1). The crude oligomeric compound was purified by HPLC on a DeltaPak C18 column (7.8×300 mm 300 Å, 15 $\mu$). The column was eluted using 0.1 M NH$_4$OAc as buffer A, 80% aqueous MeCN as buffer B, and linear gradient from 0 to 45% of B in 60 min at a flow rate 5 mL min$^{-1}$ thereby providing the title oligonucleotide.

Example 16
General Procedure for Activation of Oligonucleotides

HPLC purified, 3'-cystamine modified oligonucleotides (Formula 7, FIG. 1, 1000 OD) were treated with DTT (5 mL, 0.25 M in 0.1 M NaHCO$_3$/Na$_2$CO$_3$ buffer, pH 7.5) for 2 hours at ambient temperature. The reaction mixture was directly loaded onto an HPLC column (Delta-Pak C18, 25×100 mm, 300 Å, 15 $\mu$). The column was eluted using 0.1 M NH$_4$OAc as buffer A, 80% aqueous MeCN as buffer B, and linear gradient from 0 to 45% of B in 60 min at a flow rate 15 mL min$^{-1}$. The fractions containing the 3'-mercaptopropyl oligonucleotide were collected directly to a solution of 2,2'-dithiodipyridine (20 mg) in MeCN (2 mL). The reaction mixture was kept for 2 hours and concentrated in vacuum. The excess 2,2'-dithiodipyridine was extracted with ethyl acetate (2×10 mL). The activated oligonucleotide was purified by HPLC using the conditions specified above. Activated oligonucleotides were stored for a short periods of time in a refrigerator prior to use.

Example 17
General Procedure for Conjugation with Antennapedia Peptide

A solution of an activated oligonucleotide (Example 16, 8 OD mL$^{-1}$ in 20–30% aq MeCN, 0.1 M KCl, 1 M urea, 0.1 M NH$_4$OAc, 1 $\mu$M diisopropylethylamine) was degassed, and the flask was filled with argon. Antennapedia peptide (1 eq, 3 nmol $\mu$L$^{-1}$ in freshly boiled and cooled water) was

| SEQ ID No. | Sequence | target | |
|---|---|---|---|
| 1 | TCC gtc* atc* gc*t CCT CAG GG | (P = S) | H-ras (human) |
| 2 | AGC TTC ttt gca ca TGT AAA | (P = S) | MDM-2 (human) |
| 3 | CTA CG c*tt tc*c* ac*g c* ACA GT | (P = S) | Bcl-x (human) |
| 4 | TCT GAG TAG CAG AGG AGC Tc* | (P = S) | ICAM-1 (human) |
| 5 | c*c*g gta c*c*c* CAG GTT CTT CA | (P = S) | A-raf kinase (mouse) |
| 6 | GAG CG tct ctt cct t CTG GA | (P = S) | PECAM (mouse) | c* = No 5-Me for this deoxy C; uppercase letters = 2'-O-MOE and lowercase letters are 2'-deoxynucleosides.

added slowly in 2 portions under gentle mixing. When a local precipitation was observed, the addition was stopped, and the mixture was stirred until the precipitate was dissolved. The reaction mixture was kept for 1–2 hours at ambient temperature. As judged by ion-exchange HPLC, addition of peptide (1 eq) results in 70–80% conversion of the starting oligonucleotide. After evaporation of MeCN, a peptide-oligonucleotide conjugate was purified by RP-HPLC on Delta Pak C4 column (19×300 mm, 300 A, 15 um) using 0.1 M $NH_4OAc$ as buffer A, 80% aqueous MeCN as buffer B, and a linear gradient from 0 to 60% of in 40 min at a flow rate of 10 mL $min^{-1}$. Desalting of the oligonucleotide-peptide conjugate was performed by RP-HPLC on Zorbax C3 column to furnish the product as either $NH_4^+$ or $Na^+$ salt.

Example 18
300 OD Scale Scale Peptide Linked Oligonucleotide Synthesis (Preparation of SEQ ID No. 1, 13920–3'-Antp)

Activated oligonucleotide (SEQ ID No. 1, 13920–3'-S—SPy, 300 OD, 1.65 $\mu$mol) in HPLC buffer (25 mL) is diluted with 1 M KCl (10 mL), 2 M urea and 0.1 M $NH_4OAc$ in 30% aq MeCN (50 mL), diisopropylethylamine (125 $\mu$L), and MeCN (20 mL). The obtained solution is degassed, and the flask is filled with argon. Aqueous Antp-SH peptide (10 mg $mL^{-1}$, 1 eq, 1.65 $\mu$mol) is added slowly under stirring. The reaction mixture is stirred for 2 hours to yield the conjugate according to ion exchange HPLC on a Poros DNA Q column (4.6×50 mm) using: 0.1 M $NH_4OAc$, 2 M urea, 30% MeCN as buffer A, A+1.5 M NaBr as buffer B, and a linear gradient from 0 to 40% of buffer B in 40 min at a flow rate of 3 mL $min^{-1}$. The reaction mixture is diluted with water (250 mL), and the conjugate is purified by ion-exchange chromatography on a MonoQ column (Pharmacia, 10×100 mm) using 0.1 M $NH_4OAc$, 2 M urea, 30% MeCN as buffer A, A+1.5 M NaBr as buffer B, and a linear gradient from 0 to 40% of buffer B in 40 min at a flow rate of 4 mL $min^{-1}$. The 13920-3'-Antp conjugate is eluted at about 30 minutes. The collected fractions are diluted with water (6 volumes) and desalted on Zorbax 300SB-C3 column (9.4×250 mm) as described above. The 13920-3'-Antp conjugate (Isis-136842, 180 OD, 0.99 mmol, 60%) is 95% pure according to the analysis by reversed phase HPLC. ESMS: 9988.8 (expected), 9988.2 (found). FW of 20×$Na^+$, 7×$OAc^-$ salt 10768.8 Da

Example 19
Synthesis of cyclic RGD peptides for targeting of integrin-expressing cells ($NH_2$-Arg -Gly-Asp-Pro-Tyr-Cys-Gly-COOH) (SEQ ID NO 9)

The Pro in the middle of the sequence induces a Beta-turn and the length is optimal for the cyclization via the formation of an amide bond between Arg and Gly. The peptide was synthesized following standard Fmoc peptide methodologies. The peptide was cleaved from the resin without the deprotection of the side chains. The protections were Pmc for the Arg (pentamethyl chroman-6-sulfonyl), tButyl for the Asp and Tyr, and Trityl for the Cys. For the cyclization, 5 umoles of RGDPYCG (4 mg) were taken in 5.2 mL of $CH_2Cl_2$ giving a 1 mM concentration. DIEA (10 $\mu$moles) and DPPA (25 $\mu$moles, diphenylphosphoryl azide, Sigma) were added and the mixture is stirred at room temperature. The reaction is followed by HPLC with a C4-column (Vydac, protein c4-column, 1 ml/min, solvent A: H20 TFA 0.1%; B: CH3CN, gradient: 0 to 90% B, 40 min). The cyclic peptide was purified using a semi-preparative C4 column.

The peptide deprotection was carried out following standard peptide protocols.

Example 20

A representative list of peptides that were conjugated to oligomeric compounds using methods of the present invention include:

| SEQ ID No. | SEQUENCE |
|---|---|
| 7 | Lev-Z-GG-RQIKIWFQNRRMKWKK |
| 8 | C-Z-GG-RQIKIWFQNRRMKWKK |
| 9 | cyclic RGDPYCG |
| 10 | cyclic GNGRPYCG |
| 11 | cyclic GRGDPYCG |
| 12 | CZWFRRRR |
| 13 | CZWFRRRRRR |
| 14 | CZWFRRRRRRRRR |
| 15 | GRKKRRGRRRGWC |
| 16 | 3-mercaptopropionyl-(Gaba)-GGACDCRGDCFCG-amide (Random oxidation of Cys residues under dilute alkaline conditions; intermolecular aggregates are very likely to be formed) |
| 17 | 3-mercaptopropionyl-(Gaba)-GGAC*DCRGDCFC*G-amide (Defined oxidation between Cys residues) * shows where cysteines are crosslinked. (Z = $\gamma$-aminobutyric acid) |

Example 21
Amide Linker Attached to CPG

2-Hydroxyethyl disulfide (Aldrich, 38047-4) is treated with 0.5 equivalent of dimetroxytrityl chloride and pyridine under high dilution conditions. The resultant product is treated with p-toluene sulfonic acid/pyridine. The resultant tosylate is treated with $LiN_3$ in DMSO and the resultant azide is reduced with $Ph_3P$ to give the amino compound (DMTO-$CH_2CH_2$—S—S—$CH_2CH_2NH_2$.) This compound is then condensed with 4-hydorxymethyl benzoic acid (Fluka-Aldrich 55616) with dicyclohexylcarbodiimide in THF to give the amide containing linker compound wich is condensed with CPG following the procedure described by Bayer, et al., Z. Naturforsch, 1995, 50b, 1096–1100.

Example 22
Carbamate Linker Attached to CPG

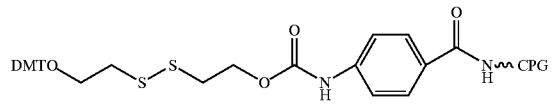

2-Hydroxyethyl disulfide (Aldrich, 38047-4) is treated with 0.5 equivalent of dimetroxytrityl chloride and pyridine under high dilution conditions. The resultant compound is treated with disuccinimidyl carbonate under the conditions described by Manoharan, et al, (J. Org. Chem. 65, 6468–6472, 1999.) The resultant carbonate is treated with 4-(amonimethyl) benzoic acid which is condensed with amino linked CPG to give the linked solid support following the procedure of described by Bayer, et al., *Z. Naturforsch,* 1995, 50b, 1096–1100.

Example 23
Thioureido Linker Attached to CPG

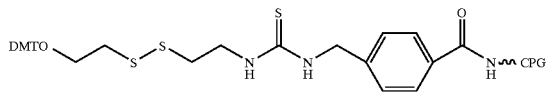

DMTO-CH$_2$CH$_2$—S—S—CH$_2$CH$_2$—NH$_2$ (Example 21) is condensed with p-isothiocyanatomethyl benzoic acid described by Grabenko, et al., *Zh. Org. Khim.* 1997, 8, 528–531. The resulting compound is coupled to controlled pore glass using the procedure described by Bayer, et al., *Z. Naturforsch,* 1995, 50b, 1096–1100.

Example 24
Ureido Linker Attached to CPG

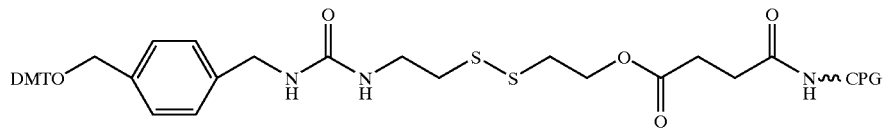

4-(Aminomethyl)-benzenemethanol, is prepared according to the method of Gavin, J A. et al., *J. Org. Chem.,* 1998, 63, 7663–7669. The compound is protected with ethyltrifluoroacetate and further treated with 1.0 equivalent of dimethoxytrityl chloride and pyridine. The resultant product is treated with ammonium hydroxide in pyridine to give the free amine compound and further treated with with disuccinimidyl carbonate under the conditions described by Manoharan, et al, *J. Org. Chem.,* 1999, 65, 6468–6472. The resultant carbonate is treated with the amino compound (HO-CH$_2$CH$_2$—S—S—CH$_2$CH$_2$NH$_2$) prepared in Example 21 above. The resulting compound is succinylated and condensed with amino linked CPG using the procedures described by Bayer, et al., *Z. Naturforsch,* 1995, 50b, 1096–1100, to give the desired compound attached to CPG.

Example 25
Thioureido Linker Attached to CPG

An aqueous suspension of amino compound (HO—CH$_2$CH$_2$—S—S—CH$_2$CH$_2$NH$_2$) is treated with carbon disulfide in sodium hydroxide solution and then ethylchloroformate (see: Finar, et al., Organic Chemistry Vol I, Longman, 1973, London) to give the isothiocyanate derivative. The isothiocyanate derivative is treated with 4-(aminomethyl)-O-DMT-benzenemethanol, as prepared in Example 23, under basic conditions to give the thiourea compound. The thiourea compound compound is succinylated and condensed with amino linked CPG using the procedures described by Bayer, et al., *Z. Naturforsch,* 1995, 50b, 1096–1100, to give the desired compound attached to CPG.

Example 26
4-[(4,4'-dimethoxytrityl)oxy]butyric acid, triethylammonium salt

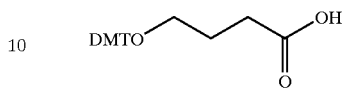

A solution of 4,4'-dimethoxytrityl chloride (6.77 g, 20.0 mmol) and 4-hydroxybutyric acid (252 g, 20.0 mmol) in anhydrous Py (25 mL) was stirred overnight and concentrated to an oil in vacuo. The residue was dissolved in ethyl acetate (200 mL) and washed with water and 2 M aqueous triethylammonium acetate (5×20 mL). The organic solution was evaporated, re-dissolved in CH$_2$Cl$_2$, dried over Na$_2$SO$_4$, and evaporated to give crude triethylammonium 4-[(4,4'-dimethoxytrityl)oxy]butyrate (9.36 g).

Example 27
Thioglycolyl Derivatized CPG

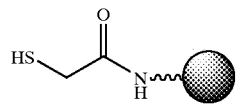

Dithiodiglycolic acid (1.26 g, 6.91 mmol) and N,N'-diisopropylcarbodiimide (1.81 g, 14.0 mmol) were added to a suspension of long chain amino alkyl CPG (6.0 g, 0.691 mmol) in anhydrous Py (40 mL). The suspension was shaken overnight and filtered. The solid support was washed with Py (4×20 mL) and THF (3×20 mL) and treated with a mixture of acetic anhydride (2.0 mL) and

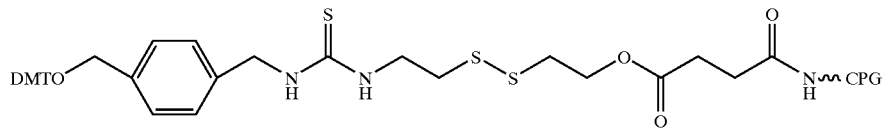

N-methylimidazole (4.0 mL) in anhydrous THF (36 mL) for 30 min. Finally, the solid support was extensively washed with THF (5×20 mL) and dried in vacuo.

The resulting solid support (6.0 g) was then treated with 0.15 M dithiodthreithol in 50% aqueous MeCN (30 mL) for 2 h. The suspension was filtered and briefly washed with 50% aqueous MeCN (5×20 mL) and MeCN (3×20 mL). The thioglycolyl-derivatized CPG obtained was dried in vacuo and used in the following step as soon as possible.

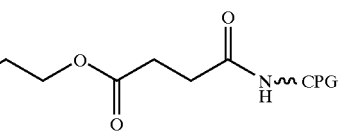

Example 27
2-[4-[(4,4'-dimethoxytrityl)oxy]butyrylthio]acetyl derivatized CPG

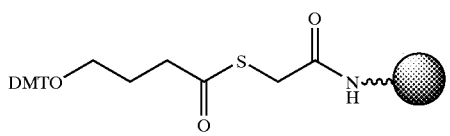

A suspension of solid support (6.0 g) in Py (40 mL) was treated with triethylammonium 4-[(4,4'-dimethoxytrityl) oxy]-butyrate (2.94 g, 4.84=mol) and N,N'-diisopropylcarbodiimide (610 mg, 4.84 mmol). The suspension was shaken overnight and filtered. The solid support was washed with Py (4×20 mL) and THF (3×20 mL) and treated with a mixture of acetic anhydride (2.0 mL) and N-methylimidazole (4.0 mL) in anhydrous THF (36 mL) for 30 min. Finally, the solid support was extensively washed with THF (5×20 mL) and dried in vacuo. As determined by the dimethoxytrityl assay, the loading of the solid support 5 was 84–87 mmol g$^{-1}$.

Example 28
2-[2-(4,4'-Dimethoxytrityloxy)ethoxy]acetic acid, triethylammonium salt

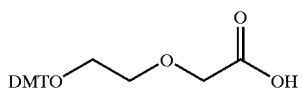

A solution of 2-(2-hydroxyethoxy)acetic acid prepared as desctibed in (Snapp, Thomas C., Jr.; Blood, Alden E. Ether diester derivatives of p-dioxanone. U.S. (1975), 4 pp. U.S. Pat. No. 3,929,847) (7.45 g, 22 mmol) in pyridine (20 mL) is treated with 4,4'-dimethoxytrityl chloride (10.16 g, 30 mmol) overnight at room temperature and concentrated to an oil in vacuo. The residue is dissolved in a mixture of MeOH and CH$_2$Cl$_2$ (95:5, v/v; 200 mL) and washed with 2 M aqueous triethylammonium acetate (5×20 mL). The organic solution is evaporated, re-dissolved in CH$_2$Cl$_2$, dried over Na$_2$SO$_4$, and evaporated to give crude triethylammonium 2-[2-(4,4'-dimethoxytrityloxy) ethoxy] acetate in quantitative yield (10.47 g).

Example 29
2-[2-[2-(4,4'-Dimethoxytrityloxy)ethoxy]acetylthio]acetyl derivatized CPG

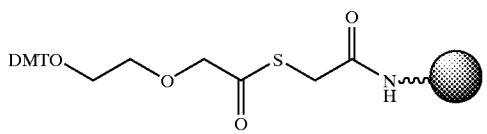

Thioglycolyl-derivatized CPG (2.0 g) prepared as described above is suspended in Py (10 mL) and treated with 4 (1047 mg, 2.0 mmol) and N,N'-diisopropylcarbodiimide (505 mg, 4.0 mmol). The suspension is shaken overnight and filtered. The solid support is washed with Py (4×20 mL) and THF (3×20 mL) and treated with a mixture of acetic anhydride (1.0 mL) and N-methylimidazole (2.0 mL) in anhydrous THF (18 mL) for 30 min. Finally, 2-[2-[2-(4,4'-dimethoxytrityloxy)-ethoxy]acetylthio] acetyl-derivatized CPG is extensively washed with THF (5×20 mL) and dried in vacuo.

Example 30
3-[2-[2-(4,4'-Dimethoxytrityloxy)ethoxy]ethoxy]propionic acid, triethylammonium salt

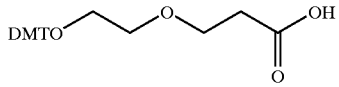

A solution of 2-(2-hydroxyethoxy)acetic acid prepared as desctibed in (Huskens, J.; Peters, J. A.; Van Bekkum, H. The addition of hydroxyl compounds to unsaturated carboxylic acids homogeneously catalyzed by lanthanide(III). Tetrahedron (1993), 49(15), 3149–3164) (1.34 g, 10 mmol) in pyridine (20 mL) is treated with 4,4'-dimethoxytrityl chloride (3.73 g, 11 mmol) overnight at room temperature and concentrated to an oil in vacuo. The residue is dissolved in a mixture of MeOH and CH$_2$Cl$_2$ (95:5, v/v; 200 mL) and washed with 2 M aqueous triethylammonium acetate (5×20 mL). The organic solution is evaporated, re-dissolved in CH$_2$Cl$_2$, dried over Na$_2$SO$_4$, and evaporated to give crude triethylammonium 3-[2-[2-(4,4'-dimethoxytrityloxy) ethoxy] propionate in quantitative yield (5.37 g).

Example 31
2-[3-[2-[2-(4,4'-Dimethoxytrityloxy)ethoxy]propionylthio] acetyl derivatized CPG

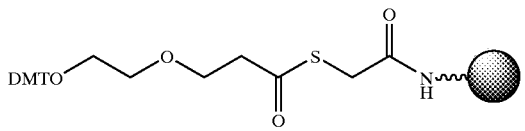

Thioglycolyl-derivatized CPG (2.0 g) prepared as described above is suspended in Py (10 mL) and treated with triethylammonium 3-[2-[2-(4,4'-dimethoxytrityloxy) ethoxy] propionate (1075 mg, 2.0 mmol) and N,N'-diisopropylcarbodiimide (504 mg, 4.0 mmol). The suspension is shaken overnight and filtered. The solid support is washed with Py (4×20 mL) and THF (3×20 mL) and treated with a mixture of acetic anhydride (1.0 mL) and N-methylimidazole (2.0 mL) in anhydrous THF (18 mL) for 30 min. Finally, the product, 2-[3-[2-[2-(4,4'-Dimethoxytrityloxy)ethoxy] propionylthio] acetyl-derivatized CPG, is extensively washed with THF (5×20 mL) and dried in vacuo.

Example 32
4-Mercaptobenzoyl Derivatized CPG

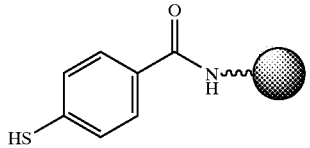

Commercial (4,4'-dithiobis)benzoic acid (674 mg, 2.2 mmol) and N,N'-diisopropylcarbodiimide (555 mg, 4.4 mmol) were added to a suspension of long chain amino alkyl CPG (4.0 g, 0.44 mmol) in anhydrous Py (30 mL). The suspension was shaken overnight and filtered. The solid support was washed with Py (4×50 mL) and THF (3×50 mL) and treated with a mixture of acetic anhydride (2.0 mL) and N-methylimidazole (4.0 mL) in anhydrous THF (36 mL) for 30 min. Finally, the solid support was extensively washed with THF (5×50 mL) and dried in vacuo.

The resulting solid support (4 g) was then treated with 0.5 M dithiothreithol in a mixture of water, MeCN, and triethylamine (40:20:40; 20 mL) for 2 h. The suspension was filtered and briefly washed with 50% aqueous MeCN (5×30 mL) and THF (3×30 mL). The product, 4-mercaptobenzoyl-derivatized CPG, was dried in vacuo and used in the following step as soon as possible.

Example 33

4-[4-[(4,41-dimethoxytrityl)oxy]butyrylthio]benzoyl derivatized CPG

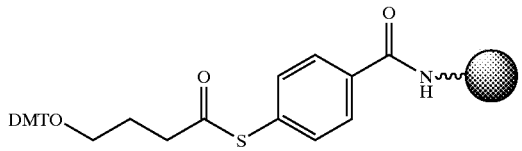

A suspension of 4-mercaptobenzoyl derivatized CPG (4.0 g) in Py (20 mL) was treated with triethylammonium 4-[(4,4'-dimethoxytrityl)oxy]butyrate (1117 mg, 2.2 mmol) and N,N'-diisopropylcarbodiimide (555 mg, 4.4 mmol). The suspension was shaken overnight and filtered. The solid support was washed with Py (4×40 mL) and THF (3×40 mL) and treated with a mixture of acetic anhydride (2.0 mL) and N-methylimidazole (4.0 mL) in anhydrous THF (36 mL) for 30 min. Finally, the solid support was extensively washed with THF (5×40 mL) and dried in vacuo. As determined by the dimethoxytrityl assay, the loading of 4-[4-[(4,4'-dimethoxytrityl)-oxy]butyrylthio]benzoyl derivatized CPG was 70–71 mmol g$^{-1}$.

Example 34

3-Mercaptobenzoyl Derivatized CPG

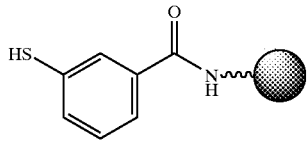

Commercial 3,3'-dithiobis-benzoic acid (674 mg, 2.2 mmol) and N,N'-diisopropylcarbodiimide (555 mg, 4.0 mmol) were added to a suspension of long chain amino alkyl CPG (4.0 g, 0.44 mmol) in anhydrous Py (30 mL). The suspension was shaken overnight and filtered. The solid support was washed with Py (4×40 mL) and THF (3×40 mL) and treated with a mixture of acetic anhydride (2.0 mL) and N-methylimidazole (4.0 mL) in anhydrous THF (36 mL) for 30 min. Finally, the solid support was extensively washed with THF (5×40 mL) and dried in vacuo.

The resulting solid support (4 g) was then treated with 0.5 M dithiothreithol in a mixture of water, MeCN, and triethylamine (40:20:40; 20 mL) for 2 h. The suspension was filtered and briefly washed with 50% aqueous MeCN (5×40 mL) and THF (3×40 mL). The product, 3-mercaptobenzoyl derivatized CPG was dried in vacuo and used in the following step as soon as possible.

Example 35
3-[4-[(4,4'-dimethoxytrityl)oxylacety]thio]benzoyl derivatized CPG

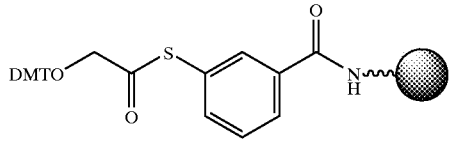

A suspension of 3-mercaptobenzoyl derivatized CPG (2.0 g, 0.22 mmol) in Py (10 mL) is treated with triethylammonium 4-[(4,4'-dimethoxytrityl)oxy]acetate prepared as described in (Hovinen, J; Guzaev, A.; Azhayev, A.; Lonnberg, H. Tetrahedron, 1994, 50(24), 7203–7218) (528 mg, 1.1 mmol) and N,N'-diisopropylcarbodiimide (278 mg, 2.2 mmol). The suspension is shaken overnight and filtered. The solid support is washed with Py (4×20 mL) and THF (3×20 mL) and treated with a mixture of acetic anhydride (1.0 mL) and N-methylimidazole (2.0 mL) in anhydrous THF (18 mL) for 30 min. Finally, 3-[4-[(4,4'-dimethoxytrityl)oxy]acetylthio]benzoyl derivatized CPG is extensively washed with THF (5×20 mL) and dried in vacuo.

Example 36
3-[4-[(4,4'-dimethoxytrityl)oxy]butyrylthio]benzoyl derivatized CPG

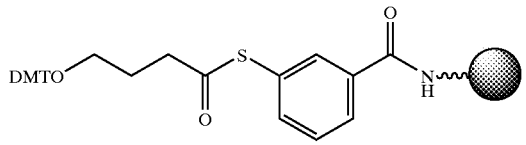

A suspension of 3-mercaptobenzoyl-derivatized CPG (4.0 g) in Py (20 mL) was treated with triethylammonium 4-[(4,4'-dimethoxytrityl)oxy]butyrate (1117 mg, 2.2 mmol) and N,N'-diisopropylcarbodiimide (555 mg, 4.4 mmol). The suspension was shaken overnight and filtered. The solid support was washed with Py (4×40 mL) and THF (3×40 mL) and treated with a mixture of acetic anhydride (2.0 mL) and N-methylimidazole (4.0 mL) in anhydrous THF (36 mL) for 30 min. Finally, the solid support was extensively washed with THE (5×40 mL) and dried in vacuo. As determined by the dimethoxytrityl assay, the loading of the product, 3-[4-[(4,4'-dimethoxytrityl)oxy]butyrylthio]benzoyl derivatized CPG, was 84–86 mmol g$^{-1}$.

Example 37
4-[[(4,4'-dimethoxytrityl)oxy]methyl]benzoic acid, triethylammonium salt

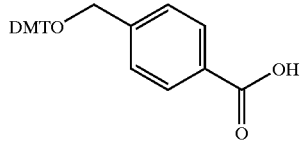

A solution of commercial 4-(hydroxymethyl)benzoic acid (1.52 g, 10.0 mmol) in pyridine (50 mL) is treated with 4,4'-dimethoxytrityl chloride (3.73 g, 11.0 mmol) overnight at room temperature and concentrated to an oil in vacuo. The residue is dissolved in a mixture of MeOH and CH$_2$Cl$_2$ (95:5, v/v; 200 mL) and washed with 2 M aqueous triethylammonium acetate (5×20 mL). The organic solution is evaporated, re-dissolved in $CH_2Cl_2$, dried over $Na_2SO_4$, and evaporated to give crude triethylammonium 4-[[(4,4'-dimethoxytrityl)oxy]methyl]-benzoate in quantitative yield (1016 mg).

Example 38
2-[4-[[(4,4'-dimethoxytrityl)oxy]methyl]benzoylthio] acetyl-derivatized CPG

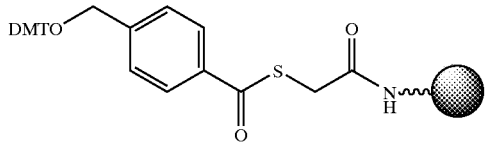

A suspension of thioglycolyl derivatized CPG prepared as described above (2.0 g) in Py (10 mL) is treated with triethylammonium 4-[[(4,4'-dimethoxytrityl)oxy]methyl] benzoate (611 mg, 1.1 mmol) and N,N'-diisopropylcarbodiimide (278 mg, 2.2 mmol). The suspension is shaken overnight and filtered. The solid support is washed with Py (4×20 mL) and THF (3×20 mL) and treated with a mixture of acetic anhydride (1.0 mL) and N-methylimidazole (2.0 mL) in anhydrous THF (18 mL) for 30 min. Finally, the product, 2-[4-[[(4,4'-dimethoxytrityl)oxy]methyl]benzoylthio]acetyl-derivatized CPG, is extensively washed with THF (5×20 mL) and dried in vacuo.

Example 38
2-[4-[[(4,4'-dimethoxytrityl)oxy]methyl]benzoylthio] benzoyl derivatized CPG

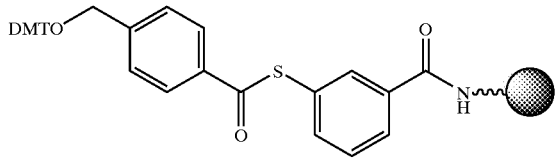

A suspension of 3-mercaptobenzoyl derivatized CPG prepared as described above (2.0 g) in Py (10 mL) is treated with triethylammonium 4-[[(4,4'-dimethoxytrityl)oxy] methyl]-benzoate (611 mg, 1.1 mmol) and N,N'-diisopropylcarbodiimide (278 mg, 2.2 mmol). The suspension is shaken overnight and filtered. The solid support is washed with Py (4×20 mL) and THF (3×20 mL) and treated with a mixture of acetic anhydride (1.0 mL) and N-methylimidazole (2.0 mL) in anhydrous THF (18 mL) for 30 min. Finally, the product, 2-[4-[[(4,4'-dimethoxytrityl) oxy]methyl]benzoylthio]benzoyl-derivatized CPG, is extensively washed with THF (5×20 mL) and dried in vacuo.

Example 39
Oligonucleotide $(TG)_2ctat_2c(tg)_2A_2T_2$ (SEQ ID NO: 20) activated with 3'-O-[3-[N-[2-[(2-pyridyl)dithio] ethyl] carbamoyl] propyl] thiophosphate group

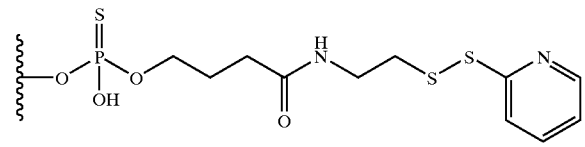

A solid support-bound oligonucleotide $(TG)_2ctat_2c(tg)_2 A_2T_2$ assembled on 2-[4-[(4,4'-dimethoxytrityl)oxy] butyrylthio]-acetyl derivatized CPG (60 mmol) was shaken with 1.0 M aqueous cystamine (15 mL) for 3 h at room temperature. The obtained solution was filtered, and diluted with conc. aqueous ammonium hydroxide (30 mL). The solution was kept for 24 h at 55° C. and evaporated to give crude 5'-DMT-protected oligonucleotide derivatized with cystamine (9600 OD, 436 mg). ESMS 7023.2 (calculated), 7023.5 (found).

The crude oligonucleotide was purified by HPLC on a Bondapak C18 column (20×100 mm 300 Å, 15 m). The column was eluted using 0.1 M $NH_4OAc$ as buffer A, 80% aqueous MeCN as buffer B, and linear gradient from 0 to 55% of B in 50 min at a flow rate 15 mL $min^{-1}$. The collected solution of purified oligonucleotide (3426 OD) was diluted with water to 0.5 L, acidified with 80% aqueous AcOH to pH 3.9 and left overnight. The solution was then neutralized by adding 10% aqueous ammonium hydroxide to pH 7.5 and evaporated to 100 mL. The resulting solution was purified by HPLC as described above eluting with a gradient from 0 to 35% B in 50 min. The collected fractions were evaporated to 50 mL.

The solution obtained was treated with dithiothreitol (0.1 M, 770 mg) overnight, and the reaction mixture was purified by HPLC as described above eluting with a gradient from 0 to 30% B in 60 min. The eluate of the product was collected to a solution of 2,2'-dipyridyldisulfide (20 mg) in MeCN (20 mL) and was kept overnight. The reaction mixture was then evaporated, dissolved in water (250 mL), and extracted with ethyl acetate (3×70 mL). The aqueous phase was evaporated to one half and purified by HPLC as described above eluting with a gradient from 0 to 44% B in 50 min. The collected fractions contained the desired pyridyldithio-activated oligonucleotide (2800 OD, 127 mg).

Example 40
Conjugate of $(TG)_2ctat_2c(tg)_2A_2T_2$ and Antennapaedia peptide (AcC(SH)-GABA-$G_2$RQIKIWFQN$R_2$MKW$K_2$-amide) (SEQ ID NO: 7) via 3'-O-[3-[N-[2-[(2-pyridyl)dithio ethyl] carbamoyl] propyl] thiophosphate group

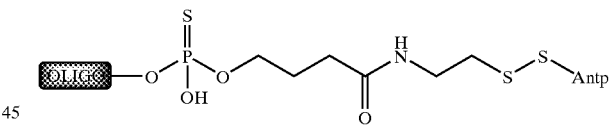

A mixture of pyridyldithio-activated oligonucleotide (1000 OD) dissolved in HPLC elution buffer (100 mL), KCl (0.79 g), urea (31.8 g), and MeCN (10 mL) was degassed, and aqueous Antennapaedia-SH peptide (47.5 mg) was added in portions under stirring. The reaction mixture was stirred overnight to yield 80% of conjugate according to ion exchange HPLC on a Poros DNA Q column (4.6×50 mm) using: 0.1 M $NH_4OAc$, 2 M urea, 30% MeCN as buffer A, A+1.5 M NaBr as buffer B, and a linear gradient from 0 to 40% of buffer B in 40 min at a flow rate of 3 mL $min^{-1}$.

The reaction mixture was diluted with water to 200 mL, and the conjugate was purified by anion-exchange chromatography on a MonoQ column (Pharmacia, 10×100 mm) using 0.1 M $NH_4OAc$, 2 M urea, 30% MeCN as buffer A, A+1.5 M NaBr as buffer B, and a linear gradient from 0 to 35% B in 45 min at a flow rate of 5 mL $min^{-1}$. The collected fractions were diluted with 6 volumes of water and desalted on a DeltaPak C4 column (7.8×300 mm). The product was evaporated to give the desired conjugate (606 OD, 35 mg). ESMS: 9231.5 (calculated), 9230.2 (found).

Example 41
Oligonucleotide (TG)$_2$ctat$_2$c(tg)$_2$A$_2$T$_2$ (SEQ ID NO: 20) activated with 3'-O-[3-[N-[2-[(2-pyridyl)dithio] ethyl] carbamoyl] propyl] thiophosphate group

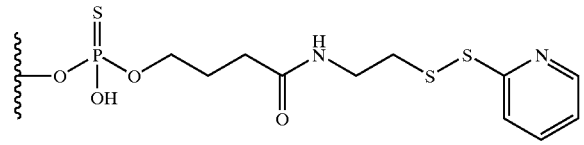

A solid support-bound oligonucleotide (TG)$_2$ctat$_2$c(tg)$_2$ A$_2$T$_2$ assembled on 2-[4-[(4,4'-dimethoxytrityl)oxy] butyrylthio]-acetyl derivatized CPG (60 mmol) was shaken with 1.0 M aqueous cystamine (15 mL) for 3 h at room temperature. The obtained solution was filtered, and diluted with conc. aqueous ammonium hydroxide (30 mL). The solution was kept for 24 h at 55° C. and evaporated to give crude 5'-DMT-protected oligonucleotide derivatized with cystamine (9600 OD, 436 mg). ESMS 7023.2 (calculated), 7023.5 (found).

The crude oligonucleotide was purified by HPLC on a Bondapak C18 column (20×100 mm 300 Å, 15 m). The column was eluted using 0.1 M NH$_4$OAc as buffer A, 80% aqueous MeCN as buffer B, and linear gradient from 0 to 55% of B in 50 min at a flow rate 15 mL min$^{-1}$. The collected solution of purified oligonucleotide (3426 OD) was diluted with water to 0.5 L, acidified with 80% aqueous AcOH to pH 3.9 and left overnight. The solution was then neutralized by adding 10% aqueous ammonium hydroxide to pH 7.5 and evaporated to 100 mL. The resulting solution was purified by HPLC as described above eluting with a gradient from 0 to 35% B in 50 min. The collected fractions were evaporated to 50 mL.

The solution obtained was treated with dithiothreitol (0.1 M, 770 mg) overnight, and the reaction mixture was purified by HPLC as described above eluting with a gradient from 0 to 30% B in 60 min. The eluate of the product was collected to a solution of 2,2'-dipyridyldisulfide (20 mg) in MeCN (20 mL) and was kept overnight. The reaction mixture was then evaporated, dissolved in water (250 mL), and extracted with ethyl acetate (3×70 mL). The aqueous phase was evaporated to one half and purified by HPLC as described above eluting with a gradient from 0 to 44% B in 50 min. The collected fractions contained the desired pyridyldithio-activated oligonucleotide (2800 OD, 127 mg).

Example 42
Conjugate of (TG)$_2$ctat$_2$c(tg)$_2$A$_2$T$_2$ (SEQ ID NO: 20) and TAT peptide (GRK$_2$R$_2$GR$_3$GYC(SH) amide) (SEQ ID NO: 22) via 3'-O-[3-[N-[2-[(2-pyridyl)dithio] ethyl] carbamoyl] propyl] thiophosphate group

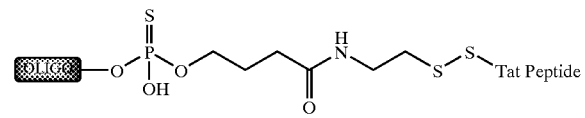

A mixture of pyridyldithio-activated oligonucleotide (1500 OD) dissolved in HPLC elution buffer (100 mL), KCl (0.79 g), urea (12 g), and MeCN (10 mL) was degassed, and aqueous Tat-SH peptide (29 mg) was added in portions under stirring. The reaction mixture was stirred overnight to yield 80% of conjugate according to ion exchange HPLC on a Poros DNA Q column (4.6×50 mm) using: 0.1 M NH$_4$OAc, 2 M urea, 30% MeCN as buffer A, A+1.5 M NaBr as buffer B, and a linear gradient from 0 to 40% of buffer B in 40 min at a flow rate of 3 mL min$^{-1}$.

The reaction mixture was diluted with water to 200 mL, and the conjugate was purified by anion-exchange chromatography on a MonoQ column (Pharmacia, 10×100 mm) using 0.1 M NH$_4$OAc, 2 M urea, 30% MeCN as buffer A, A+1.5 M NaBr as buffer B, and a linear gradient from 0 to 35% B in 45 min at a flow rate of 5 mL min$^{-1}$. The collected fractions were diluted with 6 volumes of water and desalted on a DeltaPak C4 column (7.8×300 mm). The product was evaporated to give the desired conjugate (1030 OD, 35 mg). ESMS: 8363.7 (calculated), 8361.5 (found).

Example 43
Oligonucleotide TGT$_2$AT$_2$CT$_3$AGA$_2$TG$_2$ (SEQ ID NO: 24) activated with 3'-O-[3-[N-[2-[(2-pyridyl)dithio] ethyl] carbamoyl] propyl] thiophosphate group A solid support-bound oligonucleotide TGT$_2$AT$_2$CT$_3$AGA$_2$TG$_2$ assembled on 2-[4-[(4,4'-dimethoxytrityl)oxy]butyrylthio]-acetyl derivatized CPG (75 mmol) was shaken with 1.0 M aqueous cystamine (15 mL) for 3 h at room temperature. The obtained solution was filtered, and diluted with conc. aqueous ammonium hydroxide (30 mL). The solution was kept for 24 h at 55° C. and evaporated to give crude 5'-DMT-protected oligonucleotide derivatized with cystamine. ESMS 7774.0 (calculated), 7773.5 (found).

The crude oligonucleotide was purified by HPLC on a Bondapak C18 column (20×100 mm 300 Å, 15 m). The column was eluted using 0.1 M NH$_4$OAc as buffer A, 80% aqueous MeCN as buffer B, and linear gradient from 20 to 80% of B in 60 min at a flow rate 15 mL min$^{-1}$. The collected solution of purified oligonucleotide (3726 OD) was diluted with water to 0.5 L, acidified with 80% aqueous AcOH to pH 3.9 and left overnight. The solution was then neutralized by adding 10% aqueous ammonium hydroxide to pH 7.5 and evaporated to 100 mL. The resulting solution was desalted by HPLC. The collected fractions were evaporated to 70 mL to give the detritylated oligonucleotide (3600 OD, 159.3 mg). ESMS 7471.6 (calculated), 7471.0 (found).

The solution obtained was treated with dithiothreitol (0.1 M, 1078 mg) overnight, and the reaction mixture was purified by HPLC as described above eluting with a gradient from 0 to 40% B in 40 min. The eluate of the product was collected to a solution of 2,2'-dipyridyldisulfide (80 mg) in MeCN (20 mL) and was kept overnight. The reaction mixture was then evaporated, dissolved in water (250 mL), and extracted with ethyl acetate (3×70 mL). The aqueous phase was evaporated to one half and purified by HPLC as described above eluting with a gradient from 0 to 40% B in 40 min. The collected fractions contained the desired pyridyldithio-activated oligonucleotide (2980 OD, 132 mg).

Example 44
Conjugate of TGT$_2$AT$_2$CT$_3$AGA$_2$TG$_2$ (SEQ ID NO: 24) and Antennapaedia peptide (AcC(SH)-GABA-G$_2$RQIKIWFQNR$_2$MKWK$_2$-amide) (SEQ ID NO: 7) via 3'-O-[3-[N-[2-[(2-pyridyl)dithio] ethyl] carbamoyl] propyl] thiophosphate group

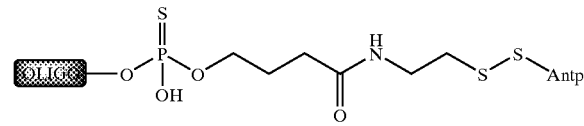

A mixture of pyridyldithio-activated oligonucleotide (100 OD) dissolved in HPLC elution buffer (7 mL), KCl (74 mg), urea (1200 mg), and MeCN (4 mL) was degassed, aqueous Antennapaedia-SH peptide (3 mg) was added in portions under stirring, and the reaction mixture was left overnight.

The reaction mixture was diluted with water to 20 mL, and the conjugate was purified by anion-exchange chromatography on a Source 30Q column (Pharmacia, 10×100 mm) using 0.1 M NH$_4$OAc, 2 M urea, 30% MeCN as buffer A, A+1.5 M NaBr as buffer B, and a linear gradient from 1 to 40% B in 40 min at a flow rate of 3 mL min$^{-1}$. The collected fractions were diluted with 6 volumes of water and desalted on a DeltaPak C4 column (7.8×300 mm). The product was evaporated to give the desired conjugate (68 OD, 2.6 mg).

Example 45

Oligonucleotide (TG)$_2$ctat$_2$c(tg)$_2$A2T$_2$ (SEQ ID NO: 20) activated with 3'-O-[3-[N-[3-[(2-pyridyl)dithio] propyl] carbamoyl] propyl] thiophosphate group

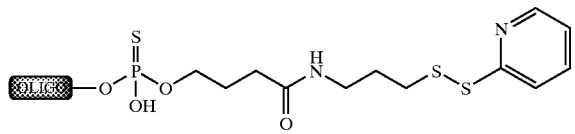

A solid support-bound oligonucleotide TGT$_2$AT$_2$CT$_3$AGA$_2$TG$_2$ assembled on 2-[4-[(4,4'-dimethoxytrityl)oxy]butyrylthio]-acetyl derivatized CPG (4 mmol) is shaken with 1.0 M aqueous 3,3'-dithiobispropylamine synthesized as described in (Evans, B. J.; Doi, J. T.; Musker, W. K. Kinetics of the aqueous periodate oxidation of aliphatic disulfides and thioethers. J. Org. Chem. (1990), 55(9), 2580–2586) (1 mL) for 3 h at room temperature. The obtained solution is filtered, and diluted with conc. aqueous ammonium hydroxide (5 mL). The solution is kept for 24 h at 55° C. and evaporated to give crude 5'-DMT-protected oligonucleotide derivatized with 3,3'-dithiobispropylamine.

The crude oligonucleotide is purified by HPLC on a DeltaPak C18 column (7.8×300 mm 300 Å, 15 m). The column was eluted using 0.1 M NH$_4$OAc as buffer A, 80% aqueous MeCN as buffer B, and linear gradient from 20 to 80% of B in 60 min at a flow rate 5 mL min$^{-1}$. The collected solution of purified oligonucleotide is diluted with water to 50 mL, acidified with 80% aqueous AcOH to pH 3.9 and left overnight. The solution is then neutralized by adding 10% aqueous ammonium hydroxide to pH 7.5 and evaporated to 10 mL. The resulting solution is desalted by HPLC. The collected fractions are evaporated to 10 mL to give the detritylated oligonucleotide.

The solution obtained is treated with dithiothreitol (0.1 M, 30 mg) overnight, and the reaction mixture is purified by HPLC as described above eluting with a gradient from 0 to 40% B in 40 min. The eluate of the product was collected to a solution of 2,2'-dipyridyldisulfide (10 mg) in MeCN (1 mL) and is kept overnight. The reaction mixture is then evaporated, dissolved in water (50 mL), and extracted with ethyl acetate (3×20 mL). The aqueous phase is evaporated to one half and purified by HPLC as described above eluting with a gradient from 0 to 40% B in 40 min to give the desired pyridyldithio-activated oligonucleotide.

Example 46

Conjugate of (TG)$_2$ctat$_2$c(tg)$_2$A2T$_2$ (SEQ ID NO: 20) and Antennapaedia peptide (AcC(SH)GABA-G$_2$RQIKIWFQNR$_2$MKWK$_2$-amide) (SEQ ID NO: 7) via 3'-O-[3-[N-[3-[(2-pyridyl)dithio] propyl] carbamoyl]) propyl] thiophosphate group

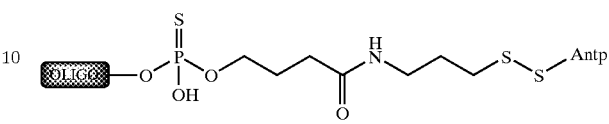

A mixture of pyridyldithio-activated oligonucleotide (100 OD) dissolved in HPLC elution buffer (7 mL), KCl (74 mg), urea (1200 mg), and MeCN (4 mL) is degassed, aqueous Antennapaedia-SH peptide (3 mg) is added in portions under stirring, and the reaction mixture is left overnight. The reaction mixture is diluted with water to 20 mL, and the conjugate was purified by anion-exchange chromatography on a Source 30Q column (Pharmacia, 10×100 mm) using 0.1 M NH$_4$OAc, 2 M urea, 30% MeCN as buffer A, A+1.5 M NaBr as buffer B, and a linear gradient from 1 to 40% B in 40 min at a flow rate of 3 mL min$^{-1}$. The collected fractions are diluted with 6 volumes of water and desalted on a DeltaPak C4 column (7.8×300 mm) to give, on evaporation, the desired conjugate.

Example 47

Oligonucleotide (TG)$_2$ctat$_2$c(tg)$_1$A$_2$T$_2$ (SEQ ID NO: 20) activated with 3'-O-[3-[N-[2- [(2-pyridyl)dithio] ethyl] carbamoyl] propyl] thiophosphate group A solid support-bound oligonucleotide TGT$_2$AT$_2$CT$_3$AGA$_2$TG$_2$ assembled on 4-[4-[(4,4'-dimethoxytrityl)oxy]butyrylthio]-benzoyl derivatized CPG (4 mmol) is shaken with 1.0 M aqueous cystamine (1 mL) for 3 h at room temperature. The obtained solution is filtered and diluted with conc. aqueous ammonium hydroxide (5 mL). The solution is kept for 24 h at 55° C. and evaporated to give crude 5'-DMT-protected oligonucleotide derivatized with cystamine.

The crude oligonucleotide is purified by HPLC on a DeltaPak C18 column (7.8×300 mm 300 Å, 15 m). The column was eluted using 0.1 M NH$_4$OAc as buffer A, 80% aqueous MeCN as buffer B, and linear gradient from 20 to 80% of B in 60 min at a flow rate 5 mL min$^{-1}$. The collected solution of purified oligonucleotide is diluted with water to 50 mL, acidified with 80% aqueous AcOH to pH 3.9 and left overnight. The solution is then neutralized by adding 10% aqueous ammonium hydroxide to pH 7.5 and evaporated to 10 mL. The resulting solution is desalted by HPLC. The collected fractions are evaporated to 10 mL to give the detritylated oligonucleotide.

The solution obtained is treated with dithiothreitol (0.1 M, 30 mg) overnight, and the reaction mixture is purified by HPLC as described above eluting with a gradient from 0 to 40% B in 40 min. The eluate of the product was collected to a solution of 2,2'-dipyridyldisulfide (10 mg) in MeCN (1 mL) and is kept overnight. The reaction mixture is then evaporated, dissolved in water (50 mL), and extracted with ethyl acetate (3×20 mL). The aqueous phase is evaporated to one half and purified by HPLC as described above eluting with a gradient from 0 to 40% B in 40 min to give the desired pyridyldithio-activated oligonucleotide.

Example 48

Oligonucleotide $CIG)_2ctat_2c(tg)_2A_2T_2$ (SEQ ID NO: 20) activated with 3'-O-[[4-[N-[2-[(2-pyridyl)dithio] ethyl] carbamoyl] phenyl] methyl] thiophosphate group A solid support-bound oligonucleotide $TGT_2AT_2CT_3AGA_2TG_2$ assembled on 2-[4-[[(4,4'-dimethoxytrityl)oxy]methyl]-benzoylthio]acetyl derivatized CPG (4 mmol) is shaken with 1.0 M aqueous cystamine (1 mL) for 3 h at room temperature. The obtained solution is filtered and diluted with conc. aqueous ammonium hydroxide (5 mL). The solution is kept for 24 h at 55° C. and evaporated to give crude 5'-DMT-protected oligonucleotide derivatized with cystamine.

The crude oligonucleotide is purified by HPLC on a DeltaPak C18 column (7.8×300 mm 300 Å, 15 m). The column was eluted using 0.1 M $NH_4OAc$ as buffer A, 80% aqueous MeCN as buffer B, and linear gradient from 20 to 80% of B in 60 min at a flow rate 5 mL min$^{-1}$. The collected solution of purified oligonucleotide is diluted with water to 50 mL, acidified with 80% aqueous AcOH to pH 3.9 and left overnight. The solution is then neutralized by adding 10% aqueous ammonium hydroxide to pH 7.5 and evaporated to 10 mL. The resulting solution is desalted by HPLC. The collected fractions are evaporated to 10 mL to give the detritylated oligonucleotide.

The solution obtained is treated with dithiothreitol (0.1 M, 30 mg) overnight, and the reaction mixture is purified by HPLC as described above eluting with a gradient from 0 to 40% B in 40 min. The eluate of the product was collected to a solution of 2,2'-dipyridyldisulfide (10 mg) in

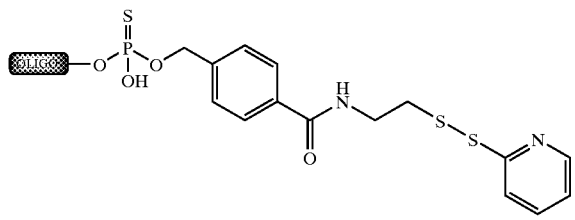

MeCN (1 mL) and is kept overnight. The reaction mixture is then evaporated, dissolved in water (50 mL), and extracted with ethyl acetate (3×20 mL). The aqueous phase is evaporated to one half and purified by HPLC as described

above eluting with a gradient from 0 to 40% B in 40 min to give the desired pyridyldithio-activated oligonucleotide.

Example 49

Oligonucleotide $(TG)_2ctat_2c(tg)_2A_2T_2$ (SEQ ID NO: 20) activated with 3'-O-[[4-[N-[2-[(2-pyridyl)dithio] ethyl] carbamoyl phenyl] methyl] thiophosphate group A solid support-bound oligonucleotide $TGT_2AT_2CT_3AGA_2TG_2$ assembled on 4-[4-[[(4,4'-dimethoxytrityl)oxy]methyl]-benzoylthio]benzoyl derivatized CPG (4 mmol) is shaken with 1.0 M aqueous cystamine (1 mL) for 3 h at room temperature. The obtained solution is filtered and diluted with conc. aqueous ammonium hydroxide (5 mL). The solution is kept for 24 h at 55° C. and evaporated to give crude 5'-DMT-protected oligonucleotide derivatized with cystamine.

The crude oligonucleotide is purified by HPLC on a DeltaPak C18 column (7.8×300 mm 300 Å, 15 m). The column was eluted using 0.1 M $NH_4OAc$ as buffer A, 80% aqueous MeCN as buffer B, and linear gradient from 20 to 80% of B in 60 min at a flow rate 5 mL min$^{-1}$. The collected solution of purified oligonucleotide is diluted with water to 50 mL, acidified with 80% aqueous ACOH to pH 3.9 and left overnight. The solution is then neutralized by adding 10% aqueous ammonium hydroxide to pH 7.5 and evaporated to 10 mL. The resulting solution is desalted by HPLC. The collected fractions are evaporated to 10 mL to give the detritylated oligonucleotide.

The solution obtained is treated with dithiothreitol (0.1 M, 30 mg) overnight, and the reaction mixture is purified by HPLC as described above eluting with a gradient from 0 to 40% B in 40 min. The eluate of the product was collected to a solution of 2,2'-dipyridyldisulfide (10 mg) in MeCN (1 mL) and is kept overnight. The reaction mixture is then evaporated, dissolved in water (50 mL), and extracted with ethyl acetate (3×20 mL). The aqueous phase is evaporated to one half and purified by HPLC as described above eluting with a gradient from 0 to 40% B in 40 min to give the desired pyridyldithio-activated oligonucleotide.

Example 50

Conjugate of $TGT_2AT_2CT_3AGA_2TG_2$ (SEQ ID NO: 21) and Antennapaedia peptide (AcC(SH)GABA-$G_2RQIKIWFQNR_2MKWK_2$-amide) (SEQ ID NO: 7) via 3'-O-[[4-[N-2-[(2-pyridyl)dithio] ethyl] carbamoyl] phenyl] methyl] thiophosphate group

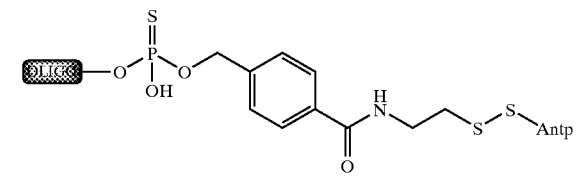

A mixture of pyridyldithio-activated oligonucleotide (100 OD) dissolved in HPLC elution buffer (7 mL), KCl (74 mg), urea (1200 mg), and MeCN (4 mL) is degassed, aqueous Antennapaedia-SH peptide (3 mg) is added in portions under stirring, and the reaction mixture is left overnight.

The reaction mixture is diluted with water to 20 mL, and the conjugate was purified by anion-exchange chromatography on a Source 30Q column (Pharmacia, 10×100 mm) using 0.1 M $NH_4OAc$, 2 M urea, 30% MeCN as buffer A, A+1.5 M NaBr as buffer B, and a linear gradient from 1 to 40% B in 40 min at a flow rate of 3 mL min$^{-1}$. The collected fractions are diluted with 6 volumes of water and desalted on a DeltaPak C4 column (7.8×300 mm) to give, on evaporation, the desired conjugate.

Example 51

Oligonucleotide $(TG)_2ctat_2c(tg)_2A_2T_2$ (SEQ ID NO: 20) activated with 3'-O-[2-[1-[N-2-[(2-pyridyl)dithio] ethyl] carbamoyl] methoxy]ethyl] thiophosphate group

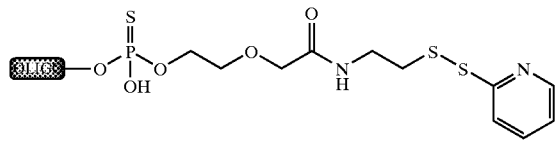

A solid support-bound oligonucleotide $TGT_2AT_2CT_3AGA_2TG_2$ assembled on 2-[2-[2-(4,4'-dimethoxytrityloxy)ethoxy]acetyl-thio]acetyl-derivatized CPG (4 mmol) is shaken with 1.0 M aqueous cystamine (1 mL) for 3 h at room temperature. The obtained solution is filtered and diluted with conc. aqueous ammonium hydroxide (5 mL). The solution is kept for 24 h at 55° C. and evaporated to give crude 5'-DMT-protected oligonucleotide derivatized with cystamine.

The crude oligonucleotide is purified by HPLC on a DeltaPak C18 column (7.8×300 mm 300 Å, 15 m). The column is eluted using 0.1 M $NH_4OAc$ as buffer A, 80% aqueous MeCN as buffer B, and linear gradient from 20 to 80% of B in 60 min at a flow rate 5 mL min$^{-1}$. The collected solution of purified oligonucleotide is diluted with water to 50 mL, acidified with 80% aqueous AcOH to pH 3.9 and left overnight. The solution is then neutralized by adding 10% aqueous ammonium hydroxide to pH 7.5 and evaporated to 10 mL. The resulting solution is desalted by HPLC. The collected fractions are evaporated to 10 mL to give the detritylated oligonucleotide.

The solution obtained is treated with dithiothreitol (0.1 M, 30 mg) overnight, and the reaction mixture is purified by HPLC as described above eluting with a gradient from 0 to 40% B in 40 min. The eluate of the product was collected to a solution of 2,2'-dipyridyldisulfide (10 mg) in MeCN (1 mL) and is kept overnight. The reaction mixture is then evaporated, dissolved in water (50 mL), and extracted with ethyl acetate (3×20 mL). The aqueous phase is evaporated to one half and purified by HPLC as described above eluting with a gradient from 0 to 40% B in 40 min to give the desired pyridyldithio-activated oligonucleotide.

Example 52

Conjugate of $(TG)2ctat_2c(tg)_1A_2T_2$ (SEQ ID NO: 20) and Antennapaedia peptide $(AcC(SH)-GABA-G_2RQIKIWFQNR_2MKWK_2$-amide) (SEQ ID NO: 7) via 3'-Q-[2-[1-[N-[2-[(2-pyridyl)dithio] ethyl] carbamoyl] methoxy] ethyl] thiophosphate group

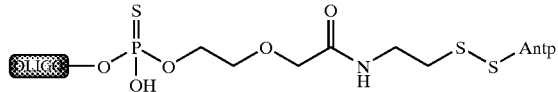

A mixture of pyridyldithio-activated oligonucleotide (100 OD) dissolved in HPLC elution buffer (7 mL), KCl (74 mg), urea (1200 mg), and MeCN (4 mL) is degassed, aqueous Antennapaedia-SH peptide (3 mg) is added in portions under stirring, and the reaction mixture is left overnight. The reaction mixture is diluted with water to 20 mL, and the conjugate is purified by anion-exchange chromatography on a Source 30Q column (Pharmacia, 10×100 mm) using 0.1 M $NH_4OAc$, 2 M urea, 30% MeCN as buffer A, A+1.5 M NaBr as buffer B, and a linear gradient from 1 to 40% B in 40 min at a flow rate of 3 mL min$^{-1}$. The collected fractions are diluted with 6 volumes of water and desalted on a DeltaPak C4 column (7.8×300 mm) to give, on evaporation, the desired conjugate.

Example 53

Conjugates synthesized using commercial solid support (Glen Research) Conjugate of $AGCT_2Ct_3g(ca)_2TGTA_3$ 16518 (SEQ ID NO: 21) and Tat peptide $(GRK_2R_2GR_3CYC(SH)$ amide) (SEQ ID NO:22) via 3'-Q-[3-[(2-pyridyl)dithio] propyl] thiophosphate group.

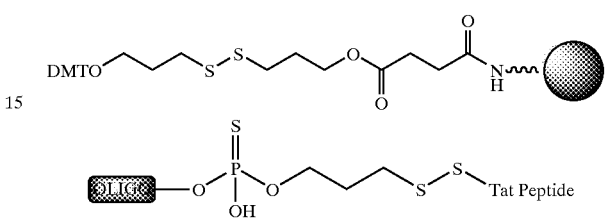

A mixture of pyridyldithio-activated oligonucleotide (600 OD) dissolved in HPLC elution buffer (6 mL), KCl (1 M, 7.5 mL), urea (4.5 g), MeCN (22.5 mL), and a buffer (0.1 M $NH_4OAc$ and 2 M urea in 30% aqueous MeCN; 37.5 mL) was degassed, and aqueous Tat-SH peptide (7 mg) was added in portions under stirring. The reaction mixture was stirred overnight to yield 80% of conjugate according to ion exchange HPLC on a Poros DNA Q column (4.6×50 mm) using: 0.1 M $NH_4OAc$, 2 M urea, 30% MeCN as buffer A, A+1.5 M NaBr as buffer B, and a linear gradient from 0 to 40% of buffer B in 40 min at a flow rate of 3 mL min$^{-1}$.

The reaction mixture was diluted with water to 100 mL, and the conjugate was purified by anion-exchange chromatography on a MonoQ column (Pharmacia, 10×100 mm) using 0.1 M $NH_4OAc$, 2 M urea, 30% MeCN as buffer A, A+1.5 M NaBr as buffer B, and a linear gradient from 0 to 50% B in 40 min at a flow rate of 5 mL min$^{-1}$. The collected fractions were diluted with 6 volumes of water and first desalted on a DeltaPak C4 column (7.8×300 mm) and then on a Sephadex G25 column. The product was evaporated to give the desired conjugate (380 OD). ESMS: 9201.5 (calculated), 9199.5 (found).

Example 54

Conjugate of $TC_2gtcatcgctC_2TCAG_3$(SEQ ID NO: 1) 13920-Tat peptide $(GRK_2R_2GR_3GYC(SH)$ amide) (SEQ ID NO: 22) via 3'-O-[3-[(2-pyridyl)dlthio] propyl] thiophosphate group

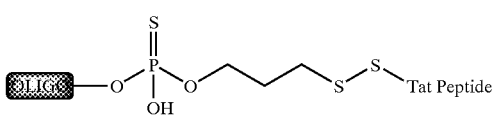

A mixture of pyridyldithio-activated oligonucleotide (368 OD) dissolved in HPLC elution buffer (10.7 mL), KCl (1 M, 4.6 mL), urea (2.8 g), MeCN (6.9 mL), and a buffer (0.1 M $NH_4OAc$ and 2 M urea in 30% aqueous MeCN; 23 mL) was degassed, and aqueous Tat-SH peptide (5.3 mg) was added in portions under stirring. The reaction mixture was stirred overnight to yield 80% of conjugate according to ion exchange HPLC on a Poros DNA Q column (4.6×50 mm) using: 0.1 M $NH_4OAc$, 2 M urea, 30% MeCN as buffer A, A+1.5 M NaBr as buffer B, and a linear gradient from 0 to 40% of buffer B in 40 min at a flow rate of 3 mL min$^{-1}$.

The reaction mixture was diluted with water to 100 mL, and the conjugate was purified by anion-exchange chromatography on a MonoQ column (Pharmacia, 10×100 mm) using 0.1 M NH$_4$OAc, 2 M urea, 30% MeCN as buffer A, A+1.5M NaBr as buffer B, and a linear gradient from 0 to 50% B in 45 min at a flow rate of 5 mL min$^{-1}$. The collected fractions were diluted with 6 volumes of water and first desalted on a DeltaPak C4 column (7.8×300 mm) and then on a Sephadex G25 column. The product was evaporated to give the desired conjugate (150 OD). ESMS: 9123.5 (calculated), 9121.3 (found).

Example 55

Conjugate of CTACGct$_3$c$_2$acgcACAGT (SEQ ID NO: 3)16009 and Tat peptide (GRK$_2$R$_2$GR$_3$GYC(SH) amide) (SEQ ID NO: 22) via 3'-O-[3-[(2-pyridyl)ditbio] propyl] thiophosphate group

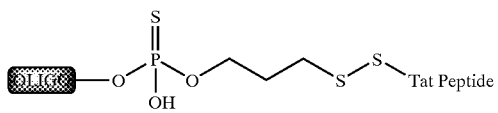

A mixture of pyridyldithio-activated oligonucleotide (162 OD) dissolved in HPLC elution buffer (4.6 mL), KCl (1 N, 2 mL), urea (1.2 g), MeCN (3 mL), and a buffer (0.1 N NH$_4$OAc and 2 N urea in 30% aqueous MeCN; 10.0 mL) was degassed, and aqueous Tat-SH peptide (2.8 mg) was added in portions under stirring. The reaction mixture was stirred overnight to yield 80% of conjugate according to ion exchange HPLC on a Poros DNA Q column (4.6×50 mm) using: 0.1 M NH$_4$OAc, 2 M urea, 30% MeCN as buffer A, A+1.5 M NaBr as buffer B, and a linear gradient from 0 to 40% of buffer B in 40 min at a flow rate of 3 mL min$^{-1}$.

The reaction mixture was diluted with water to 50 mL, and the conjugate was purified by anion-exchange chromatography on a MonoQ column (Pharmacia, 10×100 mm) using 0.1 M NH$_4$OAc, 2 M urea, 30% MeCN as buffer A, A+1.5 M NaBr as buffer B, and a linear gradient from 0 to 50% B in 50 min at a flow rate of 5 mL min$^{-1}$. The collected fractions were diluted with 6 volumes of water and first desalted on a DeltaPak C4 column (7.8×300 mm) and then on a Sephadex G25 column. The product was evaporated to give the desired conjugate (150 OD). ESMS: 8989.4 (calculated), 8988.7 (found).

What is claimed is:

1. A method for preparing a peptide linked oligomeric compound comprising the steps of:

(a) providing a support medium derivatized with a compound wherein said compound comprises a protected hydroxyl group;

(b) treating said protected hydroxyl group with a deprotecting reagent effective to deprotect said hydroxyl group;

(c) reacting said deprotected hydroxyl group with a 2'-, 3'-, or 5'-H-phosphonate nucleoside having a protected hydroxyl group and an activated phosphorus containing substituent group thereby forming an extended compound;

(d) optionally treating said extended compound with a capping agent to form a capped compound;

(e) optionally repeating steps (b), (c) and (d) to form a further extended compound;

(f) treating said capped compound or said further extended compound with an oxidizing reagent thereby forming an oxidized compound comprising one or more nucleosides;

(g) repeating steps (b), (c), (d), (e) and (f) for oxidized compounds comprising one nucleoside or optionally repeating steps (b), (c), (d), (e) and (f) for oxidized compounds comprising more than one nucleoside to give a further oxidized compound;

(h) cleaving said oxidized compound or said further oxidized compound from the support medium to give said oligomeric compound comprising a linking moiety;

(i) treating said linking moiety attached to said oligomeric compound with reagents effective to form a reactive sulfur moiety on said linking moiety; and (j) reacting said reactive sulfur moiety with a peptide wherein said peptide is functionalized with a functional group reactive with said sulfur moiety thereby forming said peptide linked oligomeric compound.

2.K The method of claim 1 wherein one of said reactive sulfur moiety and said functional group is —SH and the other of said reactive sulfur moiety and said functional group is a disulfide group.

3. The method of claim 1 wherein said support medium derivatized with a compound comprising a protected hydroxyl group is 3'-thiol-modifier C3 S—S CPG (DMT-O—(CH$_2$)$_3$—S—S—(CH$_2$)$_3$—O-succinyl-LCAA-CPG).

4. The method of claim 1 wherein each hydroxyl protecting group is, independently, trityl, monomethoxytrityl, dimethoxytrityl, trimethoxytrityl, 9-phenylxanthin-9-yl (Pixyl) or 9-(p-methoxyphenyl)xanthin-9-yl (MOX).

5. The method of claim 1 wherein said hydroxyl protecting groups are acid labile.

6. The method of claim 5 wherein said deprotecting reagent is a weak acid.

7. The method of claim 6 wherein said deprotecting reagent is dichloroacetic acid or trichloroacetic acid.

8. The method of claim 1 wherein said cleaving is performed using aqueous ammonium hydroxide.

9. The method of claim 1 wherein said oligomeric compound comprises from about 5 to about 50 nucleosides.

10. The method of claim 1 wherein said oligomeric compound comprises from about 8 to about 30 nucleosides.

11. The method of claim 1 wherein said oligomeric compound comprises from about 15 to about 25 nucleosides.

12. The method of claim 1 wherein said peptide linked oligomeric compound has one of the formulas:

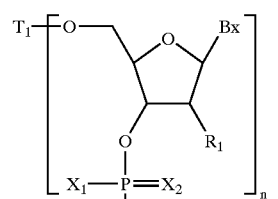

or

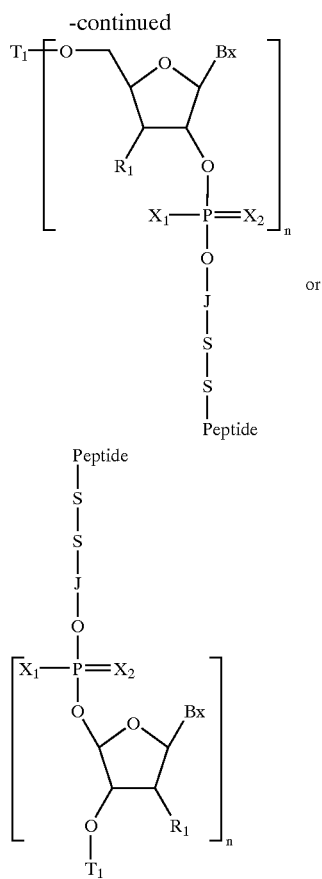

wherein

T₁ is hydrogen or a hydroxyl protecting group;

J is $C_1$–$C_{12}$ alkyl or -$Q_1$-G-$Q_2$;

$Q_1$ is $C_1$–$C_{12}$ alkyl, alkaryl or [(CH$_2$)$_{mm}$—O—(CH$_2$)$_{mm'}$];

each mm and mm' are, independently, from 1 to about 6;

p is from 1 to about 6;

$Q_2$ is $C_1$–$C_{12}$ alkyl;

$G_2$ is —NH—C(O)—, —NH—C(O)—NH—, —NH—C(S)—NH—, —NH—O—, or —NH—C(O)—O—;

each $X_2$ is, independently, O or S;

each $X_1$ is, independently, $R_5$—O—, Pg-S—, $C_1$–$C_{10}$ straight or branched chain alkyl, CH$_3$(CH$_2$)$_5$—O—, $R_2R_3$N— or a group remaining from coupling a chiral auxiliary;

g is from 0 to 10;

$R_5$ is CH$_3$, —GH$_2$CH$_2$CN, —C(CH$_3$)(CH$_3$)—CCl$_3$, —CH$_2$—CCl$_3$, —CH$_2$CH═GH$_2$, CH$_2$CH$_2$SiCH$_3$, 2-yl-ethyl phenylsulfonate, δ-cyanobutenyl, cyano p-xylyl, diphenylsilylethyl, 4-nitro-2-yl-ethylbenzene, 2-yl-ethyl-methyl sulfonate, methyl-N-trifluoroacetyl ethyl, acetoxy phenoxy ethyl, or a blocking group;

each $R_2$ and $R_3$ is, independently, hydrogen, $C_1$–$C_{10}$ alkyl, cycloalkyl or aryl;

or optionally, $R_2$ and $R_3$, together with the nitrogen atom to which they are attached form a cyclic moiety;

each Bx is, independently, a heterocyclic base moiety;

each $R_1$ is, independently, H, a blocked hydroxyl group, or a sugar substituent group; and n is from 2 to about 50.

13. The method of claim 1 wherein said reactive sulfur moiety is reacted with an equimolar amount of said functionalized peptide.

14. A method for preparing a peptide linked oligomeric compound having one of the formulas:

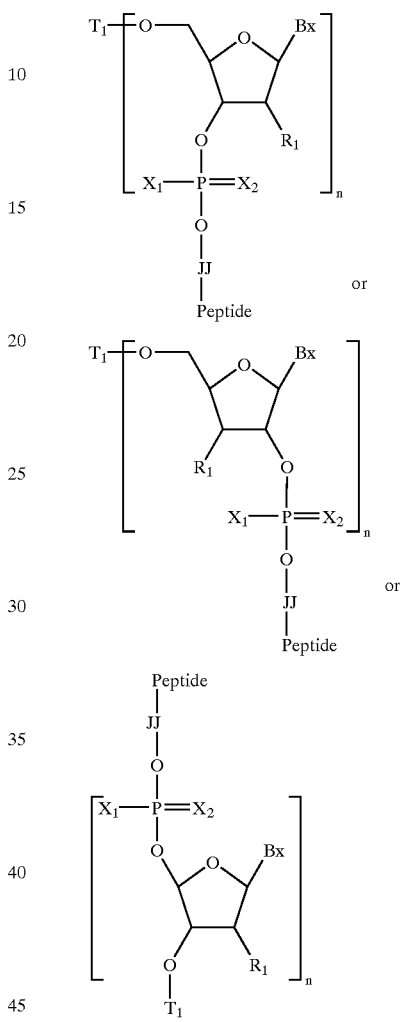

wherein $T_1$ is hydrogen or a hydroxyl protecting group;

each $X_2$ is, independently, O or S;

each $X_1$ is, independently, Pg-O—, Pg-S—, $C_1$–$C_{10}$ straight or branched chain alkyl, CH$_3$(CH$_2$)$_g$—O—, $R_2R_3$N— or a group remaining from coupling a chiral auxiliary;

g is from 0 to 10;

Pg is CH$_3$, —CH$_2$CH$_2$CN, —C(CH$_3$)(CH$_3$)—CCl3, —CH$_2$—CCl$_3$, —CH$_2$CH═CH$_2$, CH$_2$CH$_2$SiCH$_3$, 2-yl-ethyl phenylsulfonate, δ-cyanobutenyl, cyano p-xylyl, diphenylsilylethyl, 4-nitro-2-yl-ethylbenzene, 2-yl-ethyl-methyl sulfonate, methyl-N-trifluoroacetyl ethyl, acetoxy phenoxy ethyl, or a blocking group;

each $R_2$ and $R_3$ is, independently, hydrogen, $C_1$–$C_{10}$ alkyl, cycloalkyl or aryl;

or optionally, $R_2$ and $R_3$, together with the nitrogen atom to which they are attached form a cyclic moiety;

each Bx is, independently, a heterocyclic base moiety;

each $R_1$ is, independently, H, a blocked hydroxyl group, or a sugar substituent group;

n is from 2 to about 50; and

JJ has one of the formulas;

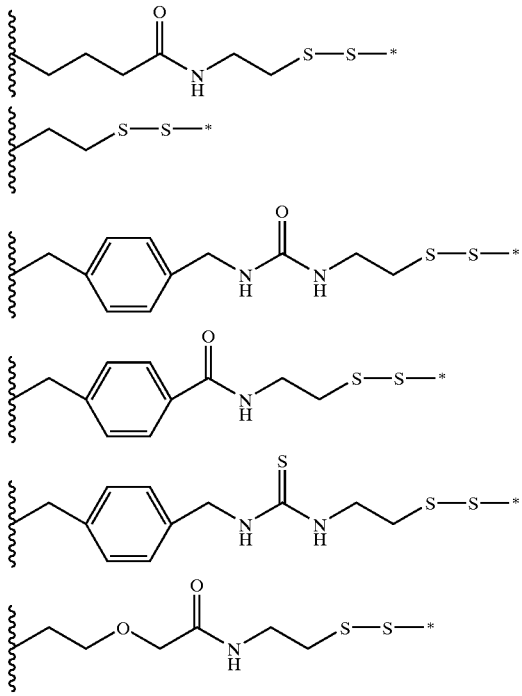

wherein * denotes the point of attachment to the peptide; comprising the steps of:

providing an oligomeric compound of the formula:

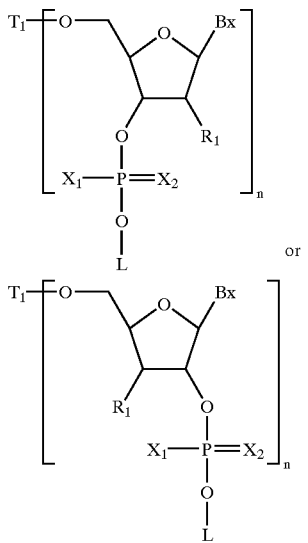

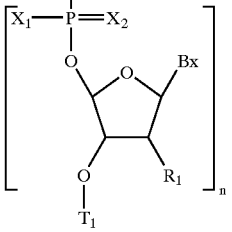

wherein L has one of the formulas:

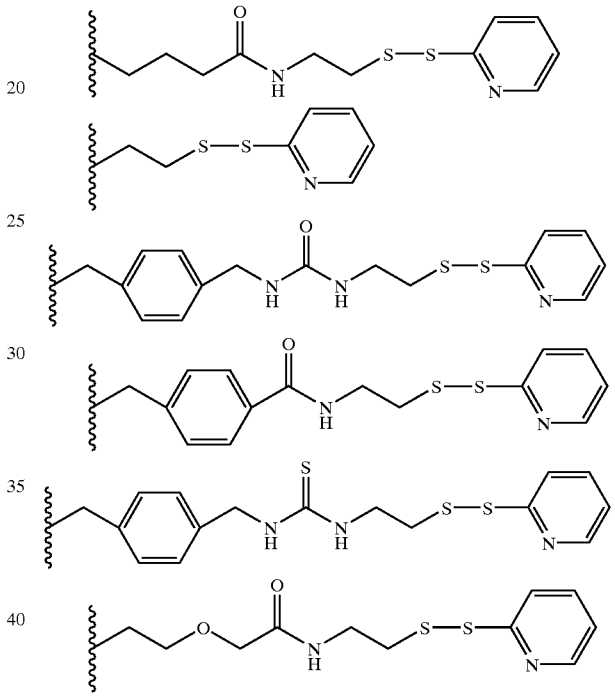

reacting said oligomeric compound with a functionalized peptide having a —SH functional group thereby forming said peptide linked oligomeric compound.

15. The method of claim 14 wherein said oligomeric compound is reacted with an equimolar amount of said functionalized peptide.

16. A peptide linked oligomeric compound having the formula:

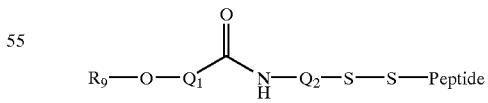

wherein:

$R_9$ is an oligomeric compound;

$Q_1$ is $C_1$–$C_{12}$ alkyl, —[$(CH_2)_{mm}$—O—$(CH_2)_{mm'}$], aryl or alkaryl;

p is from 1 to about 6;

each mm and mm' are, independently, from 1 to about 6; and $Q_2$ is $C_2$–$C_{12}$ alkyl.

17. The peptide linked oligomeric compound of claim 16, wherein $Q_1$ is propyl and is ethyl.

18. A method for preparing a peptide linked oligomeric compound comprising the steps of:
(a) providing a support medium derivatized with a compound having the formula:

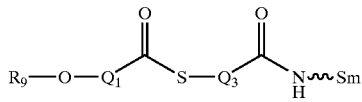

wherein R9 comprises a hydroxy] protecting group;
$Q_1$ is $C_1$–$C_{12}$ alkyl, alkaryl or —[$(CH_2)_{mm}$—I—$(CH_2)_{mm'}]_p$-;
$Q_3$ is $C_1$–$C_{12}$ alkyl, aryl or alkaryl;
Sm is a support medium;
p is from 1 to about 6; and
each mm and mm' are, independently, from 1 to about 6;
(b) treating said hydroxyl protecting group with a deprotecting reagent effective to deprotect said hydroxyl group;
(c) reacting said deprotected hydroxyl group with a nucleoside having a protected hydroxyl group and an activated phosphorus containing substituent group thereby forming an extended compound;
(d) optionally treating said extended compound with a capping agent to form a capped compound;
(e) optionally repeating steps (b), (c) and (d) to form a further extended compound;
(f) treating said capped compound or said further extended compound with an oxidizing reagent thereby forming an oxidized compound comprising one or more nucleosides;
(g) repeating steps (b), (c), (d), (e) and (f) for oxidized compounds comprising one nucleoside or optionally repeating steps (b), (c), (d), (e) and (f) for oxidized compounds comprising more than one nucleoside to give a further oxidized compound;
(h) cleaving said oxidized compound or said further oxidized compound from the support medium to give said oligomeric compound comprising a linking moiety;
(i) treating said linking moiety attached to said oligomeric compound with reagents effective to form a reactive sulfur moiety on said linking moiety; and
(j) reacting said reactive sulfur moiety with a peptide wherein said peptide is functionalized with a functional group reactive with said sulfur moiety thereby forming said peptide linked oligomeric compound.

19. The method of claim 18 wherein

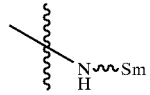

is a support medium having long chain alkyl amine groups.

20. The method of claim 18 wherein $Q_1$ is propyl and $Q_3$ is methyl.

21. A method for preparing a peptide linked oligomeric compound comprising the steps of:
(a) providing a support medium derivatized with a compound wherein said compound comprises a protected hydroxyl group;
(b) treating said protected hydroxyl group with a deprotecting reagent effective to deprotect said hydroxyl group;
(c) reacting said deprotected hydroxyl group with a nucleoside having a protected hydroxyl group and an activated phosphorus containing substituent group thereby forming an extended compound;
(d) treating said extended compound with a capping agent to form a capped compound, wherein said capping agent comprises 20% acetic anhydride in acetonitrile mixed with about an equal volume of a solution having 20% N-methylimidazole, 30% pyridine and 50% acetonitrile;
(e) optionally repeating steps (b), (c) and (d) to form a further extended compound;
(f) treating said capped compound or said further extended compound with an oxidizing reagent thereby forming an oxidized compound comprising one or more nucleosides;
(g) repeating steps (b), (c), (d), (e) and (f) for oxidized compounds comprising one nucleoside or optionally repeating steps (b), (c), (d), (e) and (f) for oxidized compounds comprising more than one nucleoside to give a further oxidized compound;
(h) cleaving said oxidized compound or said further oxidized compound from the support medium to give said oligomeric compound comprising a linking moiety;
(i) treating said linking moiety attached to said oligomeric compound with reagents effective to form a reactive sulfur moiety on said linking moiety; and
(j) reacting said reactive sulfur moiety with a peptide wherein said peptide is functionalized with a functional group reactive with said sulfur moiety thereby forming said peptide linked oligomeric compound.

22. A method for preparing a peptide linked oligomeric compound comprising the steps of:
(a) providing a support medium derivatized with a compound that comprises a protected hydroxyl group;
(b) treating said protected hydroxyl group with a deprotecting reagent effective to deprotect said hydroxyl group;
(c) reacting said deprotected hydroxyl group with a nucleoside having a protected hydroxyl group and an activated phosphorus containing substituent group, thereby forming an extended compound;
(d) optionally treating said extended compound with a capping agent to form a capped compound;
(e) optionally repeating steps (b), (c) and (d) to form a further extended compound;
(f) treating said capped compound or said further extended compound with an oxidizing reagent thereby forming an oxidized compound comprising one or more nucleosides;
(g) repeating steps (b), (c), (d), (e) and (f) for oxidized compounds comprising one nucleoside or optionally repeating steps (b), (c), (d), (e) and (f) for oxidized compounds comprising more than one nucleoside to give a further oxidized compound;

(h) cleaving said oxidized compound or said further oxidized compound from the support medium to give said oligomeric compound comprising a linking moiety, wherein said cleaving is performed using a bifunctional compound having an internal disulfide group;

(i) treating said linking moiety attached to said oligomeric compound with reagents effective to form a reactive sulfur moiety on said linking moiety; and (j) reacting said reactive sulfur moiety with a peptide wherein said peptide is functionalized with a functional group reactive with said sulfur moiety thereby forming said peptide linked oligomeric compound.

23. The method of claim 22 where said bifunctional compound has the formula $H_2N\text{-}(CH_2)_q\text{—}S\text{—}S\text{—}(CH_2)_q\text{—}NH_2$ wherein each q is from 2 to about 6.

24. A compound having the formula:

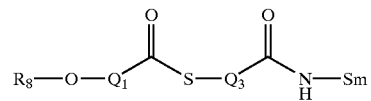

wherein:

$R_8$ is hydrogen, a hydroxyl protecting group, a nucleoside, a nucleotide or an oligomeric compound;

$Q_1$ propyl and Q is methyl; and

Sm is a support medium.

* * * * *

UNITED STATES PATENT AND TRADEMARK OFFICE
CERTIFICATE OF CORRECTION

PATENT NO. : 6,762,281 B2
DATED : July 13, 2004
INVENTOR(S) : Muthiah Manoharan et al.

It is certified that error appears in the above-identified patent and that said Letters Patent is hereby corrected as shown below:

<u>Column 69,</u>
Line 64, delete "K" after "2.";

<u>Column 71,</u>
Line 37, delete "T," and insert -- $T_1$ --;
Line 38, insert -- - -- after "$Q_2$";
Line 40, insert -- $_p$ -- after "]";
Line 45, delete "$G_2$" and insert -- G --;
Line 49, delete "$CH_3(CH_2)_5$-O-" and insert -- $CH_3(CH_2)_g$-O- --;
Line 53, delete "$GH_2CH_2CN$" and insert -- $CH_2CH_2CN$ --;
Line 54, delete "-$CH_2CH=GH_2$" and insert -- -$CH_2CH=CH_2$ --;

<u>Column 72,</u>
Line 62, delete "-$C(CH_3)(CH_3)$-CCl3" and insert -- -$C(CH_3)(CH_3)$-$CCl_3$ --;

<u>Column 74,</u>
Lines 1-13, delete formula " 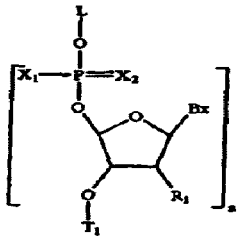 " and insert

-- 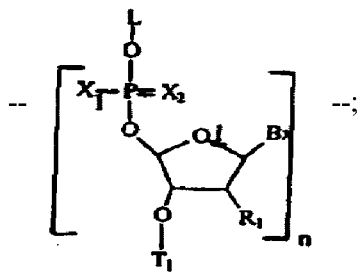 --;

Line 62, delete "-$[(CH_2)_{mm}$-O-$CH_2)_{mm'}]$." and insert -- -$[(CH_2)_{mm}$-O-$CH_2)_{mm'}]_p$- --;

UNITED STATES PATENT AND TRADEMARK OFFICE
CERTIFICATE OF CORRECTION

PATENT NO. : 6,762,281 B2
DATED : July 13, 2004
INVENTOR(S) : Muthiah Manoharan et al.

It is certified that error appears in the above-identified patent and that said Letters Patent is hereby corrected as shown below:

<u>Column 75,</u>
Line 13, delete "R9" and insert -- $R_9$ --; delete "hydroxyl]" and insert -- hydroxyl --;
Lines 14-15, delete "-$[(CH_2)_{mm}\text{-}1\text{-}(CH_2)_{mm'}]_p$-" and insert
-- -$[(CH_2)_{mm}\text{-}O\text{-}(CH_2)_{mm'}]_p$- --;

<u>Column 78,</u>
Line 13, delete "Q" and insert -- $Q_3$ --.

Signed and Sealed this

Sixth Day of June, 2006

JON W. DUDAS
*Director of the United States Patent and Trademark Office*

SEQUENCE LISTING

<160> NUMBER OF SEQ ID NOS: 24

<210> SEQ ID NO 1
<211> LENGTH: 20
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (6)..(6)
<223> OTHER INFORMATION: 5Me for this deoxy C
<220> FEATURE:
<221> NAME/KEY: misc_feature
<222> LOCATION: (9)..(9)
<223> OTHER INFORMATION: 5Me for this deoxy C
<220> FEATURE:
<221> NAME/KEY: misc_feature
<222> LOCATION: (11)..(11)
<223> OTHER INFORMATION: 5Me for this deoxy C

<400> SEQUENCE: 1
tccgtcatcg ctcctcaggg                                                  20

<210> SEQ ID NO 2
<211> LENGTH: 20
<212> TYPE: DNA
<213> ORGANISM: Artificial Sequence
<220> FEATURE:
<223> OTHER INFORMATION: Synthetic construct

<400> SEQUENCE: 2
agcttctttg cacatgtaaa                                                  20

<210> SEQ ID NO 3
<211> LENGTH: 20
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (10)..(11)

```
<223> OTHER INFORMATION: 5Me for this deoxy C
<220> FEATURE:
<221> NAME/KEY: misc_feature
<222> LOCATION: (13)..(13)
<223> OTHER INFORMATION: 5Me for this deoxy C
<220> FEATURE:
<221> NAME/KEY: misc_feature
<222> LOCATION: (15)..(15)
<223> OTHER INFORMATION: 5Me for this deoxy C

<400> SEQUENCE: 3
ctacgctttc cacgcacagt                                           20

<210> SEQ ID NO 4
<211> LENGTH: 20
<212> TYPE: DNA
<213> ORGANISM: Artificial Sequence
<220> FEATURE:
<223> OTHER INFORMATION: Synthetic construct

<400> SEQUENCE: 4
tctgagtagc agaggagctc                                           20

<210> SEQ ID NO 5
<211> LENGTH: 20
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(2)
<223> OTHER INFORMATION: 5Me for this deoxy C
<220> FEATURE:
<221> NAME/KEY: misc_feature
<222> LOCATION: (7)..(9)
<223> OTHER INFORMATION: 5Me for this deoxy C

<400> SEQUENCE: 5
ccggtacccc aggttcttca                                           20

<210> SEQ ID NO 6
<211> LENGTH: 20
<212> TYPE: DNA
<213> ORGANISM: Artificial Sequence
<220> FEATURE:
<223> OTHER INFORMATION: Synthetic construct

<400> SEQUENCE: 6
gaccgtctct tccttctgga                                           20

<210> SEQ ID NO 7
<211> LENGTH: 19
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(1)
<223> OTHER INFORMATION: Xaa is gamma aminobutyric acid

<400> SEQUENCE: 7

Xaa Gly Gly Arg Gln Ile Lys Ile Trp Phe Gln Asn Arg Arg Met Lys
 1               5                  10                  15

Trp Lys Lys

<210> SEQ ID NO 8
```

```
<211> LENGTH: 20
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (2)..(2)
<223> OTHER INFORMATION: Xaa is gamma aminobutyric acid

<400> SEQUENCE: 8

Cys Xaa Gly Gly Arg Gln Ile Lys Ile Trp Phe Gln Asn Arg Arg Met
1               5                   10                  15

Lys Trp Lys Lys
            20

<210> SEQ ID NO 9
<211> LENGTH: 7
<212> TYPE: PRT
<213> ORGANISM: Artificial Sequence
<220> FEATURE:
<223> OTHER INFORMATION: Synthetic construct

<400> SEQUENCE: 9

Arg Gly Asp Pro Tyr Cys Gly
1               5

<210> SEQ ID NO 10
<211> LENGTH: 8
<212> TYPE: PRT
<213> ORGANISM: Artificial Sequence
<220> FEATURE:
<223> OTHER INFORMATION: Synthetic construct

<400> SEQUENCE: 10

Gly Asn Gly Arg Pro Tyr Cys Gly
1               5

<210> SEQ ID NO 11
<211> LENGTH: 8
<212> TYPE: PRT
<213> ORGANISM: Artificial Sequence
<220> FEATURE:
<223> OTHER INFORMATION: Synthetic construct

<400> SEQUENCE: 11

Gly Arg Gly Asp Pro Tyr Cys Gly
1               5

<210> SEQ ID NO 12
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (2)..(2)
<223> OTHER INFORMATION: Xaa is gamma aminobutyric acid

<400> SEQUENCE: 12

Cys Xaa Trp Phe Arg Arg Arg Arg
1               5

<210> SEQ ID NO 13
<211> LENGTH: 10
<212> TYPE: PRT
<213> ORGANISM: Artificial Sequence
```

```
<220> FEATURE:
<223> OTHER INFORMATION: Synthetic construct
<220> FEATURE:
<221> NAME/KEY: misc_feature
<222> LOCATION: (2)..(2)
<223> OTHER INFORMATION: Xaa is gamma aminobutyric acid

<400> SEQUENCE: 13

Cys Xaa Trp Phe Arg Arg Arg Arg Arg
1               5

<210> SEQ ID NO 14
<211> LENGTH: 13
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (2)..(2)
<223> OTHER INFORMATION: Xaa is gamma aminobutyric acid

<400> SEQUENCE: 14

Cys Xaa Trp Phe Arg Arg Arg Arg Arg Arg Arg Arg
1               5                   10

<210> SEQ ID NO 15
<211> LENGTH: 13
<212> TYPE: PRT
<213> ORGANISM: Artificial Sequence
<220> FEATURE:
<223> OTHER INFORMATION: Synthetic construct

<400> SEQUENCE: 15

Gly Arg Lys Lys Arg Arg Gly Arg Arg Arg Gly Trp Cys
1               5                   10

<210> SEQ ID NO 16
<211> LENGTH: 14
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(1)
<223> OTHER INFORMATION: Xaa is gamma aminobutyric acid

<400> SEQUENCE: 16

Xaa Gly Gly Ala Cys Asp Cys Arg Gly Asp Cys Phe Cys Gly
1               5                   10

<210> SEQ ID NO 17
<211> LENGTH: 14
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(1)
<223> OTHER INFORMATION: Xaa is gamma aminobutyric acid
<220> FEATURE:
<221> NAME/KEY: misc_feature
<222> LOCATION: (4)..(5)
<223> OTHER INFORMATION: Cysteines are crosslinked
<220> FEATURE:
<221> NAME/KEY: misc_feature
<222> LOCATION: (6)..(7)
<223> OTHER INFORMATION: Cysteines are crosslinked
<220> FEATURE:
```

```
<221> NAME/KEY: misc_feature
<222> LOCATION: (10)..(11)
<223> OTHER INFORMATION: Cysteines are crosslinked
<220> FEATURE:
<221> NAME/KEY: misc_feature
<222> LOCATION: (12)..(13)
<223> OTHER INFORMATION: Cysteines are crosslinked

<400> SEQUENCE: 17

Xaa Gly Gly Ala Cys Asp Cys Arg Gly Asp Cys Phe Cys Gly
1               5                   10

<210> SEQ ID NO 18
<211> LENGTH: 4
<212> TYPE: PRT
<213> ORGANISM: Artificial Sequence
<220> FEATURE:
<223> OTHER INFORMATION: Synthetic construct

<400> SEQUENCE: 18

Leu Gly Ile Gly
1

<210> SEQ ID NO 19
<211> LENGTH: 16
<212> TYPE: PRT
<213> ORGANISM: Artificial Sequence
<220> FEATURE:
<223> OTHER INFORMATION: Synthetic construct

<400> SEQUENCE: 19

Asp Pro Asp Gly Leu Gly His Ala Ala Lys His Glu Ala Ala Ala Lys
1               5                   10                  15

<210> SEQ ID NO 20
<211> LENGTH: 18
<212> TYPE: DNA
<213> ORGANISM: Artificial Sequence
<220> FEATURE:
<223> OTHER INFORMATION: Synthetic construct

<400> SEQUENCE: 20
tgtgctattc tgtgaatt                                              18

<210> SEQ ID NO 21
<211> LENGTH: 20
<212> TYPE: DNA
<213> ORGANISM: Artificial Sequence
<220> FEATURE:
<223> OTHER INFORMATION: Synthetic construct

<400> SEQUENCE: 21
agcttctttg cacatgtaaa                                            20

<210> SEQ ID NO 22
<211> LENGTH: 13
<212> TYPE: PRT
<213> ORGANISM: Artificial Sequence
<220> FEATURE:
<223> OTHER INFORMATION: Synthetic construct

<400> SEQUENCE: 22

Gly Arg Lys Lys Arg Arg Gly Arg Arg Gly Tyr Cys
1               5                   10

<210> SEQ ID NO 23
<211> LENGTH: 18
```

```
<212> TYPE: DNA
<213> ORGANISM: Artificial Sequence
<220> FEATURE:
<223> OTHER INFORMATION: Synthetic construct

<400> SEQUENCE: 23
tgttattctt tagaatgg                                           18

<210> SEQ ID NO 24
<211> LENGTH: 13
<212> TYPE: PRT
<213> ORGANISM: Artificial Sequence
<220> FEATURE:
<223> OTHER INFORMATION: Synthetic construct

<400> SEQUENCE: 24

Gly Arg Lys Lys Arg Arg Gln Arg Arg Arg Pro Pro Gln
1               5                   10
```